US009132005B2

(12) United States Patent
Blum

(10) Patent No.: US 9,132,005 B2
(45) Date of Patent: Sep. 15, 2015

(54) EYE APERTURE ENHANCING PROSTHESIS AND METHOD

(71) Applicant: BeautiEyes, LLC, Roanoke, VA (US)

(72) Inventor: Ronald D. Blum, Roanoke, VA (US)

(73) Assignee: BeautiEyes, LLC, Roanoke, VA (US)

( * ) Notice: Subject to any disclaimer, the term of this patent is extended or adjusted under 35 U.S.C. 154(b) by 0 days.

(21) Appl. No.: 14/509,878

(22) Filed: Oct. 8, 2014

(65) Prior Publication Data

US 2015/0025626 A1 Jan. 22, 2015

Related U.S. Application Data

(63) Continuation of application No. 14/018,244, filed on Sep. 4, 2013, which is a continuation of application No. PCT/US2013/058175, filed on Sep. 5, 2013.

(60) Provisional application No. 61/698,205, filed on Sep. (Continued)

(51) Int. Cl.
*A61F 2/14* (2006.01)
*A61F 9/007* (2006.01)
*G02C 7/04* (2006.01)

(52) U.S. Cl.
CPC ............... *A61F 2/14* (2013.01); *A61F 9/00718* (2013.01); *G02C 7/049* (2013.01)

(58) Field of Classification Search
CPC ....... A61F 2/14; A61F 2/145; A61F 9/00718; G02C 7/046–7/049; G02C 7/068
See application file for complete search history.

(56) References Cited

U.S. PATENT DOCUMENTS

| 3,698,802 | A | | 10/1972 | Baron |
| 4,084,890 | A | * | 4/1978 | Baron ...................... 351/159.02 |
| 4,239,353 | A | * | 12/1980 | Koller ...................... 351/159.02 |
| 5,650,837 | A | | 7/1997 | Roffman et al. |
| 5,652,638 | A | | 7/1997 | Roffman et al. |
| 5,760,870 | A | | 6/1998 | Payor |
| 5,912,719 | A | | 6/1999 | Baude et al. |
| 6,092,899 | A | | 7/2000 | Wanders |
| 6,183,082 | B1 | | 2/2001 | Clutterbuck |
| 6,491,392 | B2 | | 12/2002 | Roffman et al. |

(Continued)

FOREIGN PATENT DOCUMENTS

| DE | 431950 | 7/1926 |
| EP | 0 062 178 A1 | 10/1982 |

(Continued)

OTHER PUBLICATIONS

Notification of Transmittal of the International Search Report and the Written Opinion of the International Searching Authority, or the Declaration for PCT/US2013/058175, dated Feb. 21, 2014, 23 pages.

(Continued)

*Primary Examiner* — Howie Matthews
(74) *Attorney, Agent, or Firm* — Sterne, Kessler, Goldstein & Fox P.L.L.C.

(57) ABSTRACT

A prosthesis capable of being worn on the eye of a wearer having a convex surface and a concave surface. The prosthesis has an aperture widening zone for widening the natural palpebral fissure of the wearer's eye. The prosthesis widens the natural palpebral fissure (aperture) of the wearer's eye by at least 1 mm. A method of widening the natural palpebral fissure of a wearer's eye by at least 1 mm is also provided.

29 Claims, 71 Drawing Sheets

Related U.S. Application Data 7, 2012, provisional application No. 61/702,274, filed on Sep. 18, 2012, provisional application No. 61/706,827, filed on Sep. 28, 2012, provisional application No. 61/714,567, filed on Oct. 16, 2012, provisional application No. 61/716,633, filed on Oct. 22, 2012, provisional application No. 61/721,530, filed on Nov. 2, 2012, provisional application No. 61/726,096, filed on Nov. 14, 2012, provisional application No. 61/729,020, filed on Nov. 21, 2012, provisional application No. 61/730,185, filed on Nov. 27, 2012, provisional application No. 61/736,210, filed on Dec. 12, 2012, provisional application No. 61/757,365, filed on Jan. 28, 2013, provisional application No. 61/835,709, filed on Jun. 17, 2013, provisional application No. 61/859,360, filed on Jul. 29, 2013.

(56) References Cited

U.S. PATENT DOCUMENTS

| | | |
|---|---|---|
| 6,939,005 B2 | 9/2005 | Jubin et al. |
| 7,036,930 B2 | 5/2006 | Jubin et al. |
| 7,159,979 B2 | 1/2007 | Jubin et al. |
| 8,646,908 B2 * | 2/2014 | Clutterbuck et al. .... 351/159.36 |
| 2002/0024631 A1 | 2/2002 | Roffman et al. |
| 2006/0050232 A1 * | 3/2006 | Dukes et al. ................ 351/162 |
| 2012/0147319 A1 | 6/2012 | Corti et al. |

FOREIGN PATENT DOCUMENTS

| | | |
|---|---|---|
| EP | 0 471 313 A2 | 2/1992 |
| EP | 0 980 015 A1 | 2/2000 |
| EP | 1 008 890 A1 | 6/2000 |
| EP | 1 014 154 A1 | 6/2000 |
| WO | WO 01/16641 A1 | 3/2001 |
| WO | WO 2011/084677 A1 | 7/2011 |
| WO | WO 2011/084678 A1 | 7/2011 |
| WO | WO 2011/084681 A1 | 7/2011 |
| WO | WO 2011/133376 A1 | 10/2011 |
| WO | WO 2012/083195 A2 | 6/2012 |

OTHER PUBLICATIONS

U.S. Appl. No. 14/680,854, filed Apr. 7, 2015.

* cited by examiner

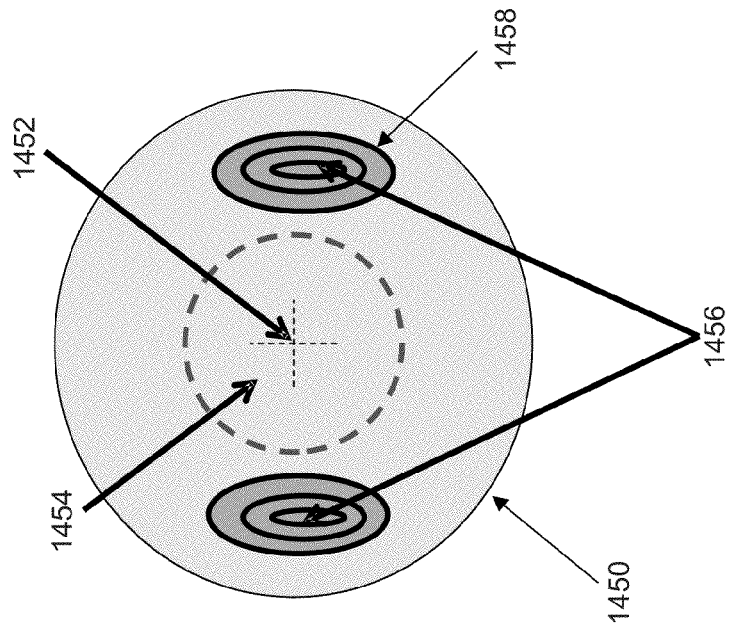
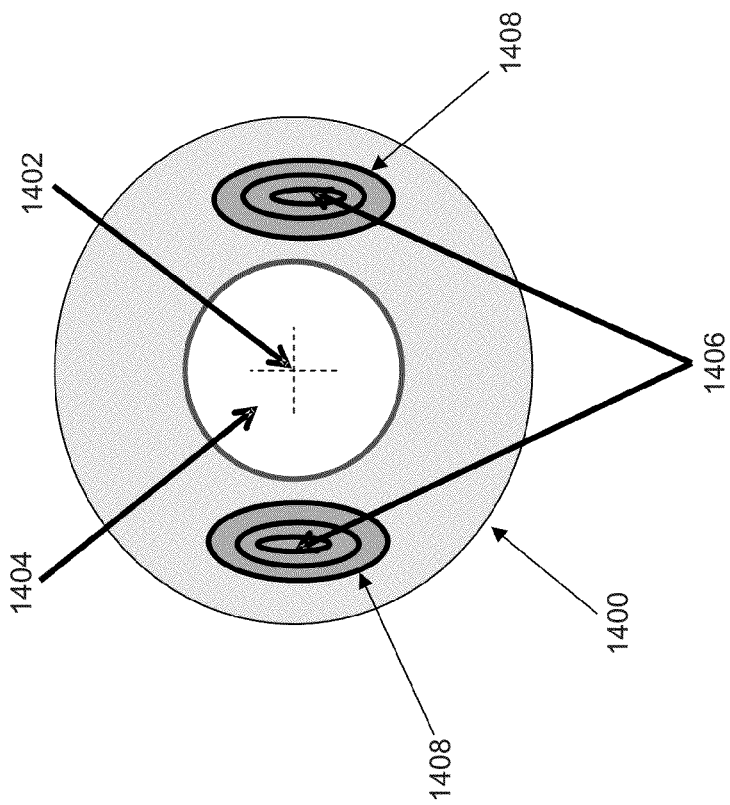

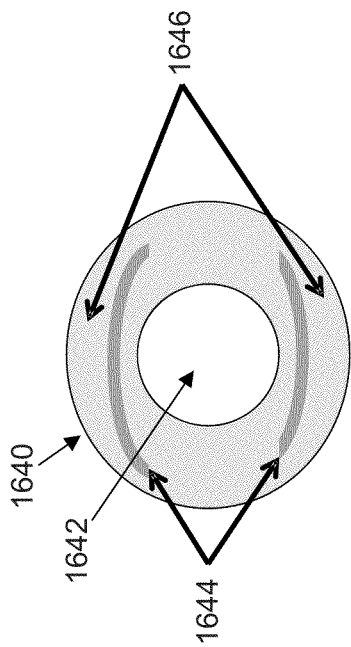
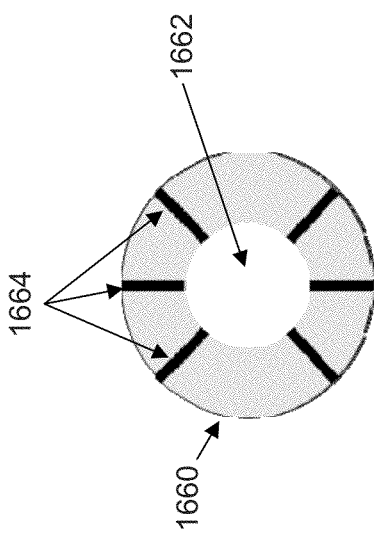
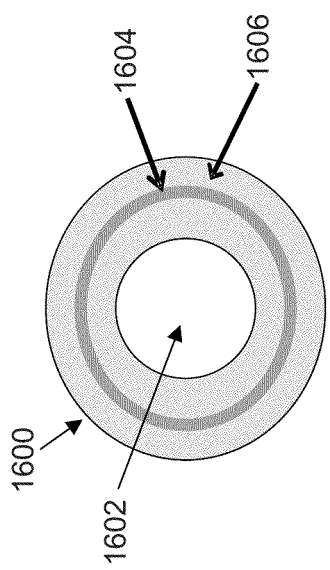
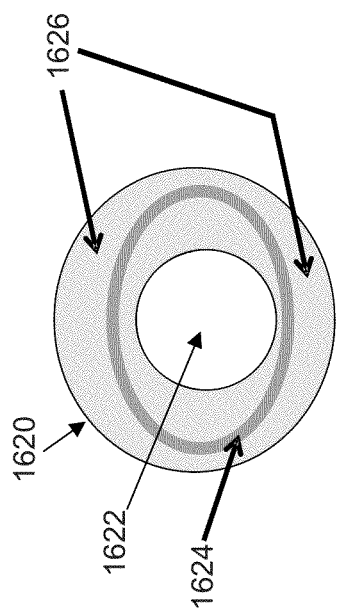
FIG. 16A
FIG. 16B
FIG. 16C
FIG. 16D

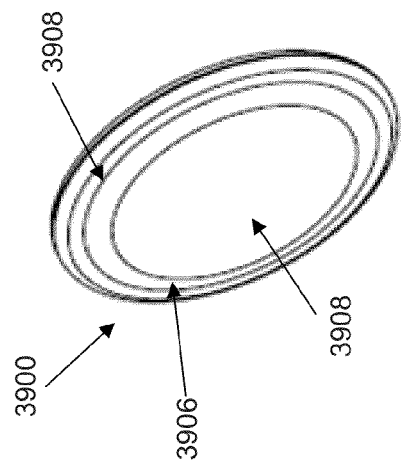
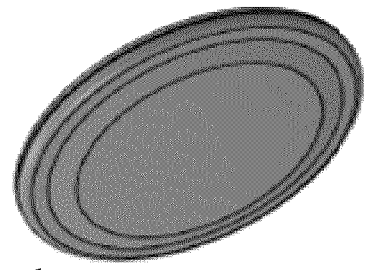
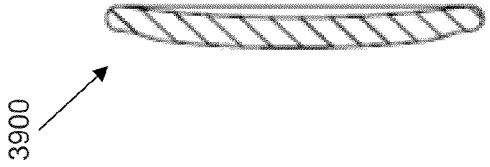
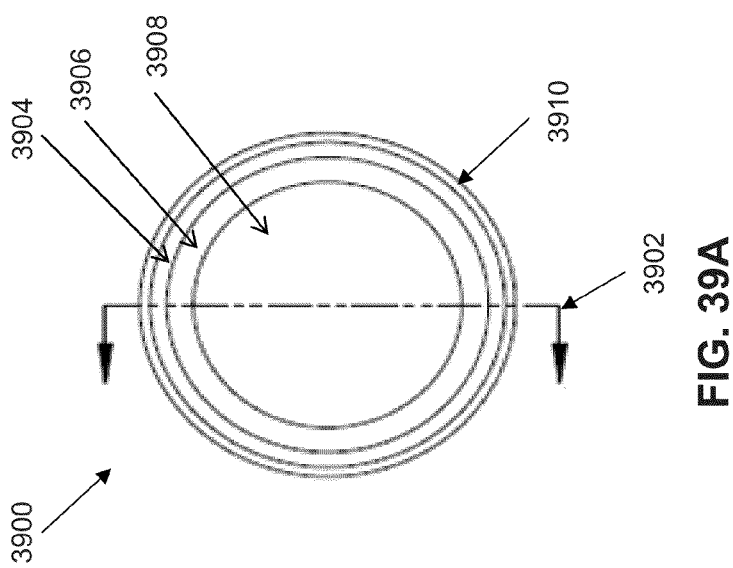

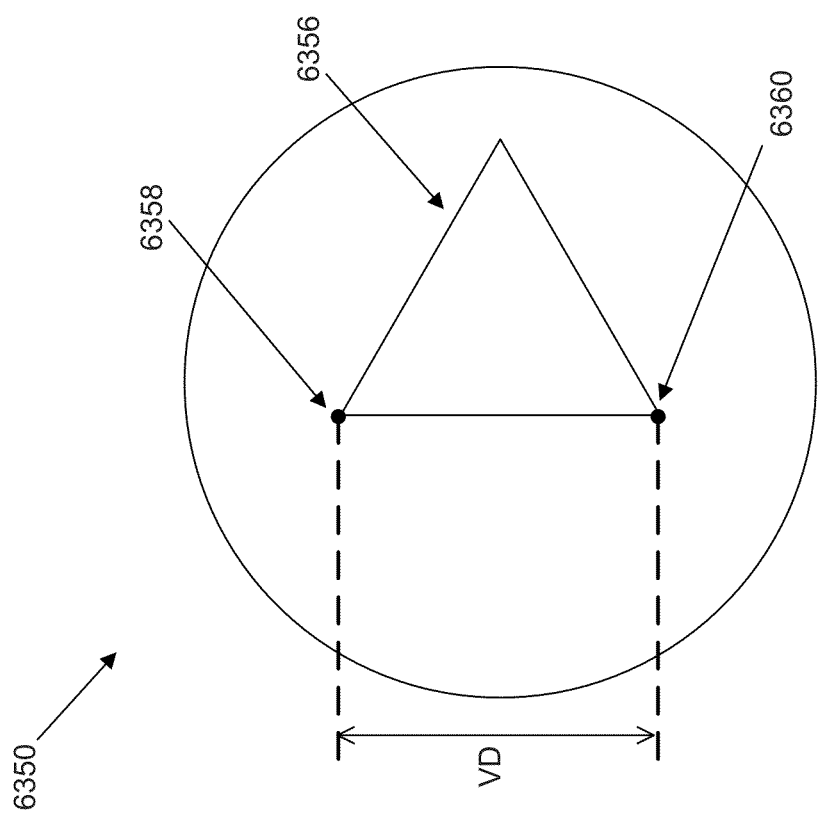

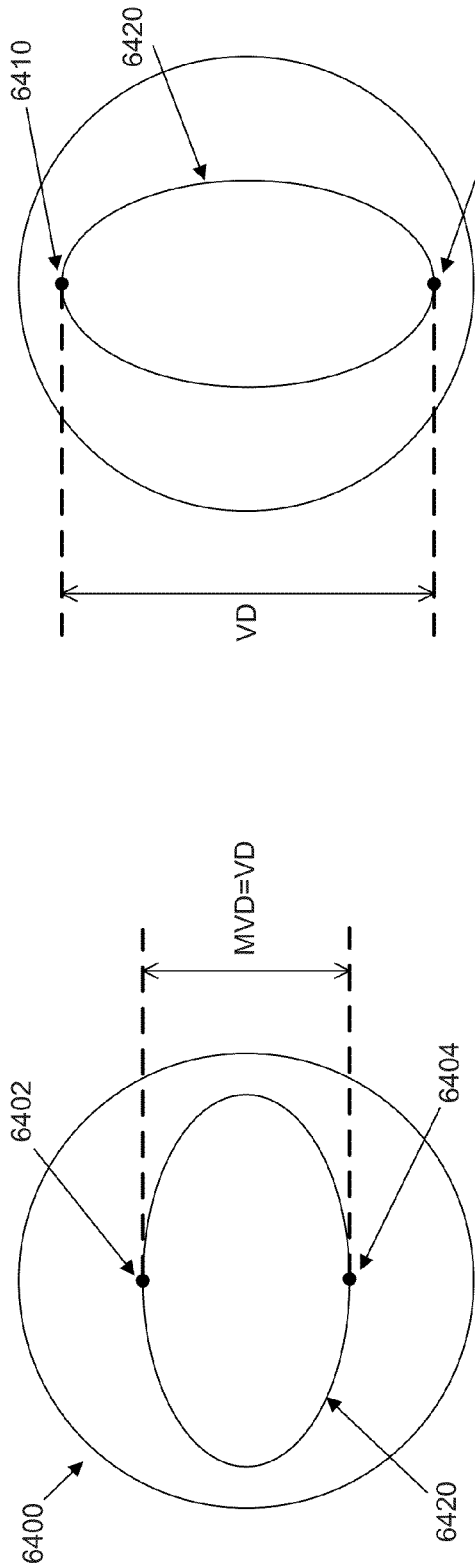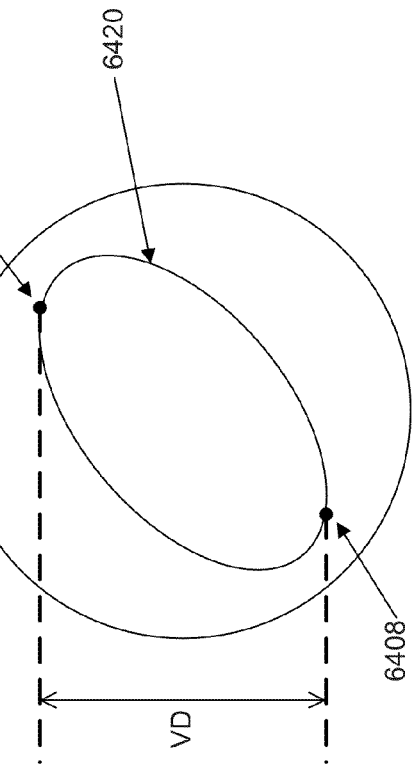
FIG. 64B
FIG. 64C
FIG. 64A

EYE APERTURE ENHANCING PROSTHESIS AND METHOD

CROSS-REFERENCE TO RELATED APPLICATIONS

This application is a continuation of U.S. application Ser. No. 14/018,244, titled "Eye Aperture Enhancing Prosthesis and Method," filed on Sep. 4, 2013. This application claims priority to the following U.S. Provisional Patent Applications via U.S. application Ser. No. 14/018,244, all of which are hereby incorporated by reference in their entirety:

Ser. No. 61/698,205, titled "Novel Lid Lifting Contact Lens Design and Use", filed Sep. 7, 2012;

Ser. No. 61/702,274, titled "Novel Cosmetic Contact Lens", filed Sep. 18, 2012;

Ser. No. 61/706,827, titled "Novel Cosmetic Eye Widening Contact Lens", filed Sep. 28, 2012;

Ser. No. 61/714,567, titled "Cosmetic Eye Widening Contact Lens", filed Oct. 16, 2012;

Ser. No. 61/716,633, titled "Fitting Method and Contact Len Design of Inventive Palpebral Fissure Widening Contact Lens", filed Oct. 22, 2012;

Ser. No. 61/721,530, titled "Contact Lens Design for Widening Palpebral Fissure of Wearer's Eye, filed Nov. 2, 2012;

Ser. No. 61/726,096, titled "Improved Contact Lens Design for Widening Palpebral Fissure of Wearer's Eye", filed Nov. 14, 2012;

Ser. No. 61/729,020, titled "Palpebral Fissure Widening Contact Lens", filed Nov. 21, 2012;

Ser. No. 61/730,185, titled "Palpebral Fissure Widening Contact Lens", filed Nov. 27, 2012;

Ser. No. 61/736,210, titled "Enhanced Palpebral Fissure Widening Contact Lens", filed Dec. 12, 2012;

Ser. No. 61/757,365 titled "Corneal Scleral Contact Lens for Palpebral Widening", filed Jan. 28, 2013;

Ser. No. 61/835,709, titled "Palpebral Fissure Enhancing Scleral Ring", filed Jun. 17, 2013; and Ser. No. 61/859,360, titled "Eye Aperture Enhancing Prosthesis", filed Jul. 29, 2013.

This application is a continuation of International Application PCT/US2013/058175, titled "Eye Aperture Enhancing Prosthesis and Method," with an international filing date of Sep. 5, 2013, which is hereby incorporated by reference in its entirety.

FIELD OF THE INVENTION

The present application relates to prostheses for use in the eye, and specifically, to the field of prostheses that enhance or alter the appearance of a wearer's eye.

BACKGROUND

Today's corneo-scleral contact lenses (soft contact lenses or hybrid contact lenses) that fit on the cornea of one's eye (do not vault the cornea) and extend over the limbus and bulbar conjunctiva thus covering part of the sclera are not being used for correcting ptosis and/or the widening of the wearer's palpebral fissure. This is due to their geometrical design. Also corneal contact lenses (rigid or soft) that fit only the cornea and do not extend past the limbus are not used for correcting ptosis and/or the widening of the wearer's palpebral fissure due to geometrical design and overall diameter. Scleral contact lenses are hard/rigid and have been designed in the past to fit snugly against the sclera of the wearer's eye, "vault the cornea" and have a very thick edge design such to lift the upper lid of the wearer's eye having ptosis. While sclera contact lenses have existed in the past that will lift the upper lid of the wearer's eye these hard/rigid sclera contact lenses are highly uncomfortable, cause very red eyes and irritate the eye lid margin thus presenting severe limitations for the wearer. For these reasons the commercial success of sclera contact lenses to correct for ptosis has been a major failure. In addition, it is known that the aperture of the human eye reduces in overall diameter by 1.5 mm or more as one matures from that of a child to that of an adult of the age of 40 and even more as one matures to that of a senior of 60 years or older. Thus there is a need for a non-surgical comfortable means to open up the aperture of the eye to maintain a youthful look and/or restore some of or all lost visual field function in the case of ptosis.

SUMMARY OF THE INVENTION

Some embodiments include a prosthesis capable of being worn on the eye of a wearer having a convex surface and a concave surface. The prosthesis has an aperture widening zone located on the convex surface. The prosthesis widens the natural palpebral fissure of the wearer's eye by at least 1 mm.

Some embodiments include a prosthesis capable of being worn on the eye of a wearer. The prosthesis has a convex surface and a concave surface. An aperture widening zone is located on the convex surface. The prosthesis is a corneo-scleral contact lens that widens the natural palpebral fissure of the wearer's eye by at least 1 mm.

Some embodiments include a prosthesis having a convex surface and a concave surface. An aperture widening zone is located on the convex surface. The prosthesis is a scleral ring that widens the natural palpebral fissure of the wearer's eye by at least 1 mm.

Some embodiments include a prosthesis capable of being worn on the eye of a wearer. The prosthesis has a convex surface and a concave surface. An aperture widening zone is located on the convex surface. The aperture widening zone includes at least one surface feature. The prosthesis widens the natural palpebral fissure of the wearer's eye by at least 1 mm.

Some embodiments include a prosthesis capable of being worn on the eye of a wearer having a convex surface, a concave surface, and a peripheral edge. The prosthesis also has an aperture widening zone located on the convex surface. The aperture widening zone including an outer slope and an inner slope with a maximum change in thickness located in between. The outer slope and the inner slope are different.

Some embodiments include a prosthesis capable of being worn on the eye of a wearer having a convex surface, a concave surface, and a peripheral edge. The prosthesis also has an aperture widening zone located on the convex surface. The aperture widening zone including an outer slope and an inner slope with a maximum change in thickness located in between.

Some embodiments include a prosthesis capable of being worn on the eye of a wearer. The prosthesis has a convex surface and a concave surface. An aperture widening zone is located on the convex surface. The aperture widening zone has at least one surface feature. The aperture widening zone also has a minimum vertical dimension.

Some embodiments include a prosthesis capable of being worn on the eye of a wearer. The prosthesis has a convex surface, a concave surface, a peripheral edge, and a geometric center. An aperture widening zone is located on the convex surface. The aperture widening zone has at least one surface feature. At least a portion of the at least one surface feature is located at or outside 5.25 mm from the geometric center of the prosthesis.

In some embodiments the prosthesis has an overall diameter of at least 14.0 mm. In other embodiments the prosthesis has an overall diameter of at least 14.5 mm. In some embodiments the prosthesis has an overall diameter of at least 15 mm. In some embodiments the prosthesis has an overall diameter of at least 15.5 mm. In still some other embodiments the prosthesis has an overall diameter of at least 16.0 mm or larger.

In some embodiments the prosthesis is a rotationally symmetric lens. In some embodiments the prosthesis is capable of rotating. In some embodiments the prosthesis is not capable of rotating.

In some embodiments the aperture widening zone depresses a lower eye lid of the wearer by at least 1 mm. In some embodiments the aperture widening zone elevates an upper eye lid of the wearer by at least 1 mm.

In some embodiments the prosthesis includes a colored accent color. In some embodiments the colored accent color is around a portion of the prosthesis which fits near or at the limbus of the eye when the prosthesis is worn. In some embodiments the colored accent color is a limbal ring, circle ring, or circle lens.

In some embodiments the prosthesis is a multifocal contact lens. In some embodiments the prosthesis is a toric contact lens. In some embodiments the prosthesis is a single vision contact lens.

In some embodiments the aperture widening zone comprises an area of increased surface friction. In some embodiments the increased surface friction is provided by a surface treatment, a coating, a different material, surface dimples, surface irregularities, or combinations thereof In some embodiments the aperture widening zone also includes an outer slope and an inner slope with a maximum change in thickness located in between. In some embodiments the outer slope and inner slope are different. In some embodiments the outer slope is greater than the inner slope. In some embodiments the outer slope has an angle between 3° and 45°. In some embodiments the outer slope has an angle between 5° and 25°. In some embodiments the inner slope comprises an angle between 1° and 15°.

In some embodiments the aperture widening zone has an incremental thickness and a maximum change in thickness. In some embodiments the maximum change in thickness is within a range of 25 microns to 1,000 microns. In some embodiments the maximum change in thickness is within a range of 100 microns to 500 microns. In some embodiments the maximum change in thickness is within a range of 75 microns to 400 microns. In some embodiments the maximum change in thickness is located between 1.0 mm and 2.5 mm from an outer edge of the prosthesis. In some embodiments the maximum change in thickness is located at or exterior to the corneal limbus of the wearer's eye when the prosthesis is worn on the eye. In some embodiments the incremental thickness is an increase in thickness. In some embodiments the incremental thickness is a decrease in thickness.

In some embodiments an outermost part of the aperture widening zone is located within a range of 3 mm to 8.5 mm from a geometric center of the prosthesis. In some embodiments an outermost part of the aperture widening zone is located within a range of 5 mm to 7.75 mm from a geometric center of the prosthesis. In some embodiments an innermost part of the aperture widening zone is located between a peripheral edge of the prosthesis and 6 mm from a peripheral edge of the prosthesis.

In some embodiments a minimum vertical dimension of the aperture widening zone is larger than a maximum vertical diameter of the natural palpebral fissure of the wearer's eye. In some embodiments a minimum vertical dimension of the aperture widening zone is equal to or greater than 10.5 mm. In some embodiments a minimum vertical dimension of the aperture widening zone is equal to or greater than 11 mm. In some embodiments a minimum vertical dimension of the aperture widening zone is equal to or greater than 11.5 mm. In some embodiments a minimum vertical dimension of the aperture widening zone is equal to or greater than 12 mm. In some embodiments a minimum vertical dimension of the aperture widening zone is a vertical distance between an uppermost part of the aperture widening zone and a lowermost part of the aperture widening zone.

In some embodiments the aperture widening zone includes at least one surface feature. In some embodiments the aperture widening zone has a plurality of surface features.

In some embodiments the prosthesis is a corneo-scleral contact lens. In some embodiments the prosthesis is a scleral ring.

In some embodiments the aperture widening zone has a minimum vertical dimension.

In some embodiments the prosthesis also has a peripheral edge, a geometric center, and at least one surface feature. In some embodiments the at least one surface feature or at least a portion of the at least one surface is located at or outside 5.25 mm from the geometric center of the prosthesis. In some embodiments the peripheral edge has a knife edge shape, a rounded shape, a blunt shape, or a semi-rounded shape. In some embodiments the peripheral edge has a thickness between 25 microns and 100 microns.

In some embodiments the prosthesis has a hybrid design. In some embodiments the prosthesis has a homogeneous design.

In some embodiments the aperture widening zone comprises a ring, multiple rings, a partial ring, multiple partial rings, an island, multiple islands, a band, bands, partial bands, a segmented area, or multiple segmented areas.

In some embodiments the prosthesis can be worn by the wearer continuously. In some embodiments the prosthesis can be worn by the wearer non-continuously. In some embodiments the prosthesis can be worn by the wearer daily, weekly, or monthly.

In some embodiments the prosthesis is disposable. In some embodiments the prosthesis is reusable.

In some embodiments the prosthesis comprises an optical power. In some embodiments the prosthesis does not comprise an optical power.

Some embodiments include a prosthesis having an aperture widening zone. The aperture widening zone has an outer slope, an inner slope, a point of maximum added thickness delta, and an incremental thickness diameter. The prosthesis also has a peripheral edge, a geometrical center, and an overall diameter. The overall diameter is measured from a first point on the peripheral edge to a second point on the opposing peripheral edge thru the geometrical center of the prosthesis and the aperture widening zone. The overall diameter is 14.5 mm or greater. The outer slope is with the range of 5 degrees and 25 degrees. The point of maximum added thickness delta of the aperture widening zone is 75 microns or greater. The point of maximum added thickness delta of the aperture widening zone is located between 1 mm and 3 mm from the peripheral edge. The incremental thickness diameter is 10.5 mm or greater.

In some embodiments the prosthesis is free to rotate. In some embodiments the prosthesis is not free to rotate.

In some embodiments the incremental thickness diameter is 1 mm larger than the vertical measurement of the natural aperture of the wearer's eye.

In some embodiments the prosthesis is a single vision contact lens. In some embodiments the prosthesis is a multi-focal contact lens. In some embodiments the prosthesis is a toric contact lens.

In some embodiments the prosthesis includes a hydrogel. In some embodiments the prosthesis includes a silicone hydrogel. In some embodiments the prosthesis includes a homogenous material. In some embodiments the prosthesis includes hybrid materials.

In some embodiments the aperture widening zone begins at or adjacent to the peripheral edge. In some embodiments the aperture widening zone begins internal to the peripheral edge.

In some embodiments the point of maximum added thickness delta is 100 microns or greater. In some embodiments the point of maximum added thickness delta is 125 microns or greater. In some embodiments the point of maximum added thickness delta is 150 microns or greater. In some embodiments the point of maximum added thickness delta is 200 microns or greater. In some embodiments the point of maximum added thickness delta is 225 microns or greater. In some embodiments the point of maximum added thickness delta is 250 microns or greater.

In some embodiments the prosthesis is one of: daily wear, disposable, continuous wear, weekly wear, or monthly wear.

In some embodiments the prosthesis is not stabilized.

In some embodiments the aperture widening zone is a round ring. In some embodiments the aperture widening zone is a series of partial segments that make up a ring.

Some embodiments provide for a method of widening the natural palpebral fissure of a wearer's eye by providing a protocol or instructions for widening the wearer's natural palpebral fissure by at least 1 mm and providing at least one prosthesis comprising an aperture widening zone located on its convex surface. In some embodiments the protocol or instructions include directions to determine a vertical dimension of the wearer's natural palpebral fissure, and to provide the wearer with a prosthesis having a minimum vertical dimension at least 1 mm greater than a maximum vertical dimension of the natural palpebral fissure.

It will be appreciated that various embodiments recited above with respect to the prosthesis and/or aperture widening zone can be combined in any combination, except where features are mutually exclusive.

BRIEF DESCRIPTION OF THE DRAWINGS

FIG. 14A shows a contact lens with an aperture widening zone according to one embodiment. FIG. 14B shows a scleral ring with an aperture widening zone according to one embodiment.

FIGS. 16A-D show various embodiments of a scleral ring with different aperture widening zones having an incremental thickness.

FIG. 18 shows the individual's natural eyes and FIG. 19 shows the same individual wearing a prosthesis having an aperture widening zone.

FIG. 20 shows the individual's natural eye.

FIG. 22A shows the individual's natural left eye and FIG. 22B shows the individual wearing a prosthesis having an aperture widening zone in the left eye.

FIG. 24A shows the individual's natural eyes and FIG. 24B shows the same individual wearing a prosthesis having an aperture widening zone.

FIGS. 39A-E illustrate the surface profile of a contact lens 3900 according to one embodiment. FIG. 39A shows an aerial view of the contact lens. FIG. 39B shows a side view of the contact lens. FIG. 39C shows a cross-sectional view of the contact lens along its central axis. FIG. 39D shows the convex surface of the contact lens. FIG. 39E shows the concave surface of the contact lens.

FIG. 54 shows the individual's natural eyes and FIG. 55 shows the same individual wearing a prosthesis having an aperture widening zone. FIG. 56 is a side by side comparison of FIGS. 54 and 55.

FIGS. 63B and 63C illustrate how to measure the vertical dimension of an aperture widening zone on a prosthesis with an outer edge in the shape of a triangle.

FIGS. 64A-C illustrate various orientations of a prosthesis having an aperture widening zone with an outer edge having an oval shape. FIG. 64A illustrates an orientation having the minimum vertical dimension. FIGS. 64B and 64C illustrate orientations not having the minimum vertical dimension.

DETAILED DESCRIPTION

Figure 1:
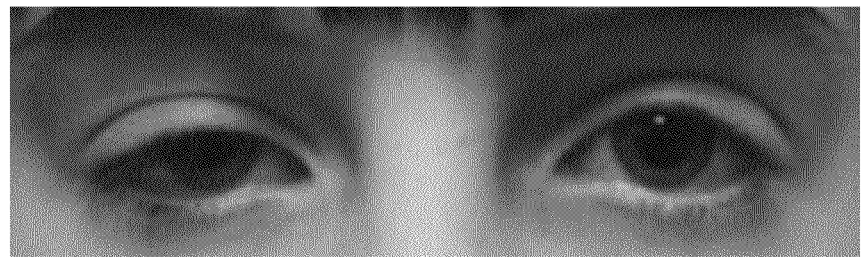
FIG. 1 shows an individual having congenital ptosis on the right eye.

This specification discloses one or more embodiments that incorporate the features of this invention. The disclosed embodiment(s) merely exemplify the invention. The scope of the invention is not limited to the disclosed embodiment(s). Multiple inventions may be described. The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to implement such feature, structure, or characteristic in connection with other embodiments whether or not explicitly described.

Some embodiments include a prosthesis capable of being worn on the eye of a wearer having a convex surface and a concave surface. The prosthesis has an aperture widening zone located on the convex surface. The prosthesis widens the natural palpebral fissure of the wearer's eye by at least 1 mm.

Some embodiments include a prosthesis capable of being worn on the eye of a wearer. The prosthesis has a convex surface and a concave surface. An aperture widening zone is located on the convex surface. The prosthesis is a corneo-scleral contact lens that widens the natural palpebral fissure of the wearer's eye by at least 1 mm.

Some embodiments include a prosthesis having a convex surface and a concave surface. An aperture widening zone is located on the convex surface. The prosthesis is a scleral ring that widens the natural palpebral fissure of the wearer's eye by at least 1 mm.

Some embodiments include a prosthesis capable of being worn on the eye of a wearer. The prosthesis has a convex surface and a concave surface. An aperture widening zone is located on the convex surface. The aperture widening zone includes at least one surface feature. The prosthesis widens the natural palpebral fissure of the wearer's eye by at least 1 mm.

Some embodiments include a prosthesis capable of being worn on the eye of a wearer having a convex surface, a concave surface, and a peripheral edge. The prosthesis also has an aperture widening zone located on the convex surface. The aperture widening zone including an outer slope and an inner slope with a maximum change in thickness located in between. The outer slope and the inner slope are different. In some embodiments the outer slope is greater than the inner slope. In other embodiments the inner slope is greater than the outer slope.

Some embodiments include a prosthesis capable of being worn on the eye of a wearer having a convex surface, a concave surface, and a peripheral edge. The prosthesis also has an aperture widening zone located on the convex surface. The aperture widening zone including an outer slope and an inner slope with a maximum change in thickness located in between. The outer slope and the inner slope are the same.

Some embodiments include a prosthesis capable of being worn on the eye of a wearer. The prosthesis has a convex surface and a concave surface. An aperture widening zone is located on the convex surface. The aperture widening zone has at least one surface feature. The aperture widening zone also has a minimum vertical dimension.

Some embodiments include a prosthesis capable of being worn on the eye of a wearer. The prosthesis has a convex surface, a concave surface, a peripheral edge, and a geometric center. An aperture widening zone is located on the convex surface. The aperture widening zone has at least one surface feature. At least a portion of the at least one surface feature is located at or outside 5.25 mm from the geometric center of the prosthesis.

In some embodiments the prosthesis has an overall diameter of at least 14.0 mm. In other embodiments the prosthesis has an overall diameter of at least 14.5 mm. In some embodiments the prosthesis has an overall diameter of at least 15 mm. In some embodiments the prosthesis has an overall diameter of at least 15.5 mm. In still some other embodiments the prosthesis has an overall diameter of at least 16.0 mm or larger.

In some embodiments the prosthesis is a rotationally symmetric lens. In some embodiments the prosthesis is capable of rotating. In some embodiments the prosthesis is not capable of rotating.

In some embodiments the aperture widening zone depresses a lower eye lid of the wearer by at least 1 mm. In some embodiments the aperture widening zone elevates an upper eye lid of the wearer by at least 1 mm.

In some embodiments the prosthesis includes a colored accent color. In some embodiments the colored accent color is around a portion of the prosthesis which fits near or at the limbus, or extends past the limbus (meaning the diameter of the colored portion is larger than the diameter of the limbus to limbus measurement) of the eye when the prosthesis is worn. In some embodiments the colored accent color is a limbal ring, circle ring, or circle lens.

In some embodiments the prosthesis is a multifocal contact lens. In some embodiments the prosthesis is a toric contact lens. In some embodiments the prosthesis is a single vision contact lens.

In some embodiments the aperture widening zone comprises an area of increased surface friction. In some embodiments the increased surface friction is provided by a surface treatment, a coating, a different material, surface dimples, surface irregularities, or combinations thereof In some embodiments the aperture widening zone also includes an outer slope and an inner slope with a maximum change in thickness located in between. In some embodiments the outer slope and inner slope are different. In some embodiments the outer slope is greater than the inner slope. In some embodiments the outer slope has an angle between 3° and 45°. In some embodiments the outer slope has an angle between 5° and 25°. In some embodiments the inner slope comprises an angle between 1° and 15°.

In some embodiments the aperture widening zone has an incremental thickness and a maximum change in thickness. In some embodiments the maximum change in thickness is within a range of 25 microns to 1,000 microns. In some embodiments the maximum change in thickness is within a range of 100 microns to 500 microns. In some embodiments the maximum change in thickness is within a range of 75 microns to 400 microns. In some embodiments the maximum change in thickness is located between 1.0 mm and 2.5 mm from an outer edge of the prosthesis. In some embodiments the maximum change in thickness is located at or exterior to the corneal limbus of the wearer's eye when the prosthesis is worn on the eye. By exterior it is meant that the maximum change in thickness diameter when measuring from one point of maximum added thickness thru the geometrical center of the prosthesis to an opposing point of maximum added thickness is larger than when measuring from one point on the limbus of the wearer's eye thru the center of the cornea to an opposing point on the limbus. In some embodiments the incremental thickness is an increase in thickness. In some embodiments the incremental thickness is a decrease in thickness.

In some embodiments an outermost part of the aperture widening zone is located within a range of 3 mm to 8.5 mm from a geometric center of the prosthesis. In some embodiments an outermost part of the aperture widening zone is located within a range of 5 mm to 7.75 mm from a geometric center of the prosthesis. In some embodiments an innermost part of the aperture widening zone is located between a peripheral edge of the prosthesis and 6 mm from a peripheral edge of the prosthesis.

In some embodiments a minimum vertical dimension of the aperture widening zone is larger than a maximum vertical diameter of the natural palpebral fissure of the wearer's eye. In some embodiments a minimum vertical dimension of the aperture widening zone is equal to or greater than 10.5 mm. In some embodiments a minimum vertical dimension of the aperture widening zone is equal to or greater than 11 mm. In some embodiments a minimum vertical dimension of the aperture widening zone is equal to or greater than 11.5 mm. In some embodiments a minimum vertical dimension of the aperture widening zone is equal to or greater than 12 mm. In some embodiments a minimum vertical dimension of the aperture widening zone is a vertical distance between an uppermost part of the aperture widening zone and a lowermost part of the aperture widening zone.

In some embodiments the aperture widening zone includes at least one surface feature. In some embodiments the aperture widening zone has a plurality of surface features.

In some embodiments the prosthesis is a corneo-scleral contact lens. In some embodiments the prosthesis is a scleral ring.

In some embodiments the aperture widening zone has a minimum vertical dimension.

In some embodiments the prosthesis also has a peripheral edge, a geometric center, and at least one surface feature. In some embodiments the at least one surface feature or at least a portion of the at least one surface is located at or outside 5.25 mm from the geometric center of the prosthesis. In some embodiments the peripheral edge has a knife edge shape, a rounded shape, a blunt shape, or a semi-rounded shape. In some embodiments the peripheral edge has a thickness between 25 microns and 100 microns.

In some embodiments the prosthesis has a hybrid design. In some embodiments the prosthesis has a homogeneous design.

In some embodiments the aperture widening zone comprises a ring, multiple rings, a partial ring, multiple partial rings, an island, multiple islands, a band, bands, partial bands, a segmented area, or multiple segmented areas. In some embodiments these partial areas are aligned to ring the prosthesis. In other embodiments these partial areas are not aligned to ring the prosthesis.

In some embodiments the prosthesis can be worn by the wearer continuously. In some embodiments the prosthesis can be worn by the wearer non-continuously. In some embodiments the prosthesis can be worn by the wearer daily, weekly, or monthly.

In some embodiments the prosthesis is disposable. In some embodiments the prosthesis is reusable.

In some embodiments the prosthesis comprises an optical power. In some embodiments the prosthesis does not comprise an optical power.

Some embodiments include a prosthesis having an aperture widening zone. The aperture widening zone has an outer slope, an inner slope, a point of maximum added thickness delta, and an incremental thickness diameter. The prosthesis also has a peripheral edge, a geometrical center, and an overall diameter. The overall diameter is measured from a first point on the peripheral edge to a second point on the opposing peripheral edge thru the geometrical center of the prosthesis and the aperture widening zone. The overall diameter is 14.5 mm or greater. The outer slope is with the range of 5 degrees and 25 degrees. The point of maximum added thickness delta of the aperture widening zone is 75 microns or greater. The point of maximum added thickness delta of the aperture widening zone is located between 1 mm and 3 mm from the peripheral edge. The incremental thickness diameter is 10.5 mm or greater.

In some embodiments the prosthesis is free to rotate. In some embodiments the prosthesis is not free to rotate.

In some embodiments the incremental thickness diameter is 1 mm larger than the vertical measurement of the natural aperture of the wearer's eye.

In some embodiments the prosthesis is a corneo-scleral lens. In some embodiments the prosthesis is a scleral ring.

In some embodiments the prosthesis has optical power. In some embodiments the prosthesis does not have optical power.

In some embodiments the prosthesis is a single vision contact lens. In some embodiments the prosthesis is a multifocal contact lens. In some embodiments the prosthesis is a toric contact lens.

In some embodiments the prosthesis includes a hydrogel. In some embodiments the prosthesis includes a silicone hydrogel. In some embodiments the prosthesis includes a homogenous material. In some embodiments the prosthesis includes hybrid materials.

In some embodiments the aperture widening zone begins at or adjacent to the peripheral edge. In some embodiments the aperture widening zone begins internal to the peripheral edge.

In some embodiments the point of maximum added thickness delta is 100 microns or greater. In some embodiments the point of maximum added thickness delta is 125 microns or greater. In some embodiments the point of maximum added thickness delta is 150 microns or greater. In some embodiments the point of maximum added thickness delta is 200 microns or greater. In some embodiments the point of maximum added thickness delta is 225 microns or greater. In some embodiments the point of maximum added thickness delta is 250 microns or greater.

In some embodiments the prosthesis is one of: daily wear, disposable, continuous wear, weekly wear, or monthly wear.

In some embodiments the prosthesis is not stabilized.

In some embodiments the aperture widening zone is a round ring. In some embodiments the aperture widening zone is a series of partial segments that make up a ring.

Some embodiments provide for a method of widening the natural palpebral fissure of a wearer's eye by providing a protocol or instructions for widening the wearer's natural palpebral fissure by at least 1 mm and providing at least one prosthesis comprising an aperture widening zone located on its convex surface. In some embodiments the protocol or instructions include directions to determine a vertical dimension of the wearer's natural palpebral fissure, and to provide the wearer with a prosthesis having a minimum vertical dimension at least 1 mm greater than a maximum vertical dimension of the natural palpebral fissure (such a determination can be made by, way of example only, actual measurement, photography, visual estimate, or by one of; fitting a trial prosthesis, contact lens of a known diameter, or a prosthesis of a known diameter).

A prosthesis of this patent application in the form of a corneo-scleral contact lens and a scleral ring has been developed that enhances/widens the palpebral fissure of a wearer's eye to enhance the cosmetic appearance of the wearer's eye (eyes) and can also be used to provide relief to patients suffering from drooping eyelids and/or ptosis. By enhancing the appearance of the wearer's eye it is meant that it makes the eye look more open and/or larger, and more alert. The novel prosthesis enhances the cosmetic appearance of the wearer by way of pushing up (elevating) the upper eyelid and/or also pushing down (depressing) the lower eyelid thus enlarging the wearer's palpebral fissure or aperture. The prosthesis has been shown to open the aperture of a wearer's eye by up to an additional 50% from its normal/natural eye aperture vertical dimension. Given that the average aperture of an individual's eye under the age of 40 would have a natural aperture having a vertical dimension (between the upper lid margin and the lower lid margin) of approximately 10.5 mm and that after the age of 40 the average dimension from the same points is approximately 9 mm, or approximately a 15% reduction in aperture size it can be seen that the prosthesis described herein can restore the youthful look of the wearer's eyes.

The prosthesis comprises one or more, by way of example of: an augmentation in edge thickness, an internal incremental thickness zone, a regressive thickness zone, or an increased surface friction zone (either one) located at or external to the limbus, thus also external to the pupillary or optic zone which takes the form on the convex surface, by way of example only, of one or more of; a ring, (rings) band, (bands), partial rings (ringlets), dome (domes), island (islands), segmented region (regions), convex surface roughness/friction near or around the periphery of the lens and/or within or covering the aperture widening zone, truncation (truncations), overall thickening of the contact lens, larger diameter, and steeper base curve. The effect is to open up the palpebral fissure of the eye of the wearer and thus minimize the impact of blepharoptosis on visual performance and enhance the cosmetic appearance of the patient/wearer. The prosthesis when in the form of a corneo-scleral contact lens can be that of a soft contact lens or hybrid contact lens. When the prosthesis is in the form of a scleral ring as opposed to a contact lens the scleral ring comprises a central open aperture without optical power. The scleral ring can be made of a material found in one of a: hard contact lens, gas perm contact lens, soft contact lens; hybrid contact lens. The incremental thickness region (zone, area) or a regressive thickness region (zone, area), or increased surface friction region (zone, area) for the prosthesis (being a contact lens or a scleral ring) can be one of: rotationally symmetric, rotationally asymmetric, elliptical arch like feature, and isolated islands. The elliptical arch (arches) like feature (features) can resemble the curve of the lid margin of the upper lid and/or the curve of the lid margin of the lower lid. The region of incremental thickness, or regressive thickness, or increased surface friction can be either continuous or discontinuous. The incremental thickness region, regressive thickness region, or increased surface friction can be made of the same material or different materials. The prosthesis can be worn as one of: continuous wear, daily wear weekly continuous wear, or monthly continuous wear. The prosthesis can be disposable or reusable. The prosthesis can be removed and reinserted by the wearer.

Aperture of the eye (Palpebral Fissure): Is the area located between an eye's upper lid and the lower lid when the eye lids are open.

Aperture Widening Zone: (Also can be called one or more of an incremental thickness region/zone/area, a regressive thickness region/zone/area or an increased surface friction region/zone/area). Is a region, zone, area that provides topography, or surface friction that raises (elevates) the upper lid and/or depresses (lowers) the lower lid thus widening the aperture of the eye.

Area of incremental thickness: The area located within the region or zone of incremental thickness of the scleral ring or contact lens. Should (by way of example only) the region or zone of incremental thickness be a plurality of regions or zones the area of incremental thickness would be referred to as areas of incremental thickness. It should be noted that an area of incremental thickness can be formed either by way of adding thickness to the surface or by removing thickness around the area of incremental thickness (thus by a regressive thickness zone).

Blepharoptosis: also referred to as ptosis, is defined as an abnormal low-lying upper eyelid margin with the eye in primary gaze. The normal adult upper lid lies 1.5 mm below the superior corneal limbus and is highest just nasal to the pupil. Blepharoptosis can be classified as congenital, as shown below, or acquired. This differentiation is based on age. A more comprehensive classification is based on etiology and includes myogenic, aponeurotic, neurogenic, mechanical, traumatic, and pseudoptotic. The most common cause of congenital ptosis is myogenic due to the improper development of the levator muscle Blepharoplasty is the name of the surgical procedure that provides for lid lifting. Presently there are approximately 200,000-300,000 blepharoplasty operations performed per year in the United States at the cost of approximately $2,500 per upper lids surgery and $3,500 per lower lids surgery. Blepharoplasty is one of the top facial cosmetic surgical procedures performed for those over the age of 40. In addition, it should also be noted that big eyes are perceived to be more attractive than small eyes in today's global society Centration of scleral ring or contact lens: As used herein is meant to be the proper centering of the scleral ring or contact lens so that the wearer's limbus and/or pupil is mostly centered within the open aperture of the scleral ring or in the case of a contact lens the wearer's pupil is mostly centered within the optic zone.

Central Open Aperture: Means a hole or opening devoid of material that includes the geometrical center of the prosthesis.

Contact Lens: Is a thin lens designed to fit over the cornea and usually worn to correct defects in vision. Contact lenses generally fall into three major categories: #1) corneal contact lens, #2) Corneo-scleral contact lens, #3) Scleral contact lens. The three major categories can then be further broken down into sub categories (by way of example only) A) daily wear (meaning only used daily for wearing and taking out when sleeping), B) continuous wear (meaning wearing day and night round the clock for a limited number of days, and C) disposable contact lenses which can be worn either daily or continuously, but are discarded when they become dirty or lose certain optical or comfort qualities. (It is important to note that the prosthesis being disclosed herein is that of category #2 (corneo-scleral contact lens) therefore when the term contact lens is used it is meant to be that of a corneo-scleral contact lens).

Corneal contact lens: Corneal lenses are supported exclusively by the cornea, and do not extend past the limbus (the junction between the cornea and the sclera). An example of a corneal contact lens would be a hard rigid contact lens having a diameter no larger than the diameter of the wearer's cornea and in most cases smaller than the diameter of the wearer's cornea. Corneal contact lenses can also be soft contact lens.

Corneo-scleral lenses: Corneo-scleral lenses are a type of contact lens used to correct defects in vision. The name refers to the area and resting points of the lens in the eye. Corneo-scleral lenses are supported by both the cornea and bulbar conjunctiva that is above the sclera, and do extend past the limbus. Examples of corneo-scleral contact lens would be: soft contact lens and hybrid contact lens. These lenses have a diameter in excess of the diameter of the wearer's cornea and extend past the wearer's limbal area. They range generally (but not always) from 12.5 to 15 mm in diameter. The tear reservoir underneath a corneo-scleral lens is very limited compared to full scleral contact lenses that vault the cornea. Corneo-scleral lenses are the most common used.

Delta Incremental Thickness, Incremental Thickness Delta, Delta of Incremental Thickness, and Maximum Change in Thickness: Is the difference in thickness between a point located within the incremental thickness region and the normal thickness of the contact lens or scleral ring measured at the same point. The maximum delta is the point where the thickness differential or maximum delta thickness is the greatest or said another way, the point where the maximum change in thickness is found.

Delta Regressive Thickness, Regressive Thickness Delta, Delta of Regressive Thickness, and Maximum Change in Thickness: Is the difference in thickness between a point located within the regressive thickness region compared to a thickness of a near (closely located) area of the contact lens or scleral ring internal (on the side towards the center of the prosthesis). The maximum delta is the point where the thickness differential or maximum delta thickness is the greatest, or said another way, the point where the maximum change in thickness is found.

Edge: The edge of the contact lens or scleral ring as used herein is the outer peripheral circumference of the contact lens or in the case of a scleral ring, either the outer peripheral edge or inner peripheral edge closest to the open aperture of the scleral ring. The inner edge of a scleral ring (adjacent to the open center aperture) has a similar contour as that of the outer edge of the scleral ring.

Gas perm contact lens: Is a contact lens comprising a rigid material that is permeable to oxygen; such a material is used in gas perm corneal contact lenses that are of a diameter equal to or less than the diameter of the wearer's cornea or in the central rigid gas permeable region of a hybrid contact lens whereby the material which is central to that of a soft hydrophilic skirt is of a gas permeable material.

Geometrical Center: Geometrical center as used herein is meant to be the absolute center of a scleral ring or contact lens. In the case of a contact lens it is real; in the case of a scleral ring it is imaginary given the central open aperture.

Hybrid Contact Lens or Hybrid Scleral Ring: A hybrid contact lens as used herein is a contact lens or scleral ring comprised of two or more materials bonded together. An example of this would be like that of today's commercially available hybrid contact lens comprising a central gas permeable material and an outer soft hydrophilic contact lens skirt. Three additional embodiments discussed herein are: #1) An embodiment taught herein whereby the outer periphery of the hybrid contact lens is rigid and the center is soft or #2) In the case of a scleral ring, a ring that rests over the sclera being of a more rigid (less soft or more rigid) material, however, having affixed to the scleral ring, a softer more pliable material that forms part or all of the incremental thickness zone that provides the widening effect. This softer more pliable material can be in the form of finger like members that extend away from the more rigid scleral ring. #3) In the case of a soft contact lens having a member or surface treatment which is not of the same material that provides increased surface friction such to raise the upper lid and/or lower the lower lid.

Incremental Thickness: Is that of the increased differential or delta thickness when taking a point on the base scleral ring or contact lens of a normalized convex surface calculating the differential from that point to that of the same point on the scleral ring or contact lens taught herein. Said another way; after mathematically normalizing the convex surface curvature of the scleral ring or contact lens, is the additional thickness added over and beyond the normalized convex surface of the scleral ring or contact lens. It is important to note for a contact lens the convex surface of the optic zone is not considered in the calculation of the normalized convex surface and thus excluded, as the optic zone may have a different convex curvature due to the specific optical power of the contact lens. The maximum incremental thickness is the peak thickness delta or the maximum change in thickness. It is important to note that incremental thickness can be created by being surrounded or adjacent to a regressive thickness region.

Incremental Thickness Diameter: The incremental thickness diameter is the distance along the vertical axis from a point of maximum delta thickness or maximum change in thickness proceeding through the geometrical center of the prosthesis in a straight line to that of a point of maximum delta thickness or maximum change in thickness located on the opposite side from the previous point of maximum delta thickness.

Incremental Thickness Region/Zone/Area: (also is referred to as an "Aperture Widening Zone") is a phrase coined for the purposes of this patent application. Incremental thickness zone is the additional thickness of a zone, region, area that is added over and beyond the normalized convex surface of the contact lens or scleral ring. The incremental thickness zone can also be made up of a plurality of zones or regions of incremental thickness and can be further broken into an area or areas of incremental thickness. In most, but not all cases, the incremental thickness zone or region provides no useful vision correction for the wearer. The incremental thickness zone is also called the aperture widening zone. The purpose of the incremental thickness region or zone is that of providing a force against the upper lid (lids) to lift (elevate) and/or the lower lid to lower (depress) such to widen the eye's palpebral fissure (aperture) of the wearer.

Incremental Thickness Zone Width: Is the width measurement on the convex surface of the scleral ring or contact lens where the incremental thickness zone begins and ends. This is the width of the incremental thickness zone usually measured from the portion closest to the outer edge of the prosthesis to the portion closest to that of the geometrical center of the prosthesis Inner Slope: The "inner" slope is the slope of the aperture widening zone between the point of maximum thickness delta and where the aperture widening zone ends closest to the geometrical center of the prosthesis.

Junction: Junction as used herein is meant to be the location of a conventional hybrid contact lens where the gas permeable central region's outer peripheral edge meets the inner peripheral edge of the outer soft skirt or in the case of a hybrid scleral ring or a reverse hybrid lens is the location of where the two different materials meet.

Limbus: The marginal region of the cornea of the eye by which it is adjacent with the sclera. The average diameter of the cornea is approximately 11-12 mm and normally recognized to be approximately 11.5 mm on average.

Minimum Vertical Dimension: Is one way to measure and/or quantify structural features of a prosthesis with an aperture widening zone. Minimum vertical dimension is a parameter used to quantify some, but not necessarily all, embodiments described here. "Vertical dimension" is the vertical distance between the highest part of an aperture widening zone near the top of the prosthesis, and the lowest part of an aperture widening zone near the bottom of the prosthesis. In other words, the "vertical dimension" defines the vertical distance between the uppermost part of the prosthesis that pushes the upper eyelid up, and the lowermost part of the prosthesis that pushes the lower eyelid down. Where the aperture widening zone starts at the edge of the prosthesis, the "vertical dimension" of the aperture widening zone corresponds to the vertical size (overall diameter) of the prosthesis. If the highest and lowest parts do not lie on the same vertical axis, then the "vertical dimension" is the distance between a projection of the highest and lowest points onto a vertical axis. If the aperture widening zone is not rotationally symmetric, the vertical distance may change as the prosthesis is rotated. The "minimum vertical dimension" is the vertical dimension that corresponds to the rotational position(s) of the prosthesis that has the smallest vertical dimension. Pressure from the eye lids will, in many cases, tend to rotate the prosthesis into this rotational position.

Multifocal Contact Lens: Is a contact lens comprised of two or more optical power regions. Such a contact lens is used to correct presbyopia as well as at a minimum the wearer's distance vision. Some multifocal contact lenses will correct distance, intermediate and near vision of the wearer.

Natural Palpebral Fissure (Natural Aperture): The space between the margins of the eyelids—called also rima palpebrarum. The natural palpebral fissure is the space or area of the palpebral fissure when not wearing a contact lens, when the eye or eyes are relaxed and while the individual is expressionless and not squinting, smiling or frowning etc.

Normalized Front Convex Surface: Is meant to mean a front convex surface without any incremental thickness added to that of a normal front convex surface of a contact lens or scleral ring. The normal front convex surface can be that of a non-spherical convex curvature or a spherical convex curvature. In most, but not all, cases the normalized front surface is that of a spherical curvature. Said another way the normalized front convex curvature equals the convex curvature minus the incremental thickness added. When normalizing the convex surface of a contact lens the normalized surface does not take into account the convex surface of the optic zone as the optic zone may have a different curvature influenced by the optical power of the contact lens.

Optic Zone: Is the central zone of the contact lens that comprises optical power. The optic zone is of a fixed size and in a fixed location within the contact lens. In the disclosure contained herein the term optic zone and optical zone are meant to mean the same. Generally the optic zone of soft contact lenses ranges between 7 mm to 9 mm in diameter. The optic zone diameter is generally larger than the pupillary zone diameter to prevent glare and light scatter when the pupil dilates at night. The scleral ring does not have an optic zone, but rather an open aperture.

Overall Outer Diameter: The diameter measured from the outer edge of the prosthesis across the prosthesis through the geometrical center to the opposing outer edge.

Outer Slope: The "outer" slope is the slope of the aperture widening zone between the point of maximum thickness delta and where the aperture widening zone ends closest to the outer edge of the prosthesis.

Overall Thickness: The thickness when measured at a point on the concave surface of the contact lens or scleral ring to a point on the outside convex surface at the same point relative to one another.

Peak Thickness Delta (Maximum Thickness Delta): Is the maximum incremental thickness (added) or the maximum regressive thickness (reduced). Said another way is the maximum change in thickness.

Prosthesis: A device worn by a wearer that provides a benefit for the wearer. In the case of the disclosure disclosed herein the benefit can be that of a cosmetic benefit or a vision benefit.

Ptosis: A drooping of the upper eyelid caused by way of example only: from paralysis of the oculomotor nerve. Ptosis refers to abnormal drooping of the upper eyelid which can affect one or both the eyes. It may be constant or intermittent in nature. Ptosis can be congenital, if present since birth, or it may be acquired when it develops later in life. Usually ptosis occurs as an isolated disorder but may also be associated with various other conditions. Ptosis may afflict both children and the adult population. Incidence of ptosis has been reported to be 0.18% in children, but occurs more frequently in older adults, probably due to the aging factor, and may affect up to 1% of the population or more. Both men and women are equally susceptible to ptosis.

The most common feature of ptosis is drooping of the upper eyelid of the affected eye. Depending on the severity of drooping, it is categorized into: minimal (1-2 mm), moderate (3-4 mm) and severe (>4 mm). Individuals with ptosis may complain of increased tearing and blurred vision. Patients with significant ptosis may need to lift the eyelid with a finger, or raise their eyebrows for normal straight vision and this may lead to tension headaches and eyestrain.

Ptosis occurs when the muscles that raise the eyelid (levator and Muller's muscles) are not strong enough to do so properly. It can affect one eye or both eyes and is more common in the elderly, as muscles in the eyelids may begin to deteriorate. Ptosis usually results due to failure of eyelid muscles to function properly. This may occur due to localized damage to eyelid muscles or damage to nerves supplying the eyelid muscles. It may also occur as a normal aging process. Individuals with diseases like Myasthenia gravis, Diabetes mellitus, stroke, Horner's syndrome and brain tumor are at increased risk of acquiring ptosis. In fact myasthenia gravis, which is a neuromuscular disorder, is one of the common causes of acquired ptosis. It has also been reported that long term wearers of contact lenses may develop ptosis and also those who use Botox for cosmetic treatment of appearance. If left untreated, especially in children, ptosis may lead to a complication called 'Lazy Eye' where the child cannot see properly with one of his or her eyes. This condition can be reversed if treated properly. There may be emotional disturbances in children due to visual defect and physical disfigurement.

Figure 2:
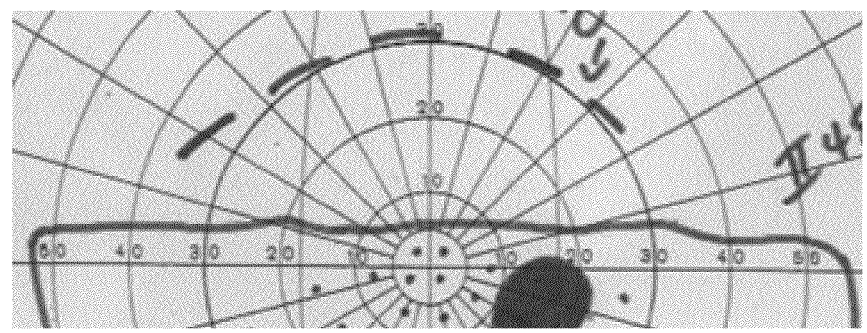
FIG. 2 illustrates a visual field that shows functional blockage due to a ptotic lid.
Figure 3:
FIGS. 3-7 illustrate various individuals afflicted by ptosis.
Figure 4:
Figure 5:
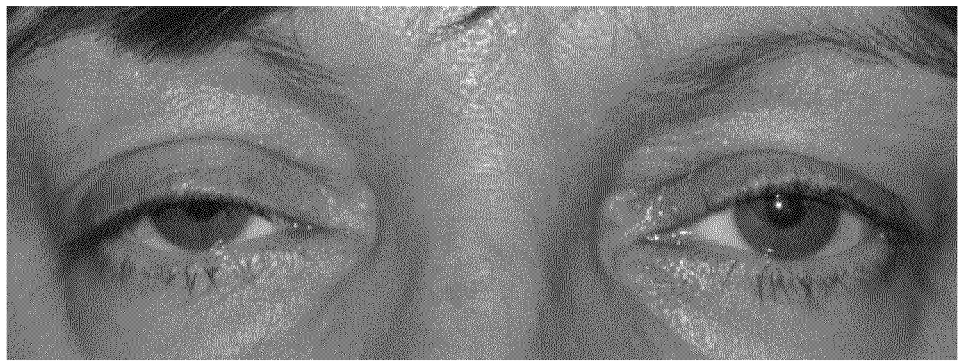
Figure 6:
Figure 7:
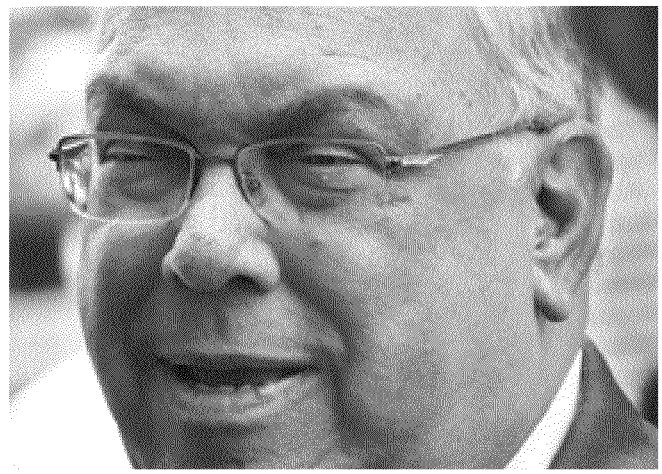
Figure 8:
FIGS. 8-11 illustrate various individuals with wide eyes that are not afflicted by ptosis.
Figure 9:
Figure 10:
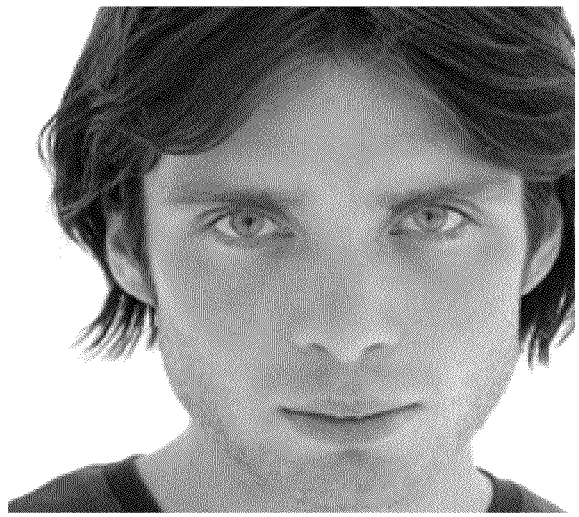
Figure 11:
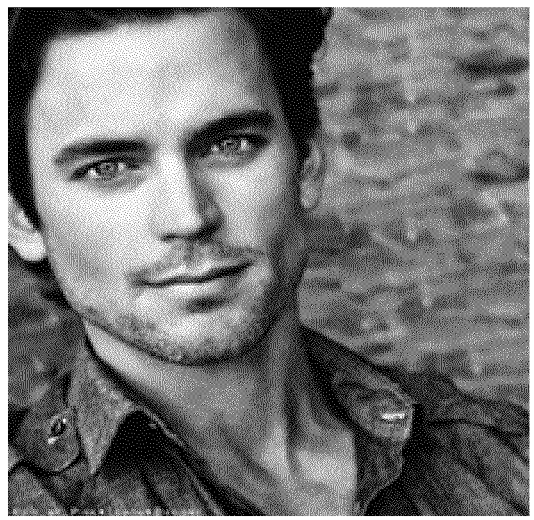

Regular monitoring of the condition is required in cases of mild ptosis, where no visual impairment is present. However, significant congenital ptosis may warrant surgical intervention which includes expertise of an eye specialist and a plastic surgeon. Surgical modalities include correction of eyelid muscles and procedures like Levator resection, Muller muscle resection or *Frontalis* sling operations are generally performed. Non-surgical modalities like use of Crunch glasses or special Scleral contact lenses are also popular nowadays. FIG. 1 shows an individual with congenital ptosis on the left eye. FIG. 2 illustrates a visual field that shows the functional blockage due to a ptotic lid. Ptosis can affect the visual field of the wearer's eye thus limiting the area of functional vision. If the ptosis is of the upper lid and whereby the upper lid covers a portion of the pupil the individual having the ptosis will lose the ability to see in a portion of his or her superior visual field. FIGS. 3-7 show four individuals afflicted with ptosis. Ptosis can afflict all ages with the highest incidence in those over the age of 40.

Pupillary Zone: As used herein is the zone of a contact lens when worn by a wearer, whereby the wearer's pupil would be in optical communication with (or said another way where the pupil of the wearer's eye would receive light through). The pupillary zone is of a larger area at night or dim illumination when the pupil is dilated and of a smaller area in higher levels of ambient light. The pupillary zone of the prosthesis described herein generally ranges from approximately 6 mm in diameter to 8 mm in diameter (or a radius of 3 mm to 4 mm from the geometrical center of the contact lens) in order to cover the pupil when the pupil dilates due to a low level of ambient light. The pupillary zone is generally smaller than the contact lens optic zone, or optical zone. The pupillary zone is located within the scleral ring central open aperture.

Piggy Back: The term "piggyback" or piggybacking is that of: of a smaller, rigid contact lens on the surface of a larger, soft contact lens. These techniques give the vision corrections benefits of a rigid lens and the comfort benefits of a soft lens. The term can also apply to two or more soft contact lenses being worn simultaneously.

Region: The terms region, zone, area all have the same meaning in this disclosure.

Regressive Thickness: Is a reduction of thickness.

Regressive Thickness Diameter: The incremental thickness diameter is the distance along the vertical axis from a point of maximum delta thickness proceeding through the geometrical center of the prosthesis in a straight line to that of a point of maximum delta thickness located on the opposite side from the previous point of maximum delta thickness.

Regressive thickness region: (Also referred to as an "Aperture Widening Zone") is a region whereby the normalized thickness of the prosthesis is reduced such to form by way of example only, a "valley" like area, region, zone of topography on the convex surface of the prosthesis or a "partial" valley like area, region, zone whereby one side increases in thickness and the other side maintains the same thickness or decreases further in thickness. A regressive thickness region generally (but not always) results in an incremental thickness region.

Regressive Thickness Zone Width: Is the width measurement on the convex surface of the scleral ring or contact lens where the regressive thickness zone begins and ends. It is generally (but not always) measured from where it starts closest to the outer edge of the prosthesis to where it ends on the side closer to the geometrical center of the prosthesis.

Reverse Hybrid Contact Lens: This is a hybrid prosthesis whereby the outer skirt is made of a rigid material and the center zone is made of a soft lens material.

Rigid Center: Rigid center is meant to be the area of a contact lens; conventional gas perm or hybrid gas perm being made of a rigid material.

Ring: The term ring as used herein can be that of a continuous ring or a discontinuous ring. Thus a ring of incremental thickness can be one that is a continuous ring or a broken discontinuous ring. A ring can also be called one of a band (bands), zone (zones), island (islands), region (regions), and segment (segments) that rings the prosthesis either continuously or discontinuously.

Sclera: The whitish covering of the eye which joins the cornea at the limbus and is covered in certain regions of the eye by the bulbar conjuctiva.

Scleral Ring Eye Enhancer (scleral ring): A prosthesis device which fits over the sclera of the eye of a wearer, has a topography (aperture widening zone) located on its convex outer surface that provides for widening of the palpebral fissure of the wearer and comprises an open central aperture such to not interfere with the line of sight of the wearer. A scleral ring can comprise one material (homogenous) or multiple materials in the case of a hybrid scleral ring. A hybrid scleral ring can comprise finger like members that lift the upper lid and/or lower the lower lid. The scleral ring does not comprise optical power. In most, but not all cases, the scleral ring does not cover parts of the cornea. However, in some embodiments the scleral ring will cover the limbus and a very limited peripheral region of the cornea.

Scleral Contact lens: A scleral lens is a specially designed large-diameter "rigid" contact lens that vaults the cornea (meaning it does not rest on the cornea). They can range from 14 mm to over 20 mm in diameter. They are called "scleral" lenses because they completely cover and vault the cornea (the clear dome of tissue that covers the colored part of the eye) and extend onto the sclera (the white part of the eye that forms the outer wall of the eye). Scleral lenses are supported exclusively by the sclera, and completely vault the cornea and the limbus. Scleral lens fit very tightly on the sclera of the wearer's eye.

Silicone Hydrogel: Is a material used for soft contact lenses. In 1998, silicone hydrogels became available. Silicone hydrogels have both the extremely high oxygen permeability of silicone and the comfort and clinical performance of the conventional hydrogels. Because silicone allows more oxygen permeability than water, the oxygen permeability of silicone hydrogels is not tied to the water content of the lens. Lenses have now been developed with so much oxygen permeability that they are approved for overnight wear (extended wear). Lenses approved for daily wear are also available in silicone hydrogel material.

Disadvantages of silicone hydrogels are that they are slightly stiffer and the lens surface can be hydrophobic and less "wet-able." These factors can influence the comfort of the lens. New manufacturing techniques and changes to multi-purpose solutions have minimized these effects. A surface modification processes called plasma coating alters the hydrophobic nature of the lens surface. Another technique incorporates internal rewetting agents to make the lens surface hydrophilic. A third process uses longer backbone polymer chains that result in less cross linking and increased wetting without surface alterations or additive agents.

Single Vision Contact Lens: A contact lens comprising a single optical power. The optical power can be to correct one or more of: hyperopia, myopia, and astigmatism.

Slide Resistance: The resistance imparted between the lid (lids) and the contact lens as the lid (lids) blink and move across the contact lens or scleral ring.

Slope: Is the curvature or topography of an external surface. More specifically the slope in this disclosure is characterized as the degree of incline or decline of the aperture widening zone, region or area. The slope is characterized by the outer slope and the inner slope.

Soft skirt: Soft skirt is the outer circular zone of soft hydrophilic material found located on a hybrid contact lens or scleral ring.

Soft Contact Lens: While rigid lenses have been around for about 120 years, soft lenses are a much more recent development. The principal breakthrough in soft lenses made by Otto Wichterle led to the launch of the first soft hydrogel lenses in some countries in the 1960s and the approval of the "Soflens" daily material (polymacon) by the United States FDA in 1971. Soft contact lenses are immediately comfortable, while rigid contact lenses require a period of adaptation before full comfort is achieved. The biggest improvements to soft lens polymers have been increasing oxygen permeability, lens wettability, and overall comfort.

Stabilization zone: A region, zone, area that stabilizes the prosthesis such as by way of example only; co-axial stabilization zones, truncation, prism ballast, slab off, and weighted. A stabilization zone will substantially reduce or stop rotation of the prosthesis when in the eye upon lid blinks. The stabilization zone generally touches the lid margins to prevent the lens from rotating. Stabilization zones or features can cause a reduction in oxygen transmission by a soft contact lens to the wearer's cornea.

Surface Feature: a feature located on the surface of the prosthesis that is different from the rest of the prosthesis. This feature can be, by way of example only, an increased/decreased thickness, increased surface friction, a region made of a different material, dimples, bumps, surfaces irregularities, any change in surface topography, and any combination thereof Surface Friction or Increased Surface Friction: Means a surface area, zone, region of the convex surface of the prosthesis which provides for an increased surface friction when contacted by the eye lids of the wearer of the prosthesis. This area on the convex surface of the prosthesis can be located on the aperture widening zone. This area or zone can be provided on the surface of the zone or region of incremental thickness or in place of the zone or region of incremental thickness. An increased surface friction region, zone, area can be flat or raised.

Thickness Region or Zone: The region or zone of the contact lens where the incremental thickness is added to that of a base contact lens. This region or zone is where thickness is added to the convex external surface. It can also be referred to as the incremental thickness zone.

Thickness differential: Is a region, zone, area of the prosthesis whereby a first point is thinner than a second point which is adjacent to the first point. In most cases (not all) this thickness differential is gradual and not a step function resulting in a discontinuity. Thickness differential can be found on the prosthesis in the region of incremental thickness, or a regressive thickness region.

Thickness Slope: The measured thickness per traveled mm along a horizontal axis of a surface topography having an incline or decline. The thickness slope can be calculated using incremental thickness or regressive thickness, and also by way of the overall thickness. The thickness slope can be located at the outer thickness slope region or the inner thickness slope region both of which are associated with the aperture widening zone.

Toric Contact Lens: Is a contact lens that is comprised of a toric region or zone that corrects for an astigmatic error of the wearer. A toric lens of this type can be a cylindrical corrective power or a sphero-cylindrical optical power.

Vertical Dimension: Is the distance between the highest and lowest points of the aperture widening zone projected onto a vertical axis. If the aperture widening zone is not symmetrical in nature the vertical dimension may vary as the lens rotates, i.e. the vertical dimension is a function of the rotational position of the lens.

FIGS. 8-11 are examples of eyes that should be excluded from the patient population being fit with the contact lens being taught herein. It should be noted that the upper lids of the individuals in FIGS. 8-11 do not come within 2 mm of the upper edge of the pupil or the lower lid does not come within 2 mm of the lower edge of the pupil.

As discussed above scleral hard/rigid contact lenses designed to lift the upper lid have been a major failure in the market place due to the significant discomfort associated with such a lens when the wearer normally blinks his or her lids. In addition, the cosmetics of the eye when wearing such a scleral contact lens is not pleasing for the wearer. For all practical purposes such sclera contact lenses designed for correcting ptosis have largely ceased being commercial since the 1980s. Rigid corneal contact lenses that fit only on the cornea are not capable of lifting the lid of a wearer as the lid will push the contact lens off center.

Conventional corneo-scleral contact lenses (those most popular in the world today) (prior to the corneo-scleral contact lenses taught herein) due to their geometrical design have not been capable of lifting the lids or opening the palpebral fissures of a plurality of corneo-scleral contact lens wearers. Corneo-scleral contact lenses provide a plurality of different optical corrections. The use of a the phrase a "plurality of different optical corrections or prescriptions" is meant to be the optical power or prescription of wearers of corneo-scleral contact lenses being of plano (no optical power) and also mostly all known optical prescriptions or optical powers provided by contact lenses.

Thus there is an unmet need for a prosthesis in the form of a corneo-scleral contact lens (soft contact lens and/or hybrid contact lens) capable of being designed to provide mostly any and all known optical powers including plano, a high level of comfort, good centration, and excellent nourishment that will lift the upper lid (in the case of a ptosis) and/or lower the lower lid of the wearer thus widening the wearer's palpebral fissure (or fissures/apertures when wearing two such contact lenses; one for the right eye and one for the left eye).

In addition, there is a pressing need for a prosthesis which widens the palpebral fissure (aperture) of the eye for a "non-wearer" of contact lenses. Such a prosthesis is described herein as another embodiment in the form of a scleral ring. A scleral ring is not intended to be a contact lens. A scleral ring does not comprise an optic zone or any optical power. The central region of a scleral ring is that of a central open aperture. However, the scleral ring as taught herein comprises an aperture widening zone that widens the palpebral fissure or eye aperture of the wearer.

It should be pointed out that when the term "contact lens" is used herein, unless mentioned as that of one of a scleral contact lens, a gas perm corneal contact lens, or a hard corneal contact lens, is meant to be that of a corneo-scleral contact lens. The contact lens which is disclosed herein is that of a corneo-scleral contact lens. Therefore when reading this disclosure the term "contact lens" should always be interpreted to be that of a corneo-scleral contact lens with the exception noted within this paragraph. The term scleral ring should be understood to have the meaning as defined in the definitions which are contained herein.

The embodiments disclosed herein teach a prosthesis in the form of a corneo-scleral contact lens and in the form of a scleral ring. The corneo-scleral contact lens has a region or zone of a minimum of 25 or more microns of incremental thickness located anywhere within a region outside of a point 3.0 mm from the geometrical center of the contact lens, whereby the corneo-scleral contact lens thru its optic zone provides the appropriate optical power to largely correct the wearer's uncorrected refractive error and whereby the incremental thickness is the thickness delta measured at the same point compared to that of the same manufacturer's conventional contact lens for providing the same optical power correction and of the same type and whereby the region of incremental thickness causes a widening of the palpebral fissure of the wearer's eye. The corneo-scleral contact lens can be by way of example only, a soft contact lens or a hybrid contact lens. The corneo-scleral contact lens can be of an optical design of any one or more of a single vision, multifocal, toric, and astigmatic contact lens. The soft contact lens can be that of a continuous wear, daily wear, planned replacement or disposable. The corneo-scleral contact lens can have a colored, tinted iris ring, limbal ring or circular band located appropriately removed from the optic zone of the contact lens to further accentuate a widening of the palpebral fissure of the wearer. A portion of this colored, tinted ring or band can be located approximately adjacent but over that of the limbus of the eye of the wearer and can extend beyond the limbus of the wearer. Meaning the outer diameter of the colored portion to colored portion can be larger than the diameter of the limbus to limbus measurement.

The scleral ring is that of a ring which generally, but not always, has its outer peripheral edge located under the upper and lower lids when the eye is opened normally and has its inner peripheral edge located outside of the wearer's pupil diameter (when naturally dilated for darkness) such to not interfere with the line of sight of the wearer. The inner edge of a scleral ring (adjacent to the open center aperture) has a similar contour as that of the peripheral edge of the scleral ring. This helps to prevent discomfort for the wearer when he or she blinks. The scleral ring has an open central aperture which allows for the wearer's line of sight to be uninhibited. The scleral ring can be comprised of any of the various contact lens materials; hard, gas perm, soft, hybrid. The scleral ring can comprise an aperture widening zone or region of incremental thickness, regressive thickness and/or an area of increased surface friction. An increased surface friction zone can be flat or raised on the convex surface of the prosthesis. The region or zone of incremental thickness can be, by way of example only, made of one material (which is that of the base material of the ring) or of multiple materials such that a more pliable softer material is affixed to the more rigid, less pliable soft material of the main scleral ring. In most, but not all cases, when speaking of a hybrid scleral ring the more pliable material (less rigid) provides the upper lid lift and lower lid depression.

A hybrid scleral ring in some, but not all, embodiments can comprise finger like members that lift the upper lid and/or lower the lower lid. The scleral ring does not comprise optical power. The mechanism of action is that the upper and lower lids provide a force when closing or closed that overcomes the normal force needed to fold or bend the finger like member, but upon the lids being reopened the force needed to fold or bend the finger like member becomes less than that imposed by the structure of the finger like member and thus the finger like member springs back into position thus now overcoming and elevating or lifting the upper lid and/or depressing or lowering the lower lid. In some embodiments, but not all, of the hybrid scleral ring the finger like member is bent or folded into a receiving trench which was pre-formed (designed) in an outer surface of the scleral ring. The location of the trench or trenches is provided in the proper location relative to each finger like member. This allows for the finger like member (members) to be folded almost flat as it blinks so that the lid can easily close or open over the finger like member (members). It should be also pointed out that while the disclosure shows and teaches the finger like members being associated with the scleral ring prosthesis they can also be associated with a contact lens prosthesis.

The incremental zone can be comprised of a homogenous material when the scleral ring and contact lens is made of one material or a hybrid zone when the scleral ring or contact lens is made of two materials. In some embodiments of the prosthesis there may or may not be an incremental thickness zone or region or a regressive thickness zone or region, but rather the surface of the zone or region is altered to provide to provide additional lid friction. This region or zone of increased surface friction can be easily over come during an eye lid blink or forced closure, but upon opening the eye lid this region of increased friction elevates the upper lid and/or depresses the lower lid thus opening the aperture of the eye. An increased surface friction zone, region, area can be flat or raised on the convex surface of the prosthesis. An increased surface friction zone, region, area can be an aperture widening zone, region, area.

The zone of incremental thickness or increased surface friction found in some embodiments of the prosthesis taught herein can be shaped, by way of example only, as that of a: ring (rings), ringlets, partial rings, band, bands, partial bands, dome, a series of domes, isolated regions or islands of any geometrical shape, segmented area, or segmented areas. The zone of incremental thickness is located on the convex outer surface of the contact lens. The zone of incremental thickness can be expressed as the area of thickness that elevates from that of the normalized outer convex surface curvature of the contact lens or scleral ring. In most, but not all, preferred embodiments of the contact lens or scleral ring the zone of incremental thickness (of aperture widening zone) is connected to that of the outer convex surface curvature at the point where its outer slope meets the convex surface or its inner slope meets the convex surface in a continuous manner (meaning the convex curvature of the contact lens or scleral ring is that of a continuous surface). In some other embodiments the convex surface has a discontinuity or discontinuities imparted there-upon which are located adjacent to or near the region or regions of incremental thickness and thus is not a continuous surface. When speaking of a hybrid scleral ring in some embodiments the incremental thickness zone is formed by way of a discontinuous surface where one material is affixed to another material. When speaking of a homogenous scleral ring, the ring is made out of one material and in most cases utilizes an incremental thickness region (aperture widening zone) to provide the lifting of the upper lid and/or lowering of the lower lid.

The term prosthesis as used herein is meant to be one of: a corneo-scleral contact lens, or a scleral ring. The term "contact lens" as used herein is meant to be that of a corneo-scleral contact lens which can be one of: rigid, soft, gas perm, or hybrid.

The zone/region/area of incremental thickness (aperture widening zone) which comprises the zone of incremental thickness in most, but not all, embodiments is located on the convex surface adjacent to the outer edge of the pupillary zone and outside the pupillary zone of the contact lens or scleral ring. The pupillary zone is the same size or smaller than the contact lens optical zone and is located within the central open aperture of the scleral ring. The maximum thickness delta of the incremental thickness zone is located at (in alignment with) or external (outside of) to the limbus of the wearer's eye when the prosthesis being that of a contact lens or scleral ring is worn. This means the maximum thickness delta or maximum change in thickness of the incremental thickness zone (aperture widening zone) is equal to or of a larger diameter than the measurement of the limbus to limbus diameter (outside corneal diameter) thru the geometrical center of the cornea of the eye to which the contact lens or scleral ring is being worn or intended to be worn. The contact lens or scleral ring as taught herein is that of a contact lens or scleral ring comprising an incremental thickness zone, whereby the incremental thickness zone has an incremental thickness, a slope and a width, and whereby the incremental thickness diameter is within the range of 1 mm to 10 mm larger than the natural palpebral fissure of the wearer's eye. The zone of incremental thickness is located on the convex surface and acts as an elevator of the upper lid and/or a depressor of the lower lid. The net cosmetic effect is to widen the aperture or palpebral fissure (aperture) of the wearer's eye.

In some further embodiments a regressive thickness region is provided on the convex surface design such to provide a topography that will also cause the eye aperture widening effect. In this case the regressive thickness region forms a valley in the convex surface such to cause the upper lid to be elevated/lifted and the lower lid to be lowered/depressed. The surrounding topography of the valley becomes an incremental thickness region, zone, area, etc.

In most preferred embodiments the prosthesis can remain thinner in overall area when an incremental thickness region is added/designed, as opposed to a regressive thickness region being designed into the prosthesis. This is due to the fact that the regressive thickness region is really the effect of a subtraction of thickness in the regressive thickness region. Thus in order to obtain (by way of a regressive region) the needed valley depth in the convex surface of the prosthesis such to provide for the aperture widening effect the area located internal (closer to the center of the lens) must be thicker than the regressive region. Thus the prosthesis having a regressive thickness region will be thicker in total surface area than that of a prosthesis comprising an incremental thickness region. In most cases a prosthesis having a thinner overall surface area is preferable to a thicker overall surface area. Now having said the above, in some embodiments of the prosthesis a regressive thickness region is utilized to provide the eye aperture widening effect.

The incremental thickness region and/or the regressive thickness region can be one of: rotationally symmetric, rotationally asymmetric, elliptical arch like feature (features), island or island like areas. The elliptical arch (arches) like feature (features) can resemble the curve of lid margin of the upper lid and/or the curve of the lid margin of the lower lid. In some embodiments the incremental thickness zone can form somewhat vertical islands located on either side (right or left) of the optic zone (in the case of a contact lens) or open aperture (in the case of a scleral ring).

The incremental thickness region of the prosthesis can have a maximum delta thickness differential (added thickness) within the range of 25 microns to 1,000 microns with a preferred range of 100 microns to 500 microns, with a more preferred range of 100 microns to 400 microns, with a more preferred range of 75 to 400 microns. The maximum delta thickness can be 25 microns, 50 microns, 100 microns, 150 microns, 200 microns, 250 microns, 300 microns, 350 microns, 400 microns, 450 microns, 500 microns, 550 microns, 600 microns, 650 microns, 700 microns, 750 microns, 800 microns, or 1000 microns. The maximum delta thickness differential can be located 0.5 mm to 3 mm from the outer peripheral edge of the prosthesis. The incremental thickness region can be located beginning/starting at or near the outer edge of the prosthesis to 6 mm from the outer edge. In most embodiments the incremental thickness region can be either at the outer edge or 0.1 mm to 3 mm from the outer edge of the prosthesis. The delta of maximum incremental thickness in most cases is within a range of 0.5 mm to 3.0 mm internal to the edge of the prosthesis, with a preferred range of 1.0 mm to 2.5 mm internal to the edge of the prosthesis. The incremental thickness diameter (measured from the point of maximum added thickness thru the geometrical center of the prosthesis to the opposing point of maximum added thickness) can be: 10.5 mm or greater, 11.0 mm or greater, 11.5 mm or greater, 12.0 mm or greater, 12.5 mm or greater, 13 mm or greater, 13.5 mm or greater, or 14.0 mm or greater.

The regressive thickness region of the prosthesis can have a maximum delta thickness differential (reduced thickness) within the range of 25 microns to 1,000 microns with a preferred range of 100 microns to 500, with a more preferred range of 100 microns to 400 microns, with a more preferred range of 75 microns to 400 microns. The maximum delta thickness can be 25 microns, 50 microns, 100 microns, 150 microns, 200 microns, 250 microns, 300 microns, 350 microns, 400 microns, 450 microns, 500 microns, 550 microns, 600 microns, 650 microns, 700 microns, 750 microns, 800 microns, or 1000 microns. The regressive thickness region can be located from the outer edge to 6 mm from the outer edge. In most embodiments the regressive thickness region can be 0.1 mm to 3 mm from the outer edge of the prosthesis. The delta of maximum incremental thickness or delta of maximum regressive thickens in most cases is within a range of 0.5 mm to 3.0 mm internal to the edge of the prosthesis, with a preferred range of 1.0 mm to 2.5 mm internal to the edge of the prosthesis.

The aperture widening zone when caused by incremental thickness comprises two slopes divided by a point of maximum change thickness (maximum thickness delta). These two slopes are called the outer slope and the inner slope. The "outer" slope on the side closest to the outer edge of the prosthesis of the aperture widening zone (incremental thickness region or regressive thickness region) helps to achieve the aperture widening effect. The "outer" slope can be, by way of example only, 50 microns per mm or greater, 100 microns per mm or greater, 150 microns per mm or greater, 200 microns per mm or greater, 250 microns per mm or greater, 300 microns per mm or greater, 350 microns per mm or greater. The "inner" slope can be, by way of example only, 50 microns per mm or less, 100 microns per mm or less, 150 microns per mm or less, 200 microns per mm or less, 250 microns per mm or less, 300 microns per mm or less, 350 microns per mm or less. If the "outer" slope has a change in thickness of less than 50 microns per mm the widening effect is minimized. If the outer slope has a change in thickness of greater than 300 microns per mm the prosthesis becomes uncomfortable and may decenter. A range of an outer slope of the aperture widening zone on the side closest to the outer edge of the prosthesis is within a minimum of 3 degrees to a maximum of 45 degrees, and preferably within a range of 5 degrees to 25 degrees. A range of an "inner" slope of the aperture widening zone on the side closest to the geometrical center of the prosthesis can be within the range of a minimum of 1 degree to a maximum of 15 degrees. In most, but not all embodiments the outer slope is greater than the inner slope. In some embodiments the outer slope is approximately equal to that of the inner slope. And in some embodiments the inner slope is greater than the outer slope.

In some embodiments, the prosthesis can comprise an aperture widening zone (incremental thickness region or incremental regressive thickness region) on its convex surface, whereby the aperture widening zone causes a bump on the convex surface that provides for the aperture widening effect. This bump (which is caused by incremental thickness or regressive thickness) has a curvature shape, slope angle, change in thickness per millimeter and maximum change in thickness (maximum delta thickness). In some embodiments the aperture widening zone's outer slope can begin at or adjacent to the outer peripheral edge of the prosthesis and continues to the maximum thickness delta of the aperture widening zone. In some embodiments, when the outer slope begins at or adjacent to the outer peripheral edge the outer slope will be within 2 degrees of the slope of the outer edge. In most, but not all embodiments, the location of the maximum thickness delta is achieved within the range of 1 mm to 3 mm from the outer edge, with a preferred range of 1.0 mm to 2.5 mm from the outer edge. The aperture widening zone can comprise a width of 1 mm to 6 mm when measured from the outer edge proceeding across the aperture widening zone towards the geometrical center of the prosthesis.

In most, but not all embodiments a least one bump is located above and below the geometrical center along an imaginary vertical axis that crosses the geometrical center of the prosthesis. In some other embodiments a least one bump is located on either side of the geometrical center such to be intersected by an imaginary horizontal axis that crosses the geometrical center of the prosthesis. Still in other embodiments multiple isolated bumps can be located such to be intersected by an imaginary axis going through the geometrical center of the prosthesis, by way of example only, two or more of: 40 degrees, 45 degrees, 90 degrees, 135 degrees, 150 degrees, 180 degrees, 210 degrees, and 330 degrees, relative to the geometrical center of the prosthesis.

The location of the peak delta incremental thickness (maximum change in thickness) region (zone, area) or the peak delta regressive thickness (maximum change in thickness) region (zone, area) of the prosthesis can be located 0.1 mm or more superior (above) with respect to the upper lid margin and/or 0.1 mm or greater inferior (below) with respect to the lower lid margin of the wearer, but more preferably located 0.5 mm or more superior (above) to the upper lid margin and/or 0.5 mm or greater inferior (below) to the lower lid margin of the wearer. It is important to note that the above measurements contained in this paragraph are of the lids "without the prosthesis being worn" and as of the time the wearer's eye is looking straight ahead and relaxed without straining to see clearly or in bright light (this being the natural aperture of the wearer's eye). Thus when wearing the prosthesis the upper lid is elevated by a minimum of 0.1 mm or more and/or the lower lid is depressed (lowered) by a minimum of 0.1 mm or more. But in a more preferred example, when wearing the prosthesis the upper lid is elevated by a minimum of 0.5 mm or more and/or the lower lid is depressed (lowered) by a minimum of 0.5 mm or more. The aperture widening of the prosthesis can be further accentuated by way of a colored accent color. The colored accent color can be a colored limbal ring or a colored circle ring (which can be referred to as a colored circle lens) located on the prosthesis. Thus the more the wearer's eye aperture is widened by the prosthesis which has this colored accent color, such as a colored limbal ring, the more colored limbal ring can be observed by someone looking at the eye of the wearer. This provides a very complementary effect which makes the colored limbal ring, color ring or color accent more dramatic in its cosmetic enhancement of the wearer's eye. A portion of the colored accent color will be located at (above and adjacent to) or external to the limbus of the wearer's eye when the color accented prosthesis is being worn. This means that a portion of the color accented prosthesis is located, when worn, on top of or external to the limbal area of the eye of the wearer. Thus the diameter of a portion of the colored accent portion is equal to or larger in diameter to that of the outside diameter of the cornea of the wearer.

In some embodiments, such as by way of example only, a prosthesis that is of a contact lens multifocal design and/or one that corrects for astigmatism and thus requires optical power having a toric component and a stabilization zone (feature or member) is employed. In some embodiments, such as by way of example only, when a prosthesis that is a scleral ring or one that is a single vision contact lens having only spherical optical power the prosthesis is free to rotate upon normal blinking and thus devoid of a stabilization zone (feature, member). In some other embodiments a stabilization zone (feature or member) is employed for a single vision spherical power contact lens. When a stabilization zone (feature or member) is employed it can be built onto or into the design of the aperture widening zone (thus they are specially designed to be one in the same) or it can be separate from the aperture widening zone.

An increased surface friction region/zone/area can be located on the convex surface of the prosthesis and can increase the aperture of a wearer's eye. An increased surface friction zone/region/area can be called an aperture widening zone/region/area. The increased surface friction region/zone/area can be flat, irregular, raised, or integrated on the convex surface of the prosthesis. The increased surface friction region's width can have a width that includes the outer edge of the prosthesis to a point 6 mm from the outer edge. In some other embodiments the increased surface friction region is located within 0.1 mm and 6 mm from the outer edge of the prosthesis. Given that in certain embodiments the increased surface friction region can be flat and thus approximate a zone/region/area on the convex surface of the aperture widening zone or a portion thereof of the prosthesis comprising an increased surface friction region the region has no thickness slope. In other embodiments there is a thickness slope. An increased surface friction region can be fabricated on the convex surface of aperture widening zone of the prosthesis or a portion thereof, by way of any known means including, by way of example only; molding, thermoforming, surface treatment, coating, etching, deposition, gas etching, gas treatment, laser etching, laser treatment, chemical etching, and chemical treatment. Any convex surface region/zone/area of the prosthesis located within the range of 0 mm to 6 mm from the outer edge of the prosthesis which comprises 1% or greater in drag friction compared to an area of the convex surface located beyond 6 mm from the outer edge would be considered an increased surface friction region/zone/area. By way of example only, such an increased surface friction convex surface region/zone/area could be: a coated surface, dimpled surface, crazed surface, surface bumps, surface rings, surface lines, non-slick surface, irregular surface, etc.

The dimples, bumps, rings, and lines of the increased surface region/zone/area have a vertical depth. The vertical depth is defined by the distance between a peak and trough of the dimple, bump, ring, or line. The vertical depth of these features is within the range of 500 angstroms to 50 microns, and preferably within the range of 1 micron to 10 microns.

The increased surface friction region/zone/area can be a stand-alone feature located on the convex surface of the prosthesis. Additionally, the increased surface friction region/zone/area can be located on the outer slope of an aperture widening zone or a portion thereof.

The increased surface friction region/zone/area can also be created by not polishing all or part of the aperture widening zone on the convex surface of the prosthesis. This will result in a region/zone/area defined by the aperture widening zone that has an increased surface friction relative to the rest convex surface, which is polished.

Figure 12A:
FIGS. 12A-B show a prosthesis having an aperture widening zone according to one embodiment superimposed on the eyes of an individual.
Figure 12B:
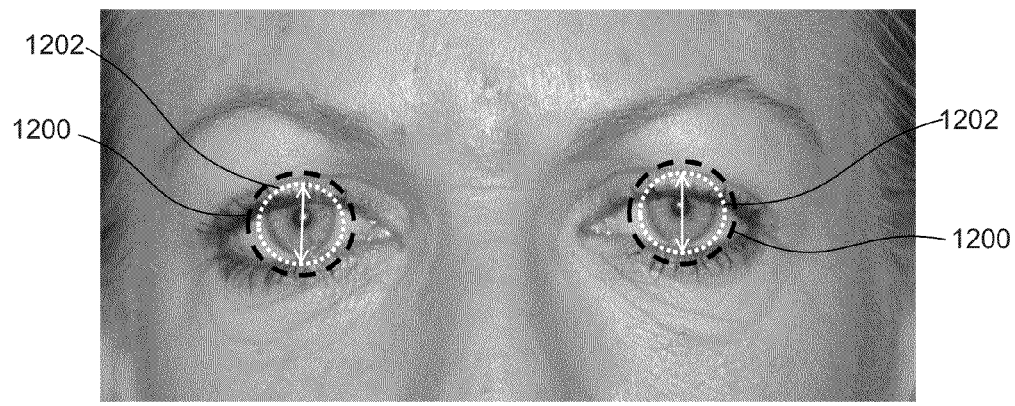
Figure 13A:
FIGS. 13A-B show a prosthesis having an aperture widening zone according to one embodiment superimposed on the eyes of an individual.
Figure 13B:
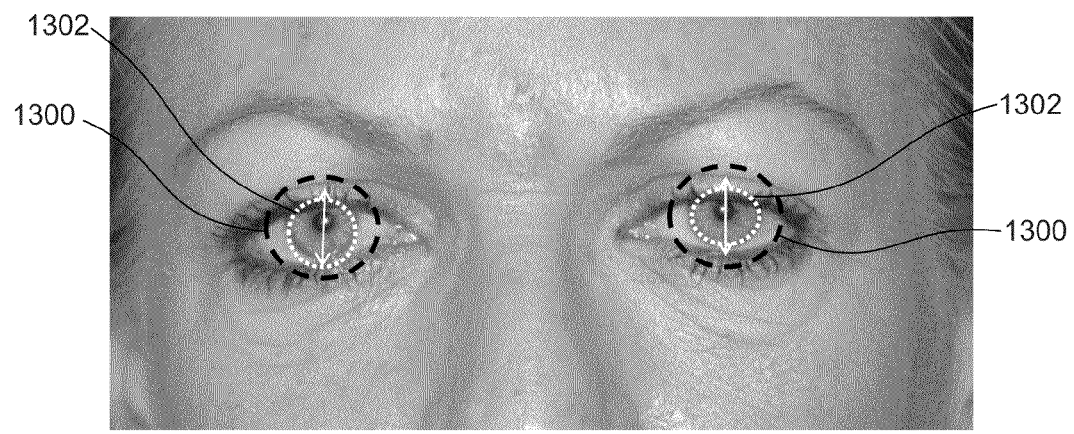

FIGS. 12A-B and 13A-B illustrate two ways in which an aperture widening zone is capable of widening the palpebral fissure of an individual's eyes. FIGS. 12A and 13A show an individual not wearing a prosthesis as described herein and FIGS. 13A and 13B show the same individual with a prosthesis having an aperture widening zone superimposed onto her eyes.

FIG. 12B shows an embodiment of a prosthesis 1200 whereby a maximum delta thickness 1202 falls outside of the natural aperture of the eye. Said another way, when worn the maximum delta thickness 1202 of an aperture widening zone (zones) of the prosthesis 1200 is located above the upper lid margin and below the lower lid margin when the eye is relaxed and looking straight ahead. The incremental thickness diameter (which is the diameter measured from a point of maximum added thickness thru the geometrical center of the prosthesis to the opposing point of maximum added thickness) is larger than the distance between the upper lid margin and the lower lid margin.

The incremental thickness diameter and also the regressive thickness diameter is the distance along an axis from a point of maximum delta thickness proceeding through the geometrical center of the prosthesis in a straight line to that of a point of maximum delta thickness located on the opposite side from the previous point of maximum delta thickness. The embodiments disclosed herein teach when fitting the prosthesis to fit the prosthesis whereby the maximum delta thickness (also called the peak thickness delta) is located at a minimum 0.1 mm above with respect to the upper lid margin and/or 0.1 mm below with respect to the lower lid margin.

The incremental thickness diameter and the regressive thickness diameter of the prosthesis can be of any diameter depending upon the overall diameter (outer most diameter) of the prosthesis, however, in most cases the incremental and regressive thickness diameter is within the range of 10.5 mm to 15 mm.

The location of the maximum delta thickness 1202 on prosthesis 1200 is located under and above with respect to the upper lid margin and located under and below with respect to the lower lid margin, thus widening the palpebral fissure (aperture) of the eye. To be clear in this embodiment the location of the maximum delta thickness does not fall within the natural aperture of the eye as it falls outside or a larger distance measurement than the vertical measurement of the natural aperture of the eye (meaning the incremental thickness diameter is greater than the vertical measurement of the natural eye aperture). In the case of this embodiment the upper eye lid is lifted due to the aperture widening zone being one or more of an incremental thickness zone, regressive thickness zone, or increased surface friction region. And the lower lid is pushed down also due to the aperture widening zone being one or more of an incremental thickness zone, regressive thickness zone, or increased surface friction region. The method of action in the case of an embodiment having an incremental thickness zone (region, area) results by way of either the added thickness pushing out and up the upper lid and pressing down and out the lower lid. The method of action in the case of an embodiment having a regressive thickness zone (region, area) results by way of either the upper lid margin and lower lid margin being contacted by the slope where the regressive thickness zone border begins to add significant thickness on the side closest to the pupil of the eye or being contacted and held within the valley of the regressive thickness zone. The method of action in the case of an embodiment having an increased surface friction (region, area) results by way of either the added thickness pushing out and up the upper lid and pressing down and out the lower lid.

FIG. 13B shows the location of a maximum delta thickness 1302 on a prosthesis 1300 being located at the upper lid margin and the lower lid margin. Note how the dotted lines in FIG. 13B are smaller in diameter (the incremental thickness diameter or the regressive thickness diameter) compared to the same dotted lines of the embodiment described in FIG. 12B. FIG. 12B has a larger incremental thickness diameter or regressive thickness diameter compared to FIG. 13B. The method of action of this embodiment utilizes the outer slope across the width of the incremental thickness zone to accomplish the widening effect. By having a steep slope (crossing the incremental thickness zone width or the regressive thickness zone width) which ascends (grows) in thickness from its beginning on the side facing the outer edge of the of the prosthesis 1300 to the maximum delta thickness 1302 located just inside of the natural aperture of the eye, the slope acts as a sliding board or prism shaped wedge that causes the upper lid to move up and the lower lid to move down thus opening the eye's aperture. With this embodiment it is possible for the incremental thickness diameter or regressive thickness diameter to have a maximum delta thickness that falls within the normal/natural aperture of the eye.

FIGS. 14A-17B illustrate various embodiments of aperture widening zones/incremental thickness regions present on the convex surface of a prosthesis.

FIG. 14A illustrates a scleral ring 1400 according to one embodiment. Scleral ring 1400 has a central open aperture 1404 with a geometric center 1402 located in the center. Scleral ring 1400 includes two incremental thickness regions 1408 located on opposite sides of open aperture 1404. Each incremental thickness region 1408 has a maximum incremental thickness (peak delta thickness) 1406. Incremental thickness regions 1408 are capable of increasing the palpebral fissure of a wearer's eye when worn.

FIG. 14B illustrates a contact lens 1450 according to another embodiment. Contact lens 1450 has an optical region 1454 with a geometric center 1452 located in the center. Contact lens 1450 includes two incremental thickness regions 1458 located on opposite sides of optical region 1454 both in the shape of raised islands. Each incremental thickness region 1458 has a maximum incremental thickness (peak delta thickness) 1456. Incremental thickness regions 1458 are capable of increasing the palpebral fissure of a user's eye when worn.

Figure 15C:
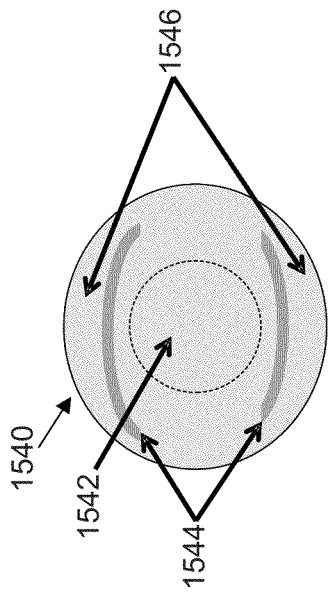
FIGS. 15A-D show various embodiments of a contact lens with different aperture widening zones having an incremental thickness.
Figure 15D:
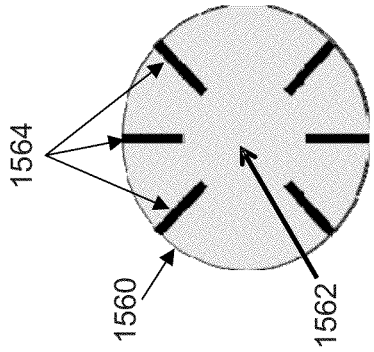
Figure 15A:
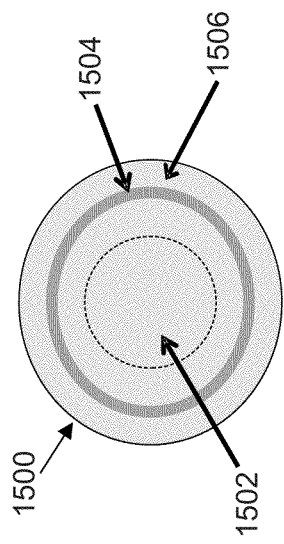

FIG. 15A illustrates a contact lens 1500 according to another embodiment. Contact lens 1500 includes an optic zone 1502 surrounded by a ring-shaped incremental thickness or regressive thickness region 1504. Contact lens 1500 also includes a regressive thickness region 1506 surrounding incremental thickness or regressive thickness region 1504 and extending towards the edge of contact lens 1500.

Figure 15B:
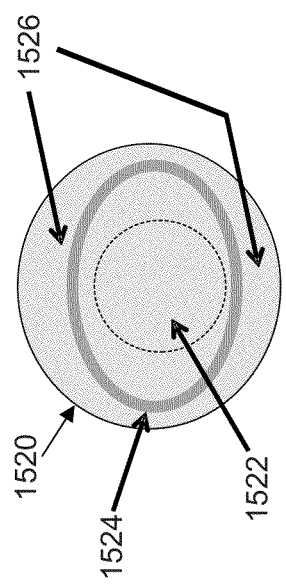

FIG. 15B illustrates a contact lens 1520 according to another embodiment. Contact lens 1520 includes an optic zone 1522 surrounded by an oval-shaped incremental thickness or regressive thickness region 1524 Contact lens 1520 also includes a regressive thickness region 1526 surrounding incremental thickness or regressive thickness region 1524 and extending towards the edge of contact lens 1520.

FIG. 15C illustrates a contact lens 1540 according to another embodiment. Contact lens 1540 includes an optic zone 1542 with two incremental thickness or regressive thickness regions 1544 located around it, one above and one below. Each incremental thickness or regressive thickness region 1544 has a partial-ring shape. Contact lens 1540 also includes a regressive thickness region 1546 located outside of incremental thickness or regressive thickness regions 1524 and extending towards the edge of contact lens 1540.

FIG. 15D illustrates a contact lens 1560 according to another embodiment. Contact lens 1560 includes an optic zone 1562 with a plurality of band-shaped incremental thickness or regressive thickness regions 1564. Incremental thickness or regressive thickness regions 1564 are located around optic zone 1562 in a spoke-like fashion. Incremental thickness or regressive thickness regions 1564 can extend to the edge of contact lens 1560 (as shown) or can extend to a point inside of the edge (not shown).

FIG. 16A illustrates a scleral ring 1600 according to another embodiment. Scleral ring 1600 includes an open central aperture 1602 surrounded by a ring-shaped incremental thickness or regressive thickness region 1604. Scleral ring 1600 also includes a regressive thickness region 1606 surrounding incremental thickness or regressive thickness region 1604 and extending towards the edge of scleral ring 1600.

FIG. 16B illustrates a scleral ring 1620 according to another embodiment. Scleral ring 1620 includes an open central aperture 1622 surrounded by an oval-shaped incremental thickness or regressive thickness region 1624. Scleral ring 1620 also includes a regressive thickness region 1626 surrounding incremental thickness or regressive thickness region 1624 and extending towards the edge of scleral ring 1620.

FIG. 16C illustrates a scleral ring 1640 according to another embodiment. Scleral ring 1640 includes an open central aperture 1642 with two incremental thickness or regressive thickness regions 1644 located around it, one above and one below. Each incremental thickness or regressive thickness region 1644 has a partial-ring shape. Scleral ring 1640 also includes a regressive thickness region 1646 located outside of incremental thickness or regressive thickness regions 1624 and extending towards the edge of scleral ring 1640.

FIG. 16D illustrates a scleral ring 1660 according to another embodiment. Scleral ring 1660 includes an open central aperture 1662 with a plurality of band-shaped incremental thickness or regressive thickness regions 1664. Incremental thickness or regressive thickness regions 1664 are located around open central aperture 1662 in a spoke-like fashion. Incremental thickness or regressive thickness regions 1664 can extend to the edge of scleral ring 1660 (as shown) or can extend to a point inside of the edge (not shown).

Figure 17D:
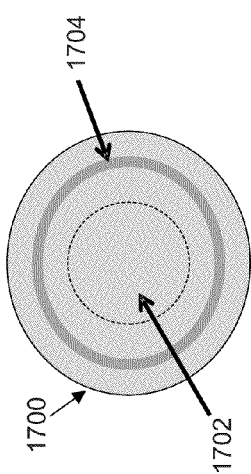
FIGS. 17A-F show various embodiments of a contact lens with different aperture widening zones having increased surface friction.
Figure 17E:
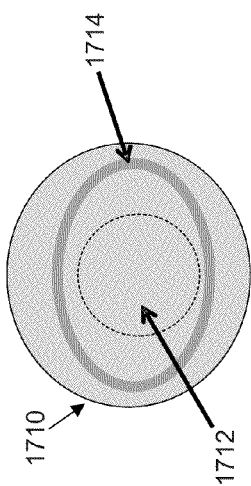
Figure 17F:
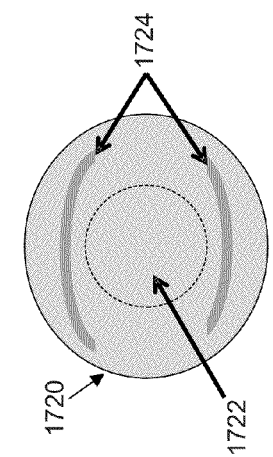
Figure 17A:
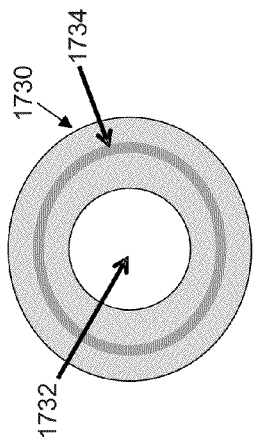
Figure 17B:
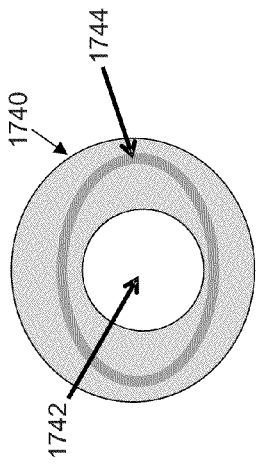
Figure 17C:
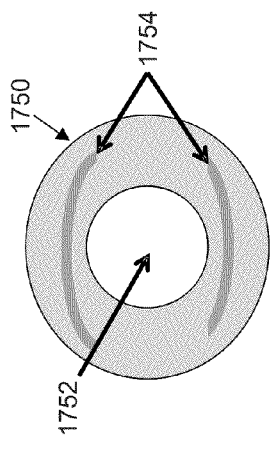

FIGS. 17A-C illustrate various embodiments of a contact lens having an increased surface friction region(s). FIG. 17A shows a contact lens 1700 having an optical region 1702 and a ring-shaped increased surface friction region 1704 surrounding optical region 1702. FIG. 17B shows a contact lens 1710 having an optical region 1712 and an oval-shaped increased surface friction region 1714 surrounding optical region 1712. FIG. 17C shows a contact lens 1720 having an optical region 1722 and two increased surface friction regions 1724 located around optical region 1722, one above and one below. Each increased surface friction region 1724 has a partial-ring shape.

FIGS. 17D-F illustrate various embodiments of a scleral ring having an increased surface friction region(s). FIG. 17D shows a scleral ring 1730 having a central open aperture 1732 and a ring-shaped increased surface friction region 1734 surrounding central open aperture 1732. FIG. 17E shows a scleral ring 1740 having a central open aperture 1742 and an oval-shaped increased surface friction region 1744 surrounding central open aperture 1742. FIG. 17F shows a scleral ring 1750 having a central open aperture 1752 and two increased surface friction regions 1754 located around central open aperture 1752, one above and one below. Each increased surface friction region 1754 has a partial-ring shape.

The prosthesis allows for modifying "one of more" of the following to optimize the lid lifting effect or palpebral (aperture) widening effect of the prosthesis:

1) Overall Diameter

In most, but not all cases, a larger diameter is most effective. By way of example only 14.5 mm, 14.8 mm, 15.0 mm, 15.5 mm, 16.0 mm, 16.5 mm (in the case of a scleral ring the outer diameter may be of the above dimension or it could be 16.0 mm or larger)

2) Overall Thickness

In most, but not all embodiments, a larger overall thickness is most effective.

3) Edge Thickness

In most, but not all embodiments, the extreme peripheral edge thickness of the contact lens or scleral ring is left unchanged from that normally provided by a contact lens manufacturer of a specific brand lens, of a specific type, and of a specific optical power. Thus the outer edge in most cases, but not all cases, approximates that of a conventional corneoscleral contact lens.

In some embodiments the extreme peripheral edge thickness is increased in thickness.

In most, but not all embodiments, the extreme peripheral edge thickness of the contact lens or scleral ring is left unchanged from that normally provided by a contact lens manufacturer of a specific brand lens, of a specific type, and of a specific optical power. Thus the outer edge in most cases, but not all cases, approximates that of a conventional corneoscleral contact lens.

4) Location of Maximum Added Thickness or Maximum Thickness Delta

In certain embodiments an area inside (towards the center of the prosthesis from the outer edge) of 0.5 mm from the outer edge to 3 mm from the outer edge of the contact lens is increased in thickness. In other embodiments an area inside (towards the center of the prosthesis from the outer edge) of 0.5 mm from the outer edge to 7 mm from the outer edge of the contact lens is increased in thickness. In these embodiments the "width" of the aperture widening zone can be within a range of 2.5 mm to 6.5 mm depending upon the overall diameter of the contact lens. In certain other embodiments the width of the aperture widening zone can be within the range of 1 mm to 7 mm, once again depending upon the overall diameter of the contact lens. In some embodiments the aperture widening zone extends from the outer edge of the prosthesis to within the range of 2.5 mm to 5 mm inside of the outer edge of the prosthesis. The precise distance from the outer edge depends upon the type of prosthesis and also the overall diameter of the prosthesis. In most, but not all embodiments, an area within a range of 0.5 mm to 2.5 mm from the extreme peripheral edge of the prosthesis provides the maximum delta thickness (but preferably within the range of 0.5 mm to 2.0 mm from the extreme peripheral edge of the contact lens or scleral ring).

5) Regions of Incremental Thickness

In most, but not all embodiments, a region or regions of incremental thickness or regressive thickness are located adjacent to or outside 3.0 mm of the geometrical center of the contact lens. Region or regions of incremental thickness or regressive thickness are generally located adjacent to or outside the pupillary zone of the contact lens or scleral ring open aperture.

Such a region or regions can comprise an area or areas on the convex surface of the contact lens, by way of example only, a ring, (rings) band, (bands) or partial rings (ringlets), dome (domes), island (islands), segmented area, segmented areas or of any geometrical shape. The region can be that of a rotationally symmetric region or a rotationally asymmetric region.

In most, but not all embodiments, in the region or regions of incremental thickness the surface geometry of the region or regions is comprised of an increased convex curvature.

In most, but not all embodiments, in region or regions of incremental thickness the surface geometry comprises a continuous surface with that of the overall convex surface of the contact lens or scleral ring.

In most, but not all contact lens embodiments, in the region or regions of incremental thickness the curvature change does not provide any visual correction for the wearer. In all scleral ring embodiments, in the region or regions of incremental thickness the curvature change does not provide any visual correction for the wearer. In most, but not all embodiments, incremental thickness can range from 0.1 microns to 1,000 microns. In most, but not all embodiments of the prosthesis the incremental thickness region can have a point of maximum added thickness. The maximum added thickness can range from 25 microns to 1000 microns. In some embodiments the maximum change in thickness/maximum thickness delta is within a range of 100 microns to 500 microns. In some embodiments the maximum change in thickness is within a range of 75 microns to 400 microns.

6) Increased Surface Friction

Embodiments that utilize increased surface friction can be that of surface friction on the convex surface of the prosthesis forming the aperture widening zone or as part of the incremental thickness zone.

In most, but not all embodiments, the touch area of slide resistance between the contact lens or scleral ring and the lid or lids is increased. This is accomplished by increasing the friction between the lid (lids) and the convex surface of the contact lens, but doing so in such a limited way that it is accomplished without irritating the lid (lids). A difference of 1% or more of increased drag friction within the aperture widening zone can be meaningful compared to the surface friction of the rest of the prosthesis outside of the aperture widening zone.

7) Convex Surface Shape

In most, but not all embodiments, the convex surface shape near and/or around the periphery of the contact lens is altered compared to that normally provided by a contact lens manufacturer of a specific brand lens, of a specific type, and of a specific optical power.

8) Slope Difference

In most embodiments the steepest slope is that of the outer slope of the incremental thickness region and the less steep slope is on the inner slope of the incremental thickness region which is closest to the geometrical center of the contact lens or scleral ring.

In certain embodiments the steepest slope is that of the inner slope of the incremental thickness region and the less steep slope is on the outer slope of the incremental thickness region which is closest to the outer edge of the contact lens or scleral ring.

In certain other embodiments the outer slope of the incremental thickness region is equal to the inner slope of the incremental thickness region 9) Lens Material In most, but not all embodiments, the lens material is that of one of a silicone hydrogel or a hydrogel material.

In some embodiments the lens material is that of one of a gas permeable material or a rigid material.

In some embodiments a different material is added/bonded, inserted, affixed to the contact lens or scleral ring thus altering a region (regions) or area (areas) of the contact lens convex outer surface material.

In some other scleral ring embodiments the scleral ring is made of non-gas perm material.

In some other embodiments the scleral ring material is that of a rigid non-gas permeable material.

10) Edge Shape of the Prosthesis

In most, but not all embodiments, the extreme peripheral edge shape is not altered from that which is available for a specific brand, of a specific contact lens type, and of a specific contact lens optical power.

In some embodiments the edge shape is altered to have a steeper slope on the convex surface internally from the peripheral edge of the contact lens or scleral ring when compared to that available for a specific brand, of a specific contact lens type, and of a specific contact lens optical power.

In some embodiments the edge shape is altered to be a less steep slope internally from the peripheral edge of the contact lens or scleral ring compared to that available for a specific brand, of a specific contact lens type, and of a specific contact lens optical power.

The edge thickness is preferably between 25 and 100 microns. For disposable type contact lenses the edge thickness is preferably between 25 and 50 microns. For non-disposable type contact lenses the edge thickness is preferably between 30 and 60 microns. The edge can be a have a knife edge shape, a rounded shape, a semi-round shape, or a blunt shape.

11) Edge Treatment

In some, but not all, embodiments a portion of the edge of the contact lens or scleral ring is truncated. In some other embodiments two portions (one located adjacent to the upper lid, and one located adjacent to the lower lid) are truncated.

In some, but not all, embodiments the edge is associated with a prism ballast.

In some, but not all, embodiments the edge of the lens is weighted.

12) Base Curve

In most, but not all, embodiments the base curve of the contact lens or scleral ring is increased to be steeper than that normally fit on the cornea or eye of a wearer (with the understanding that, in most but not all cases, the scleral ring is not fit on the cornea of a wearer). If the scleral ring is fit on the cornea it fits only on the peripheral cornea outside of the pupillary zone.

In some, but not all, embodiments the base curve of the contact lens or scleral ring is decreased to be less steep than normally fit on the cornea or eye of a wearer (with the understanding that, in most but not all cases, the scleral ring is not fit on the cornea of a wearer). If the scleral ring is fit on the cornea it fits only on the peripheral cornea outside of the pupillary zone.

In some, but not all, embodiments the base curve of the contact lens or scleral ring is the same as that normally fit on the cornea or eye of a wearer (with the understanding that the scleral ring, in most but not all cases, is not fit on the cornea of a wearer).

13) Convex Surface Texture

In some, but not all, embodiments the convex surface texture of the contact lens or scleral ring can have a region, regions, area, areas of by way of example only; dimples, non-smooth surface, bumps, irregularities, less slick than the area of the prosthesis outside of the aperture widening zone and indentations. This surface texture generally covers or is a portion of the aperture widening zone 14) Optical Power It should be pointed out that the contact lens disclosed herein contemplates all prescription lens powers including that of plano (no power).

The embodiments of the prosthesis (being that of a contact lens and a scleral ring) disclosed herein contemplate the need for a fitting set that the professional will use to test fit on a patient to ensure the best lid lifting result possible for that patient. The fitting set can provide for one or more of the above 14 variables to be tested on the patient to customize and understand the single best variable to alter or a combination of variables to alter when prescribing the contact lens. However, it has been determined that with an optimal fitting set 2 to 6 trial contact lenses should be enough for fitting the majority of all potential wearers.

It should be pointed out that the scleral ring disclosed comprises an open central aperture and "no" optical power. FIGS. 18-23 show various individuals' eyes with and without a prosthesis having an aperture widening zone.

Figure 18:
FIGS. 18-19 show a comparison between the eyes of an individual with and without a prosthesis having an aperture widening zone.
Figure 19:

FIG. 18 shows a 65 year old male's natural eyes, i.e. him not wearing a prosthesis having an incremental thickness region. In contrast, FIG. 19 shows him wearing a prosthesis with an incremental thickness region (aperture widening zone). It can be seen, by comparing FIGS. 18 and 19, that the palpebral fissures of his eyes are widened when wearing a prosthesis having an incremental thickness region as described herein. The prosthesis being worn in FIG. 19 has a base thickness of 100 microns and an incremental thickness region having an overall thickness of 300 microns, with the peak thickness delta or maximum thickness added being 200 microns.

Figure 20:
FIGS. 20-21 show a comparison between the eye of an individual with and without a prosthesis having an aperture widening zone.
Figure 21:

FIGS. 20-21 show the widening of a 45 year old female's palpebral fissure. FIG. 20 shows her natural eye and FIG. 21 shows her wearing a prosthesis having an incremental thickness region on her eye. As can be seen the upper lid has been raised in FIG. 21 when compared to FIG. 20. The prosthesis being worn in FIG. 21 has an incremental thickness region (aperture widening zone) with a maximum added thickness or maximum thickness delta of 600 microns.

Figure 22A:
FIGS. 22A-B show a comparison between an individual's left eye with and without a prosthesis having an aperture widening zone.
Figure 22B:
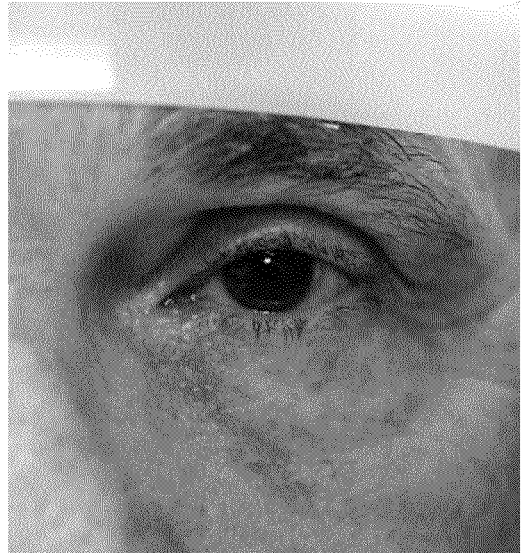

FIGS. 22A-B show the eye of a 66 year old male. FIG. 22A shows his natural right eye having a ptosis of the upper lid and FIG. 22B shows him wearing a prosthesis having an incremental thickness region (aperture widening zone) on the same eye. It can be seen, in FIG. 22B, that the prosthesis with an incremental thickness region lifts his upper right eyelid. Thus opening/enlarging the aperture quite dramatically.

Figure 23:
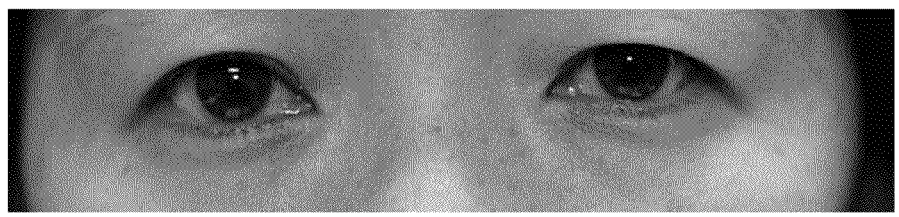
FIG. 23 shows a comparison between the right and left eye of an individual. The individual is wearing a prosthesis having an aperture widening zone on their right eye and is not wearing a prosthesis having an aperture widening zone on their left eye.

FIG. 23 shows the right and left eye of a 40 year old female. She is wearing a prosthesis having an incremental thickness region in her right eye (left side of FIG. 23). She is not wearing a prosthesis in her left eye (right side of FIG. 23). The prosthesis in her right eye has substantially widened the aperture/palpebral fissure of her right eye when compared to her left eye. The prosthesis being worn on her right eye has an incremental thickness region (aperture widening zone) with a maximum increased thickness/maximum thickness delta of 200 microns located approximately 1.5 mm inside the outer peripheral edge of the prosthesis.

Figure 24A:
FIGS. 24A-B show a comparison between the eyes of an individual with and without a prosthesis having an aperture widening zone.
Figure 24B:
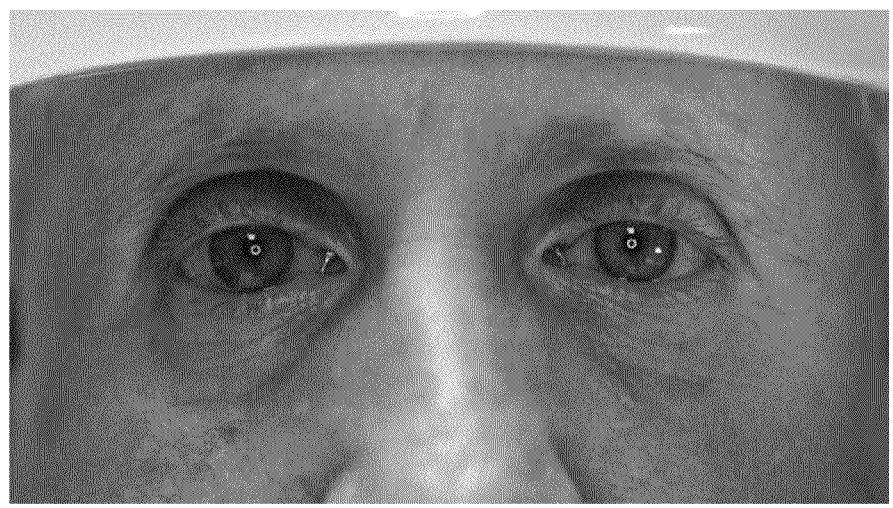

FIG. 24A shows a male's natural eyes, i.e. him not wearing a prosthesis having an incremental thickness region. In contrast, FIG. 24B shows him wearing a prosthesis with an incremental thickness region (aperture widening zone). It can be seen, by comparing FIGS. 24A and 24B, that the palpebral fissures of his eyes are widened when wearing a prosthesis having an incremental thickness region as described herein.

Figure 25A:
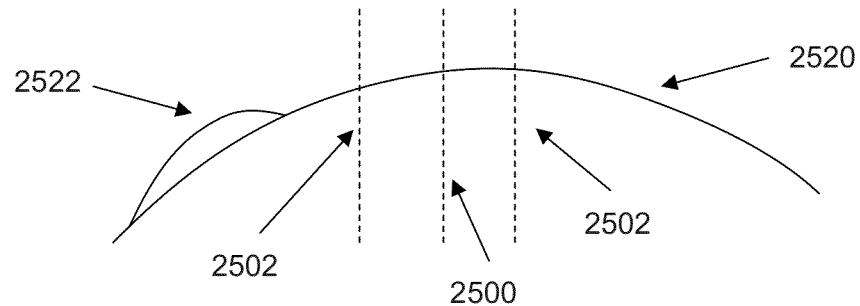
FIGS. 25A-C show the surface profiles for prostheses according to various embodiments.
Figure 25B:
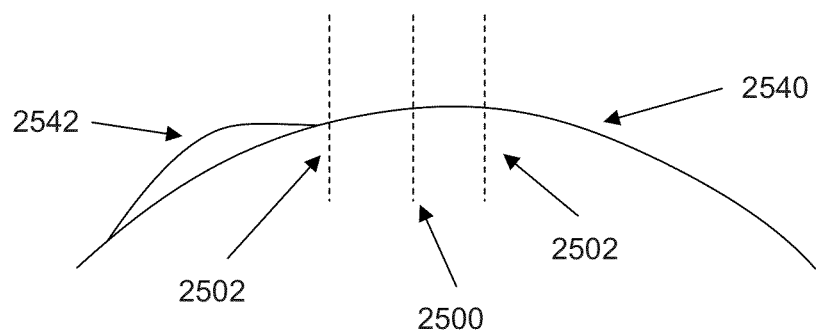
Figure 25C:
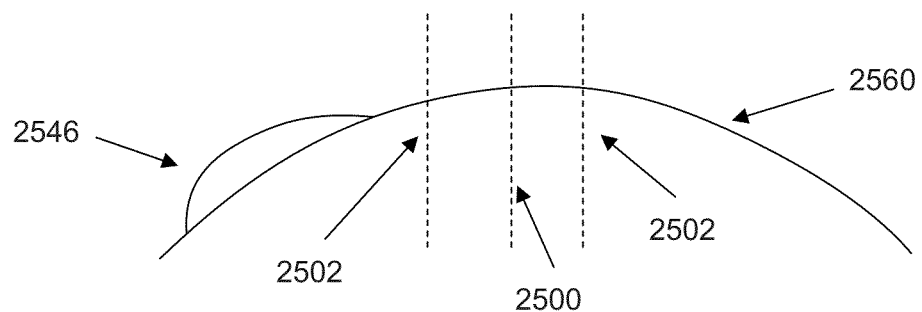

FIGS. 25A-C show various surface profiles for three different prostheses. Lenses 2520, 2540 and 2560 all have a geometric center located at 2500 and a pupil zone indicated by lines 2502. Each lens 2520, 2540, and 2560 has an incremental thickness region 2522, 2542, and 2546, respectively. Note the outer slope of the incremental thickness region 2522 in FIG. 25A is less than the inner slope of the incremental thickness region. Note the outer slope of the incremental thickness region 2542 in FIG. 25B is greater than the inner slope of the incremental thickness region. Note the outer slope of the incremental thickness region 2546 in FIG. 25C is greater than the inner slope of the incremental thickness region.

Incremental thickness Zone Width: The width of the incremental thickness zone or region is the distance measured from its beginning (where incremental thickness begins) on the side towards the outer edge of the prosthesis to the end of the zone or region (where incremental thickness ends) on the side towards the center of the prosthesis. The width of this zone or region generally ranges between 1 mm to 7 mm, but in some cases is between 2.5 mm and 6.5 mm, and in most cases is between 2.5 mm and 5 mm.

Incremental Thickness Profile of the prosthesis can be of an incremental thickness zone that ranges between 0.1 microns to 1,000 microns of incremental thickness. The incremental thickness zone can start at or adjacent to the outer edge of the prosthesis. The maximum delta incremental thickness/maximum added thickness ranges between 25 microns and 1,000 microns, preferably between 100 microns to 800 microns with a preferred delta of 100 microns to 500 microns and a more preferred range being 75 microns to 400 microns. In certain embodiments an area inside (towards the center of the prosthesis from the outer edge) of 0.5 mm from the outer edge to 3 mm from the outer edge of the contact lens is increased in thickness. In other embodiments an area inside (towards the center of the prosthesis from the outer edge) of 0.5 mm from the outer edge to 7 mm from the outer edge of the contact lens is increased in thickness. In these embodiments the "width" of the aperture widening zone can be within a range of 2.5 mm to 6.5 mm depending upon the overall diameter of the contact lens. In other embodiments the width of the aperture widening zone can be within the range of 1 mm to 7 mm, once again depending upon the overall diameter of the contact lens. In some embodiments the aperture widening zone extends from the outer edge of the prosthesis to within the range of 2.5 mm to 5 mm inside of the outer edge of the prosthesis. The precise distance from the outer edge depends upon the type of prosthesis and also the overall diameter of the prosthesis In most, but not all embodiments, an area inside of 0.5 mm to 2.5 mm from the extreme peripheral edge of the prosthesis provides the maximum delta thickness, but preferably within the range of 0.5 mm to 2.0 mm from the extreme peripheral edge of the contact lens or scleral ring.

Figure 26:
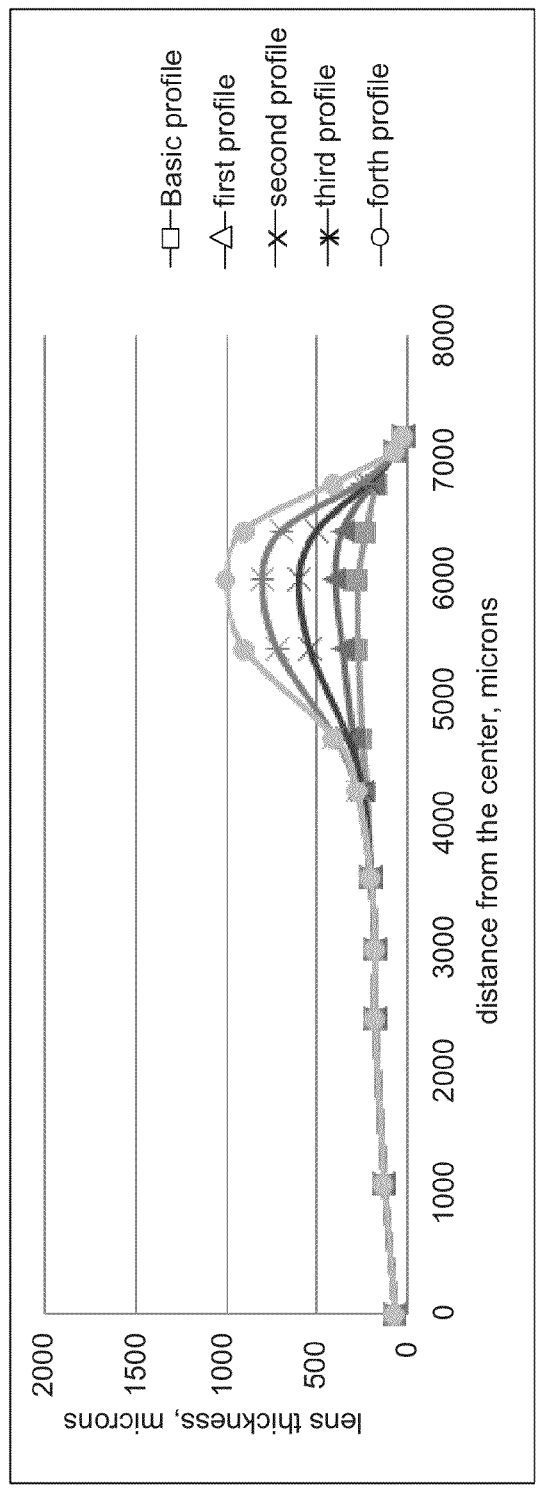
FIG. 26 is a graph illustrating the thickness across prostheses according to various embodiments.
Figure 27A:
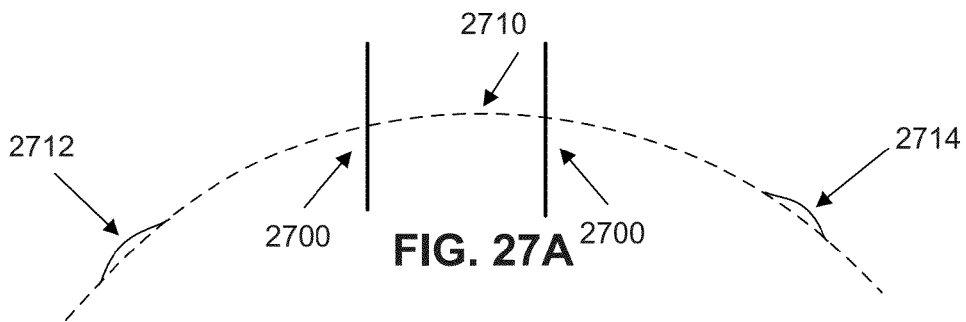
FIGS. 27A-E show the surface profiles for prostheses according to various embodiments.
Figure 27B:
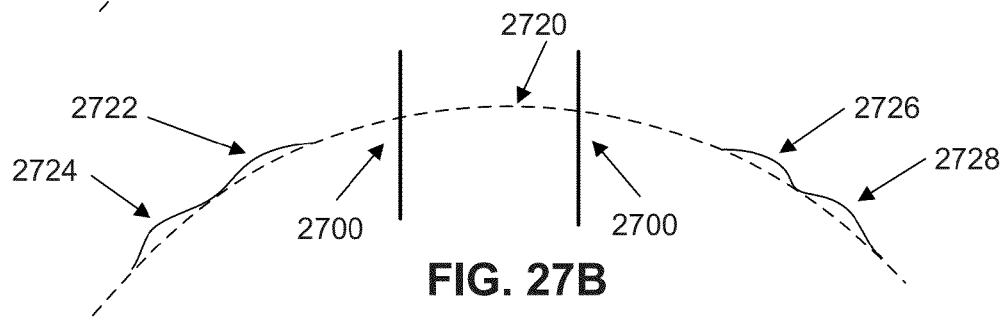
Figure 27C:
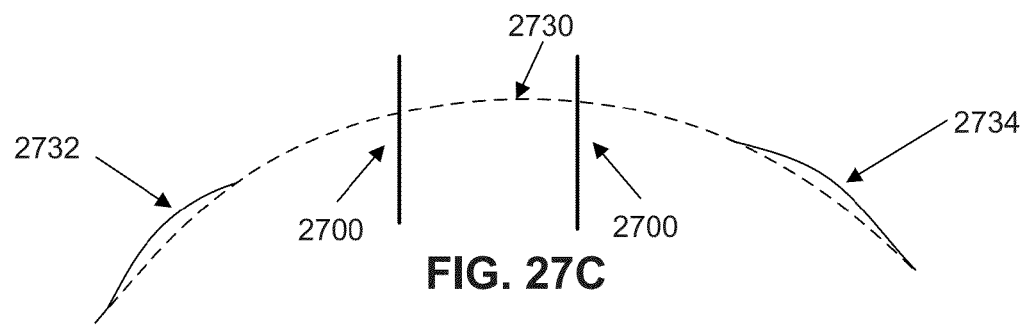
Figure 27D:
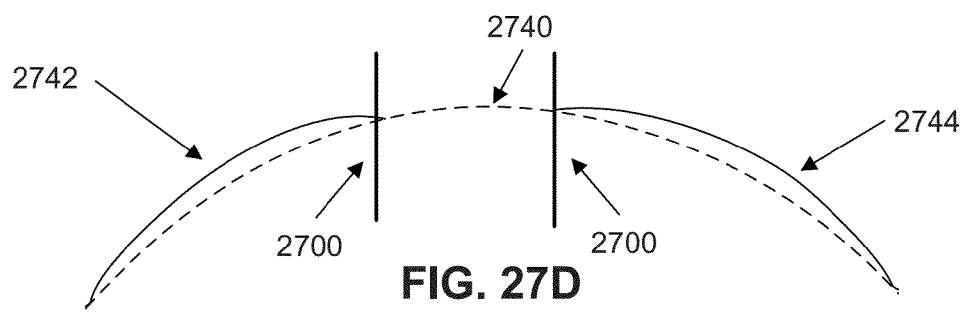
Figure 27E:
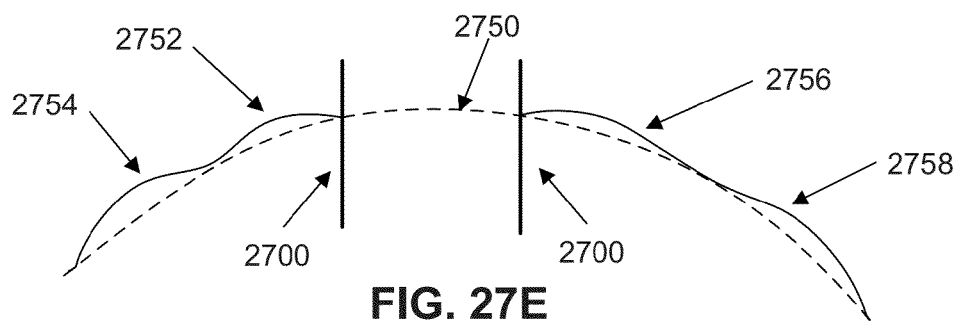

FIG. 26 is an illustration of the thickness profiles of the external convex surface from the edge to the center for some embodiments of the prosthesis described herein. The illustration shows different possible examples of the convex surface profile (slope) and also the incremental thickness region or zone.

FIGS. 27 A-E illustrate various incremental thickness regions for five different prostheses 2710, 2720, 2730, 2740, and 2750. Each prosthesis 2710, 2720, 2730, 2740 and 2750 has a pupil zone 2700 surrounded by areas of incremental thickness. FIG. 27A shows prosthesis 2710 having incremental thickness regions 2712 and 2714. FIG. 27B shows prosthesis 2720 having incremental thickness regions 2722, 2724, 2726, and 2728. FIG. 27C shows prosthesis 2720 having incremental thickness regions 2732 and 2734. FIG. 27D shows prosthesis 2740 having incremental thickness regions 2742 and 2744. FIG. 27E shows prosthesis 2750 having incremental thickness regions 2752, 2754, 2756, and 2758.

Figure 28:
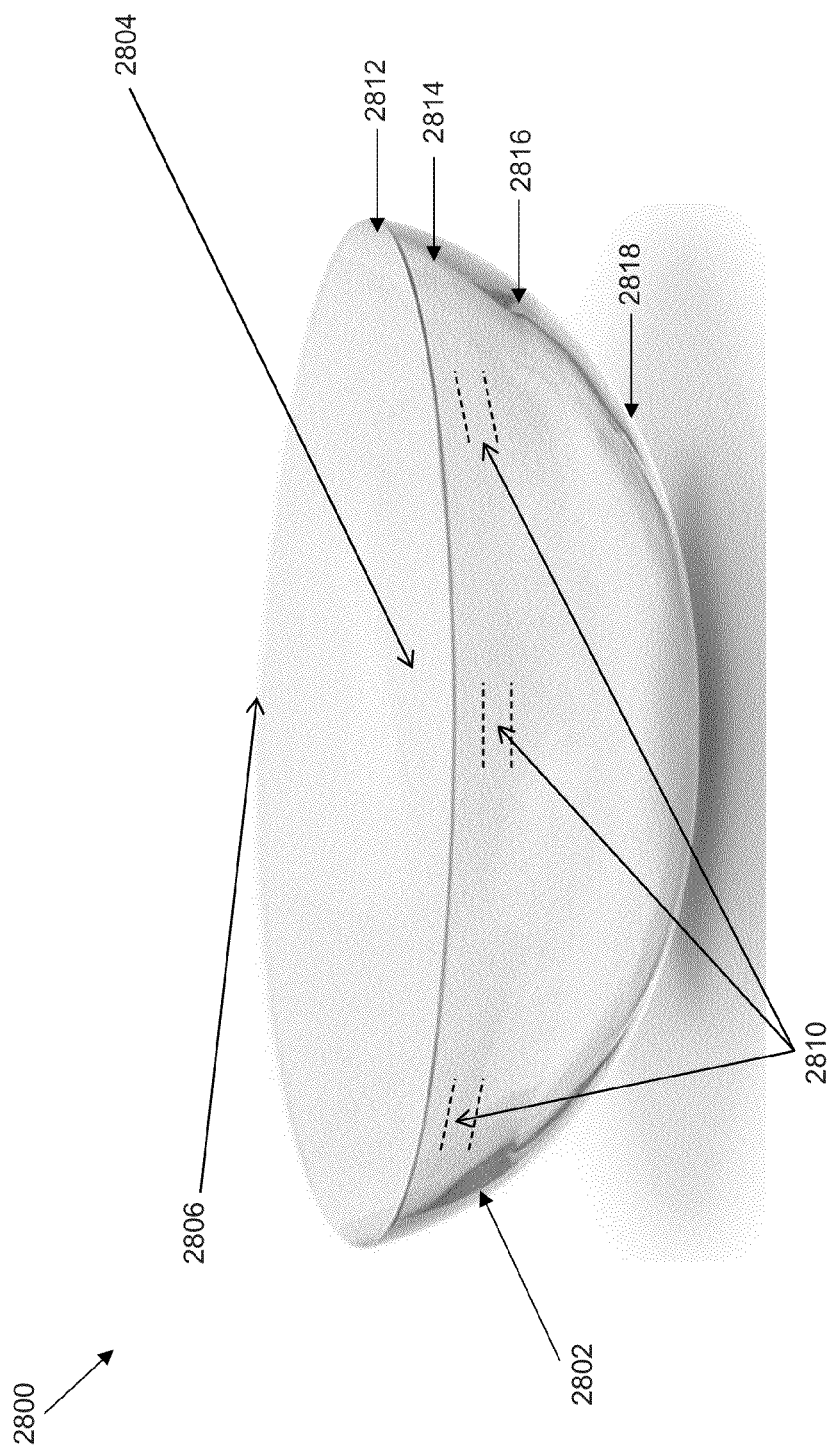
FIG. 28 shows a perspective view of a prosthesis according to one embodiment.

FIGS. 28-34 are perspective views of various contact lenses having various types of aperture widening zones. While FIGS. 28-34 all illustrate contact lenses it will be appreciated that the same features described in reference to FIGS. 28-34 could be incorporated onto a scleral ring. FIG. 28 shows a contact lens 2800 having a convex surface 2802, a concave surface 2804, and a peripheral edge 2806. An incremental thickness region 2810 is located on convex surface 2802. Incremental thickness region 2810 can be a continuous ring of increased thickness or a plurality of discontinuous partial rings of increased thickness. Incremental thickness region 2810 is located interior of peripheral edge 2806 and has a thickness different from the rest of the contact lens 2800. The thickness profile of the lens is illustrated by a first thickness 2812, a second thickness 2814, a third thickness 2816, and a fourth thickness 2818. First thickness 2812, third thickness 2816, and fourth thickness 2818 are equal to the standard thickness of a conventional contact lens. Second thickness 2814, located in the incremental thickness region 2810, has a thickness greater than the standard thickness.

Figure 29:
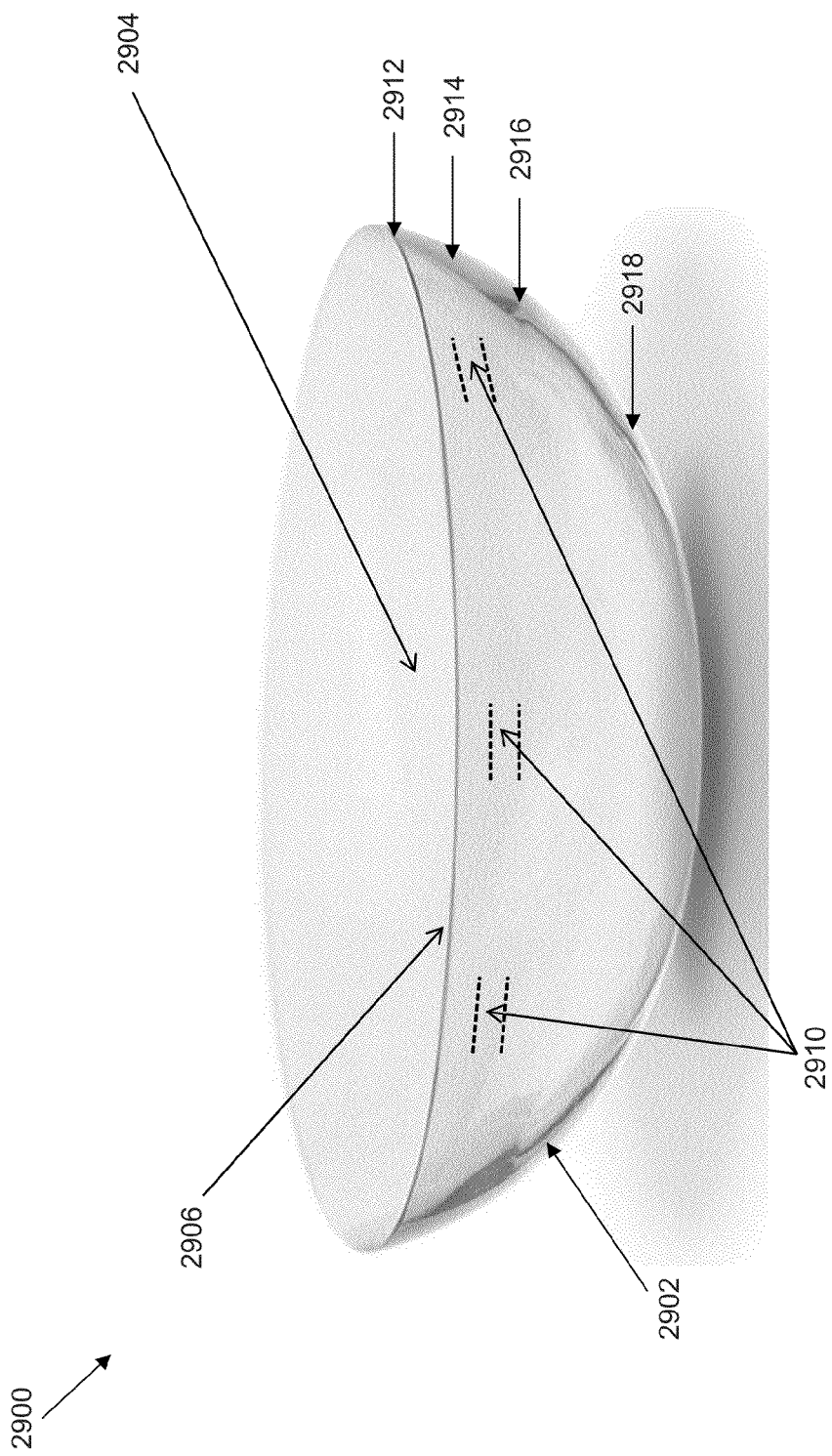
FIG. 29 shows a perspective view of a prosthesis according to one embodiment.

FIG. 29 shows a contact lens 2900 having a convex surface 2902, a concave surface 2904, and a peripheral edge 2906. An increased surface friction region 2910 is located on convex surface 2902. Increased surface friction region 2910 can be a continuous ring having increased surface friction or a plurality of discontinuous partial rings having increased surface friction. Increased surface friction region 2910 is located interior of peripheral edge 2906 and has a surface friction different from the rest of the contact lens 2900. The surface friction profile of convex surface 2902 is illustrated by a first surface friction 2912, a second surface friction 2914, a third surface friction 2916, and a fourth surface friction 2918. First surface friction 2912, third surface friction 2916, and fourth surface friction 2918 are equal to the standard surface friction of a conventional contact lens. Second surface friction 2914, located in the increased surface friction region 2910, has a surface friction greater than the standard surface friction.

Figure 30:
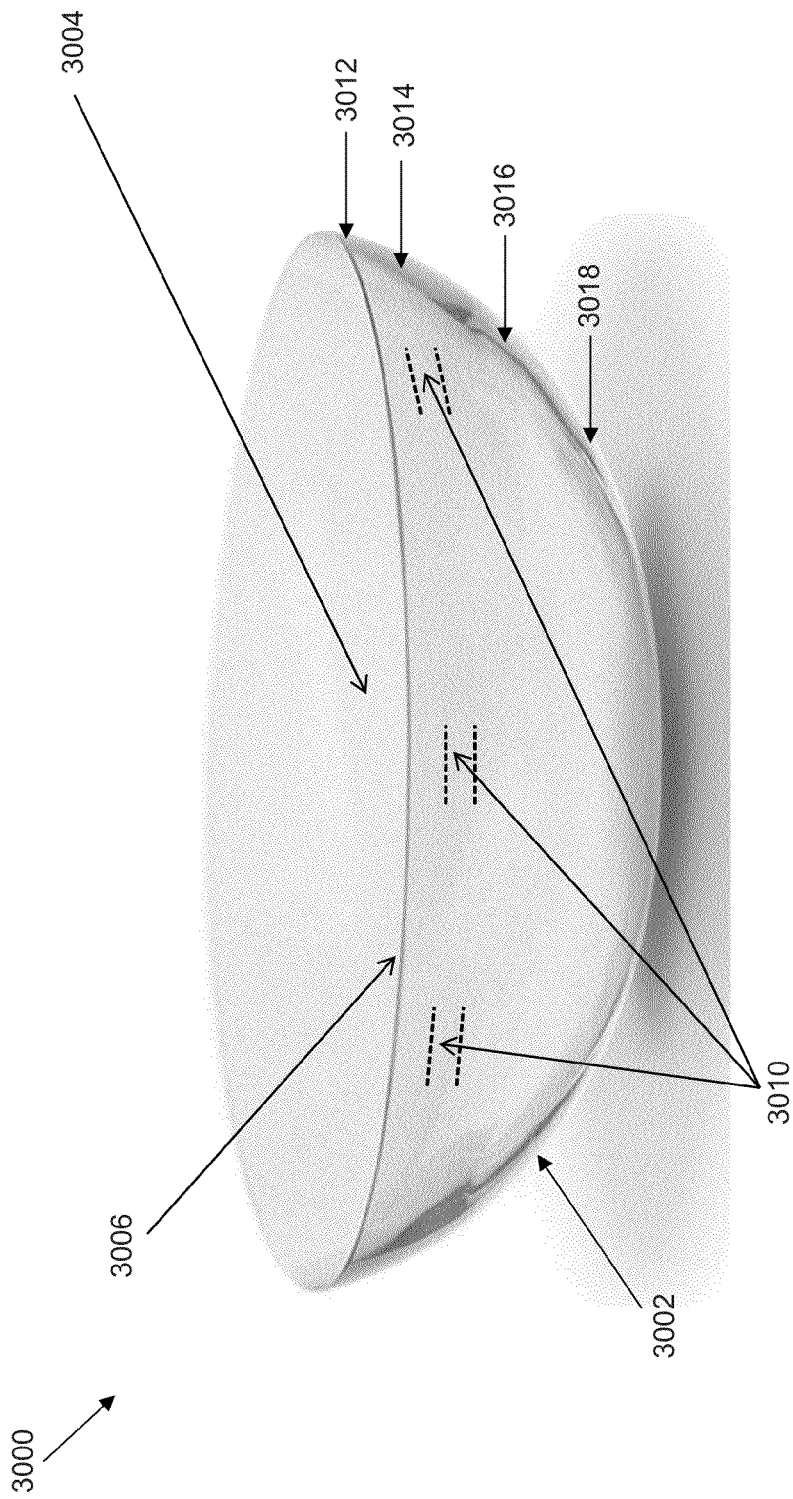
FIG. 30 shows a perspective view of a prosthesis according to one embodiment.

FIG. 30 shows a contact lens 3000 having a convex surface 3002, a concave surface 3004, and a peripheral edge 3006. An incremental thickness and increased surface friction region 3010 is located on convex surface 3002. Incremental thickness and increased surface friction region 3010 can be a continuous ring having incremental thickness and increased surface friction or a plurality of discontinuous partial rings or areas having incremental thickness and increased surface friction. Incremental thickness and increased surface friction region 3010 is located interior of peripheral edge 3006 and has a thickness and surface friction different from the rest of the contact lens 3000. The thickness and surface friction profile of convex surface 3002 is illustrated by a first thickness and surface friction 3012, a second thickness and surface friction 3014, a third thickness and surface friction 3016, and a fourth thickness and surface friction 3018. First thickness and surface friction 3012, third thickness and surface friction 3016, and fourth thickness and surface friction 3018 are equal to the standard thickness and standard surface friction of a conventional contact lens. Second thickness and surface friction 3014, located in the incremental thickness and increased surface friction region 3010, has a thickness and surface friction that are greater than the standard thickness and surface friction.

Figure 31:
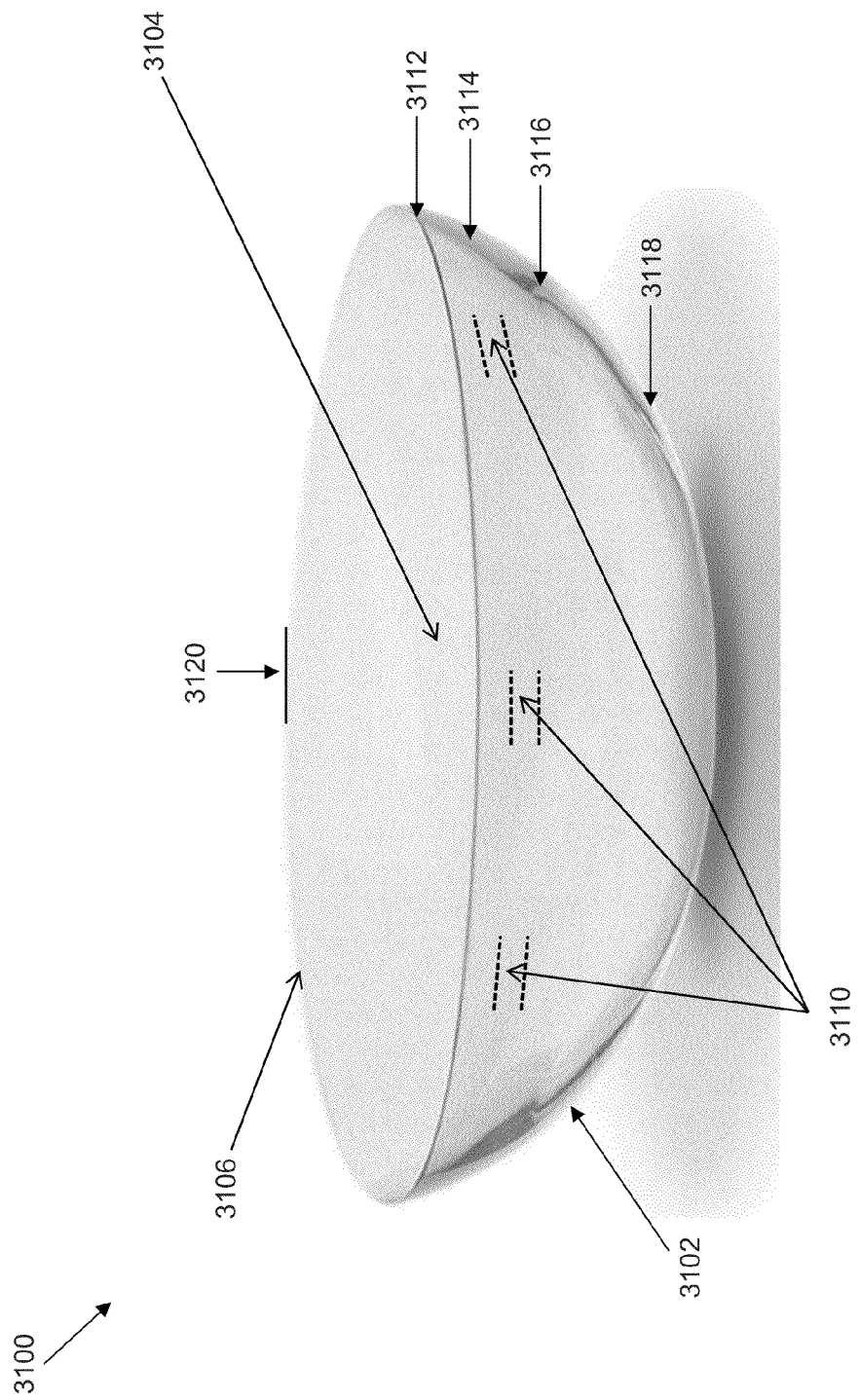
FIG. 31 shows a perspective view of a prosthesis according to one embodiment.

FIG. 31 shows a contact lens 3100 having a convex surface 3102, a concave surface 3104, and a peripheral edge 3106. An incremental thickness region 3110 is located on convex surface 3102. Incremental thickness region 3110 can be a continuous ring of increased thickness or a plurality of discontinuous partial rings or areas of increased thickness. Incremental thickness region 3110 is located interior of peripheral edge 3106 and has a thickness different from the rest of the contact lens 3100. The thickness profile of the lens is illustrated by a first thickness 3112, a second thickness 3114, a third thickness 3116, and a fourth thickness 3118. First thickness 3112, third thickness 3116, and fourth thickness 3118 are equal to the standard thickness of a conventional contact lens. Second thickness 3114, located in the incremental thickness region 3110, has a thickness greater than the standard thickness. Contact lens 3100 also has a small truncation 3120 on peripheral edge 3106.

Figure 32:
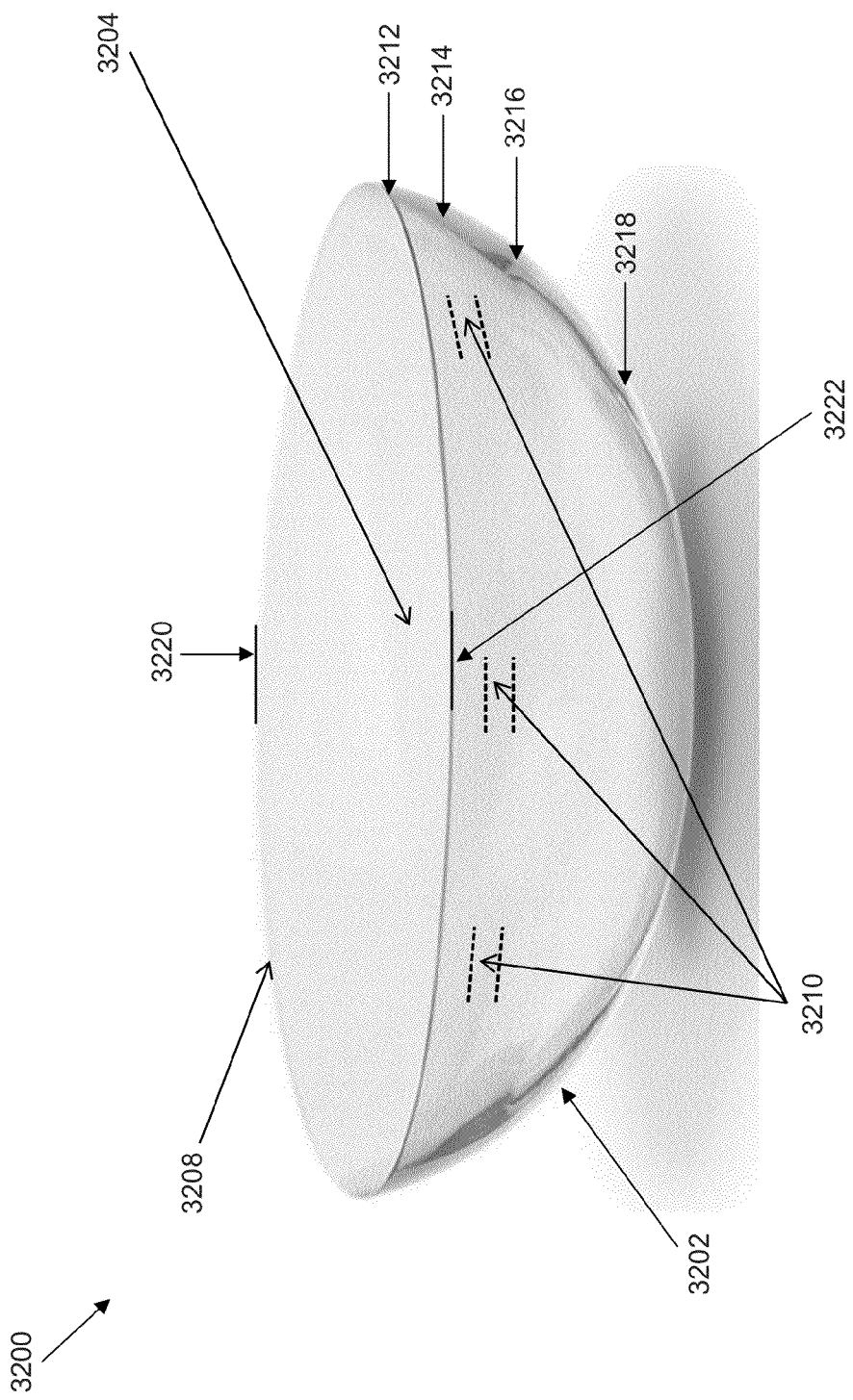
FIG. 32 shows a perspective view of a prosthesis according to one embodiment.

FIG. 32 shows a contact lens 3200 having a convex surface 3202, a concave surface 3204, and a peripheral edge 3206. An incremental thickness region 3210 is located on convex surface 3202. Incremental thickness region 3210 can be a continuous ring of increased thickness or a plurality of discontinuous partial rings or areas of increased thickness. Incremental thickness region 3210 is located interior of peripheral edge 3206 and has a thickness different from the rest of the contact lens 3200. The thickness profile of the lens is illustrated by a first thickness 3212, a second thickness 3214, a third thickness 3216, and a fourth thickness 3218. First thickness 3212, third thickness 3216, and fourth thickness 3218 are equal to the standard thickness of a conventional contact lens. Second thickness 3214, located in the incremental thickness region 3210, has a thickness greater than the standard thickness. Contact lens 3200 also has a small truncation 3220 and a prism ballast 3222 located on peripheral edge 3206. Small truncation 3220 is located opposite prism ballast 3222 on peripheral edge 3206.

Figure 33:
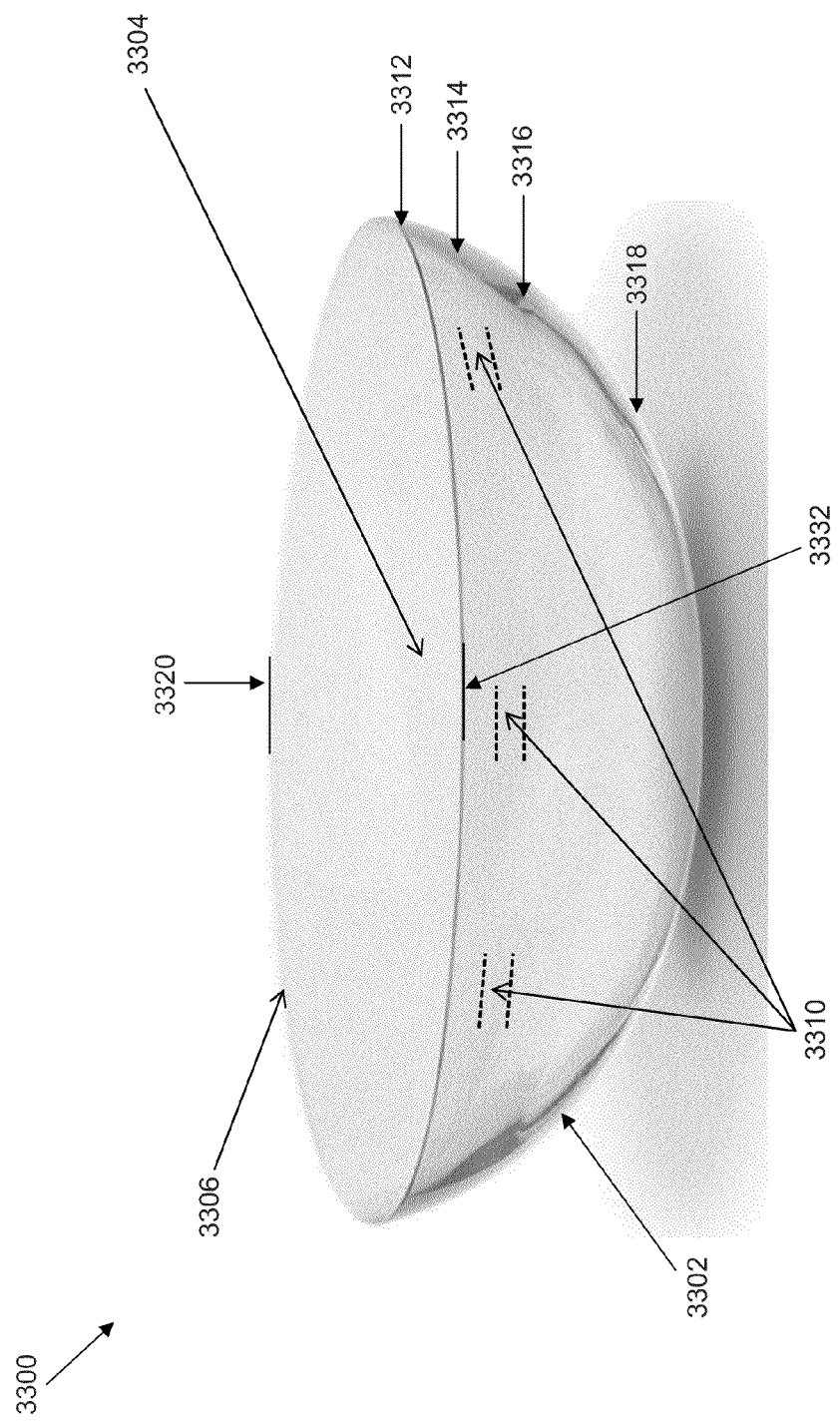
FIG. 33 shows a perspective view of a prosthesis according to one embodiment.

FIG. 33 shows a contact lens 3300 having a convex surface 3302, a concave surface 3304, and a peripheral edge 3306. An incremental thickness region 3310 is located on convex surface 3302. Incremental thickness region 3310 can be a continuous ring of increased thickness or a plurality of discontinuous partial rings or areas of increased thickness. Incremental thickness region 3310 is located interior of peripheral edge 3306 and has a thickness different from the rest of the contact lens 3300. The thickness profile of the lens is illustrated by a first thickness 3312, a second thickness 3314, a third thickness 3316, and a fourth thickness 3318. First thickness 3312, third thickness 3316, and fourth thickness 3318 are equal to the standard thickness of a conventional contact lens. Second thickness 3314, located in the incremental thickness region 3310, has a thickness greater than the standard thickness. Contact lens 3300 also has a small truncation 3320 and a small truncation/prism ballast 3322 on peripheral edge 3306. Small truncation 3320 is located opposite small truncation/prism ballast 3322 on peripheral edge 3306.

Figure 34:
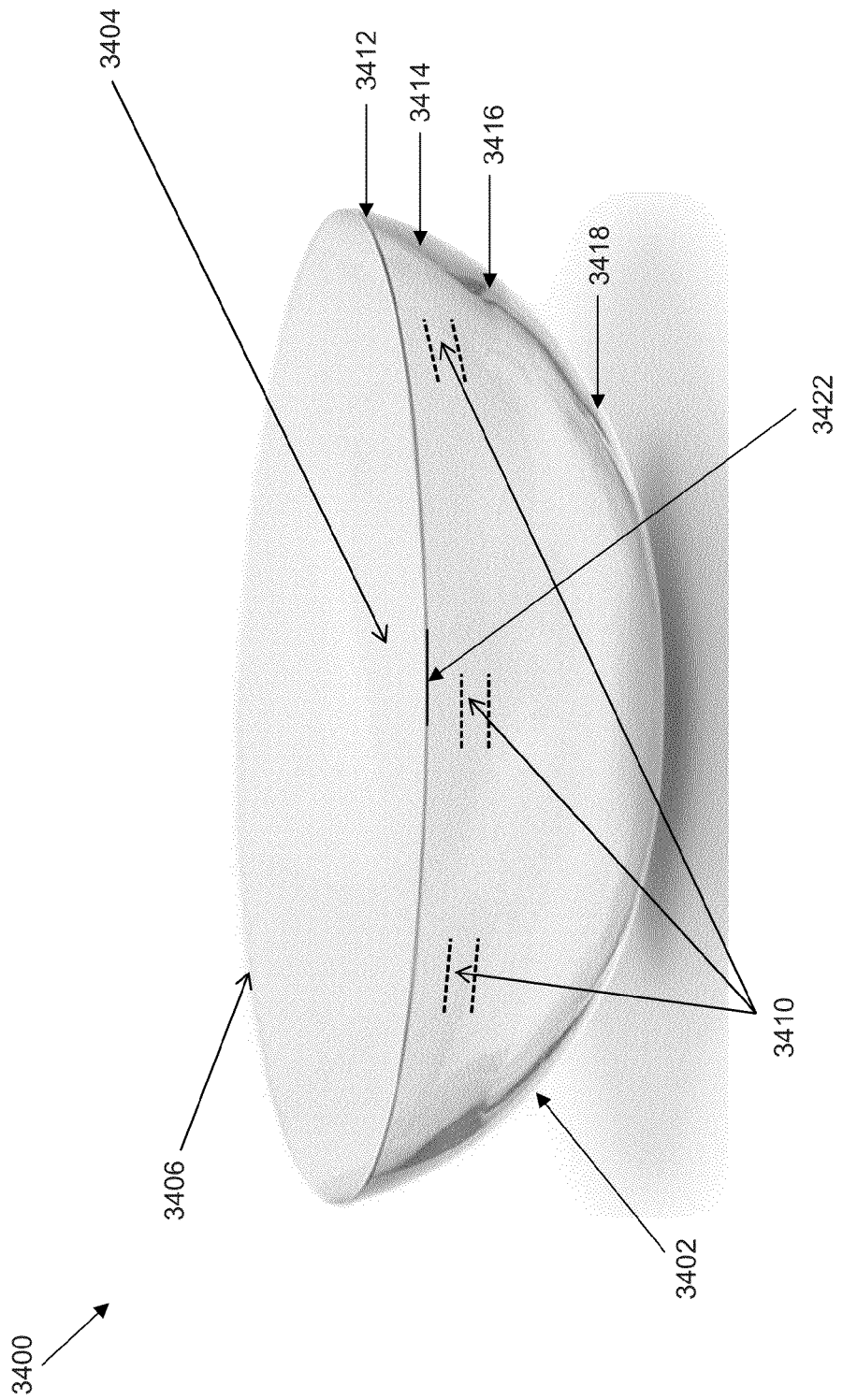
FIG. 34 shows a perspective view of a prosthesis according to one embodiment.

FIG. 34 shows a contact lens 3400 having a convex surface 3402, a concave surface 3404, and a peripheral edge 3406. An incremental thickness region 3410 is located on convex surface 3402. Incremental thickness region 3410 can be a continuous ring of increased thickness or a plurality of discontinuous partial rings or areas of increased thickness. Incremental thickness region 3410 is located interior of peripheral edge 3406 and has a thickness different from the rest of the contact lens 3400. The thickness profile of the lens is illustrated by a first thickness 3412, a second thickness 3414, a third thickness 3416, and a fourth thickness 3418. First thickness 3412, third thickness 3416, and fourth thickness 3418 are equal to the standard thickness of a conventional contact lens. Second thickness 3414, located in the incremental thickness region 3410, has a thickness greater than the standard thickness. Contact lens 3400 also has a small truncation/prism ballast 3422 located on peripheral edge 3406.

Figure 35:
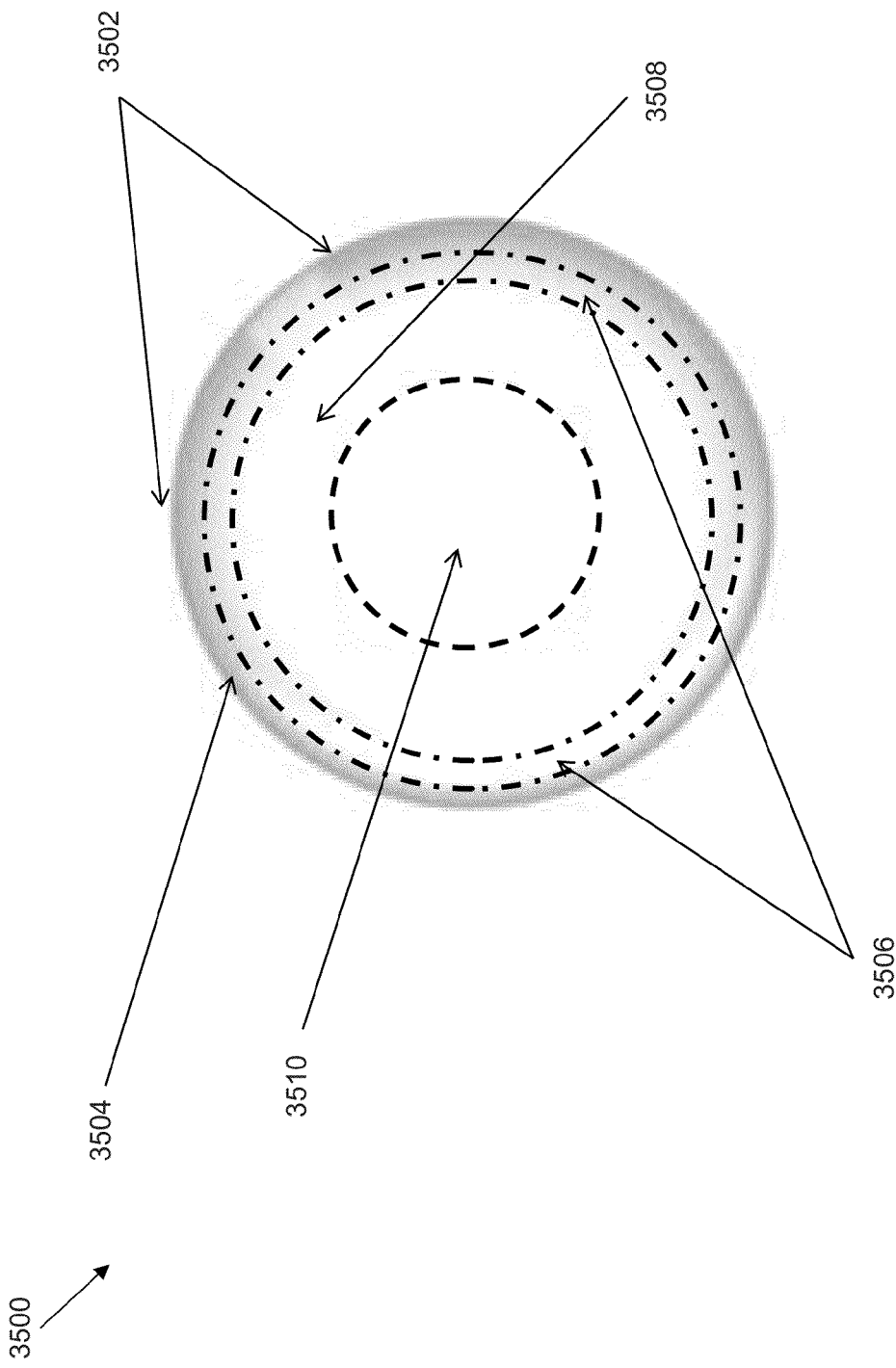
FIG. 35 shows an aerial view of a prosthesis according to one embodiment.

FIGS. 35-38 show aerial views of a plurality of contact lenses having various types of aperture widening zones. While FIGS. 35-38 all illustrate contact lenses it will be appreciated that the same features described in reference to FIGS. 35-38 could be incorporated onto a scleral ring. FIG. 35 shows a contact lens 3500 having a peripheral edge 3502 and pupil zone 3510. Pupil zone 3510 may have optical power or may be devoid of optical power and has a standard thickness and convex curve as that of a conventional contact lens having a specified optical power or lack thereof. Located between peripheral edge 3502 and pupil zone 3510 is an incremental thickness region 3506. It should be pointed out that the incremental thickness region (aperture widening zone) 3506 can start at or adjacent to the outer edge of the prosthesis. While a single ring is shown for incremental thickness region 3506 it is appreciated that there may be multiple rings or partial rings. Surrounding incremental thickness region 3506 and located between peripheral edge 3502 and incremental thickness region 3506 is a peripheral region 3504. Peripheral region 3504 has thickness and curvature equal to the standard thickness and curvature of a conventional contact lens. An internal region 3508 is located between pupil zone 3510 and incremental thickness region 3506. Internal region 3508 has a thickness and curvature equal to that of a conventional contact lens.

Figure 36:
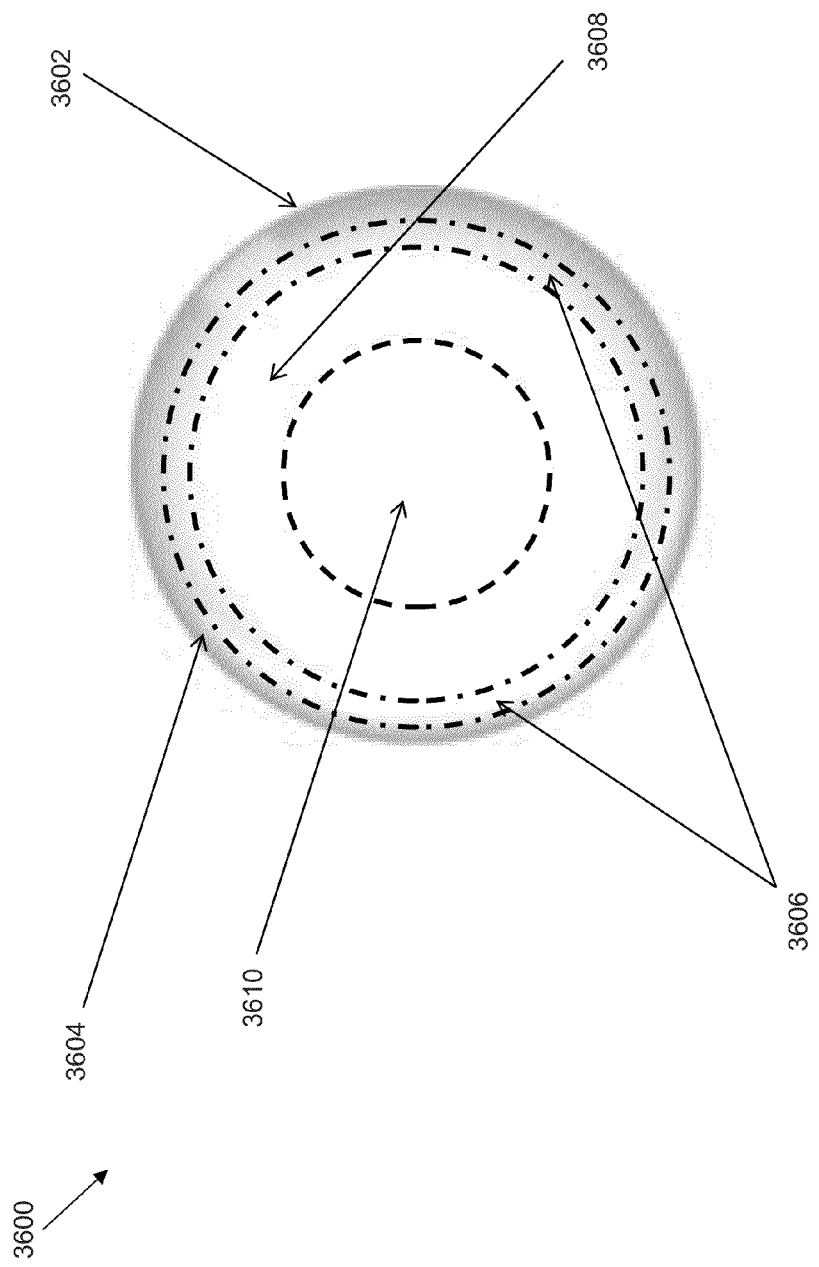
FIG. 36 shows an aerial view of a prosthesis according to one embodiment.

FIG. 36 shows a contact lens 3600 having a peripheral edge 3602 and pupil zone 3610. Pupil zone 3610 may have optical power or may be devoid of optical power and has a standard surface friction, thickness, and convex curvature as that of a conventional contact lens having a specified optical power or lack thereof. Located between peripheral edge 3602 and pupil zone 3610 is an increased surface friction region 3606. Increased surface friction region 3606 includes a textured surface that increases surface friction. The textured surface can be created by, but not limited to, a different material, dimples, bumps, surfaces irregularities, any change in surface topography, or any combination thereof. While a single ring is shown for increased surface friction region (aperture widening zone) 3606 it is appreciated that there may be multiple rings. Surrounding increased surface friction region 3606 and located between peripheral edge 3602 and increased surface friction region 3606 is a peripheral region 3604. Peripheral region 3604 has a surface friction equal to the standard surface friction of a conventional contact lens. An internal region 3608 is located between pupil zone 3610 and increased surface friction region 3606. Internal region 3608 has a surface friction, thickness, and curvature equal to that of a conventional contact lens.

Figure 37:
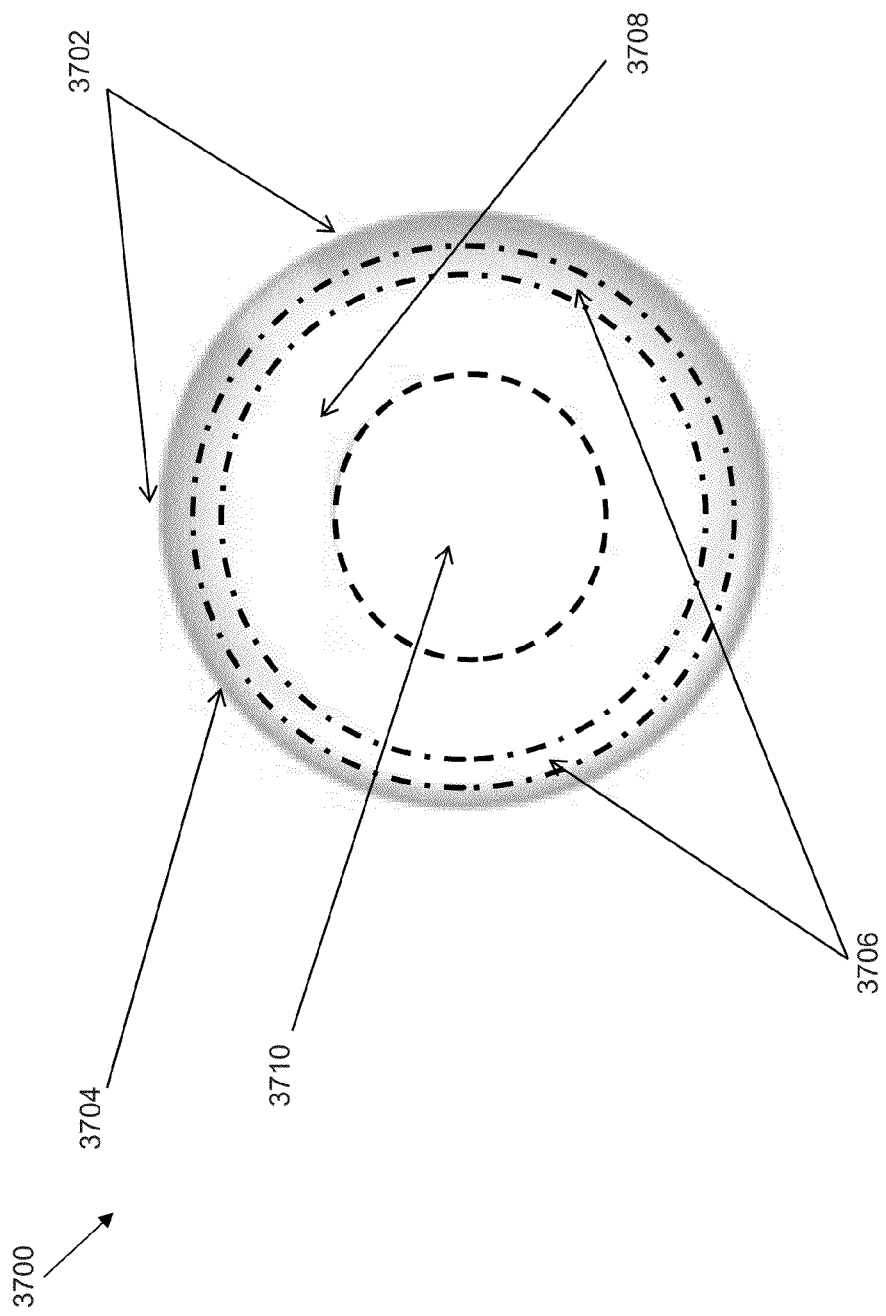
FIG. 37 shows an aerial view of a prosthesis according to one embodiment.

FIG. 37 shows a contact lens 3700 having a peripheral edge 3702 and pupil zone 3710. Pupil zone 3710 may have optical power or may be devoid of optical power and has a standard surface friction, thickness, and convex curvature as that of a conventional contact lens having a specified optical power or lack thereof. Located between peripheral edge 3702 and pupil zone 3710 is an incremental thickness and increased surface friction region 3706. Incremental thickness and increased surface friction region (aperture widening zone) 3706 includes an increased thickness and textured surface that increase surface friction. The textured surface can be created by, but not limited to, a different material, surface treatment, dimples, bumps, surfaces irregularities, any change in surface topography, or any combination thereof. While a single ring is shown for incremental thickness and increased surface friction region 3706 it is appreciated that there may be multiple rings. Surrounding incremental thickness and increased surface friction region 3706 and located between peripheral edge 3702 and incremental thickness and increased surface region 3706 is a peripheral region 3704. Peripheral region 3704 has a thickness and surface friction equal to the standard thickness and surface friction of a conventional contact lens. An internal region 3708 is located between pupil zone 3710 and increased surface friction region 3706. Internal region 3708 has a thickness, surface friction, and curvature equal to that of a conventional contact lens.

Figure 38:
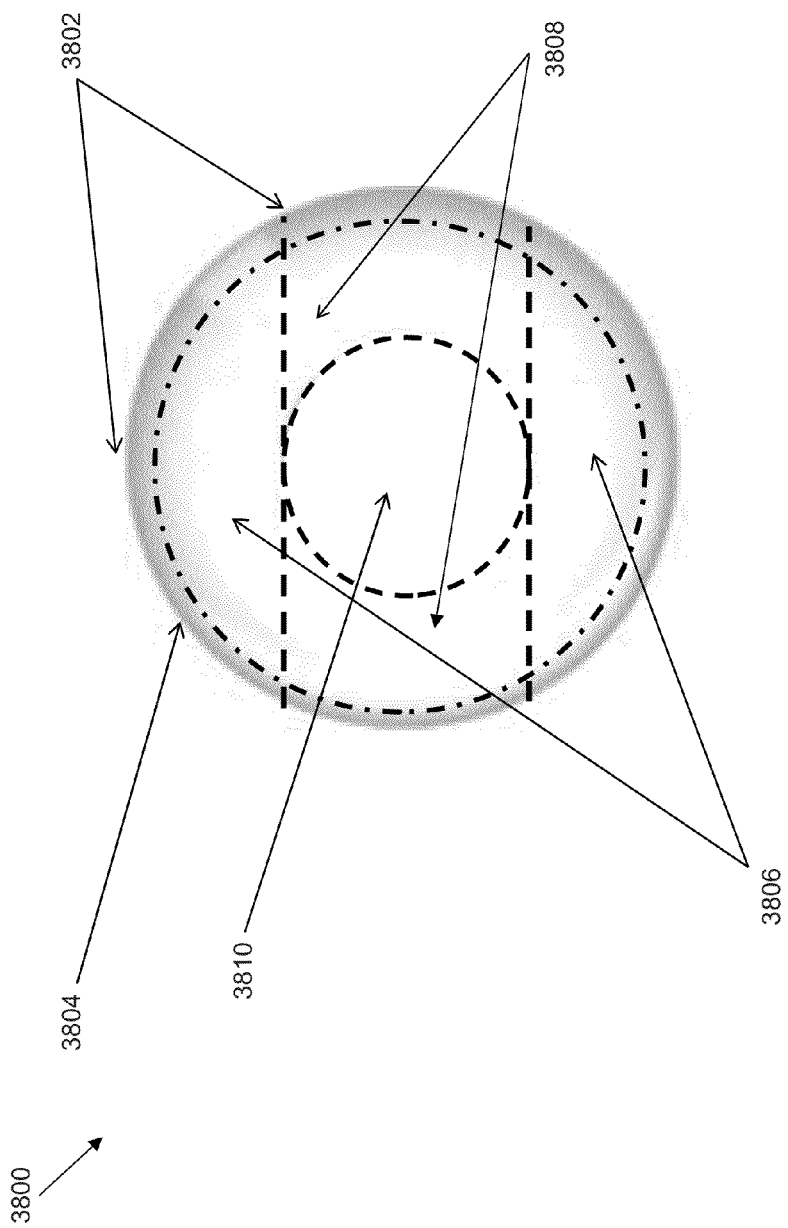
FIG. 38 shows an aerial view of a prosthesis according to one embodiment.

FIG. 38 shows a contact lens 3800 having a peripheral edge 3802 and a pupil zone 3810. Pupil zone 3810 may have optical power or may be devoid of optical power and has a standard thickness and convex curvature as that of a conventional contact lens having a specified optical power or lack thereof. Pupil zone 3810 can also include an astigmatic optical power. Located above and below pupil zone 3810 are two incremental thickness regions 3806. It should be noted that each of the two incremental thickness regions 3806 (aperture widening zones) will have an outer slope, inner slope and point of maximum thickness delta/maximum increased thickness. Each incremental thickness region 3806 has a hemispherical shape. Contact lens 3800 also includes two internal regions 3808 located on either side of pupil zone 3810. Each internal region 3808 has a thickness and curvature equal to a standard thickness and curvature of a conventional contact lens. Surrounding the periphery of the lens is a peripheral region 3804 which also has a thickness and curvature equal to a standard thickness and curvature of a conventional contact lens. However, it should be noted that each of the two incremental thickness regions could start at or adjacent to the outer edge of the contact lens. It will be appreciated that incremental thickness regions 3806 can also include a textured surface that increases surface friction. Additionally, incremental thickness regions 3806 can be replaced with increased surface friction regions having a textured surface and having conventional thickness and curvature.

FIGS. 39A-E illustrates the surface profile of a contact lens 3900 according to one embodiment. Contact lens 3900 has an optical power of 0.0+/−1.00 D. As seen in FIG. 39A, contact lens 3900 includes a first surface 3904, a second surface 3906, third surface 3908, and a fourth surface 3910. First surface 3904 has a radius of curvature ranging between 6.50 mm and 9.5 mm. Second surface 3906 exemplifies an incremental thickness region in the form of a bump (aperture widening zone). The radius of curvature of second surface 3906 ranges between 4.50 mm and 7.50 mm. Second surface 3906 can have a width between 2.0 mm and 4.0 mm. Third surface 3908 has a radius of curvature ranging between 6.50 mm and 9.50 mm. Fourth surface 3910 is located on the outer most periphery of contact lens 3900 and has a radius of curvature ranging from 2.0 mm and 8.0 mm. The overall diameter of contact lens 3900 can range from 11.0 mm to 16.5 mm. FIG. 39B shows a side view of contact lens 3900. FIG. 39C shows a cross-section of contact lens 3900 along line 3902 in FIG. 39A. FIG. 39D shows the convex surface of contact lens 3900 and FIG. 39E shows the concave surface of contact lens 3900.

Figure 40:
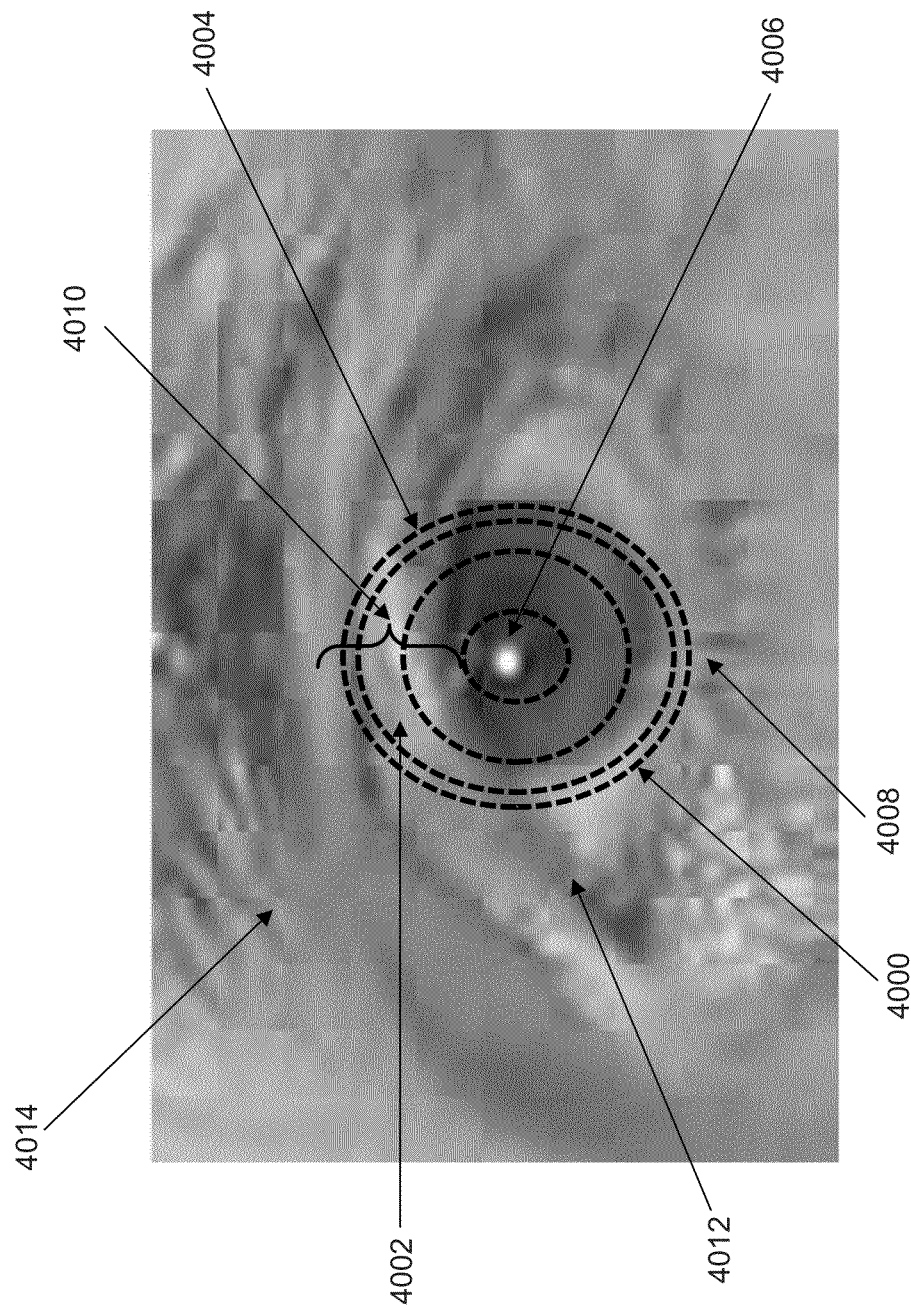
FIG. 40 shows a prosthesis according to one embodiment superimposed on an eye.

FIG. 40 shows a contact lens 4000 having a spherical optical power superimposed on an eye 4014. Eye 4014 has an upper lid 4012 and a lower lid 4008. Contact lens 4000 includes an area of incremental thickness (aperture widening zone) 4002, a pupil zone 4006, and a peripheral edge 4004. It can be seen in FIG. 40 that contact lens 4000 has an area 4010 that fits under upper lid 4012. Included in area 4010 is part of incremental thickness region 4002.

Figure 41:
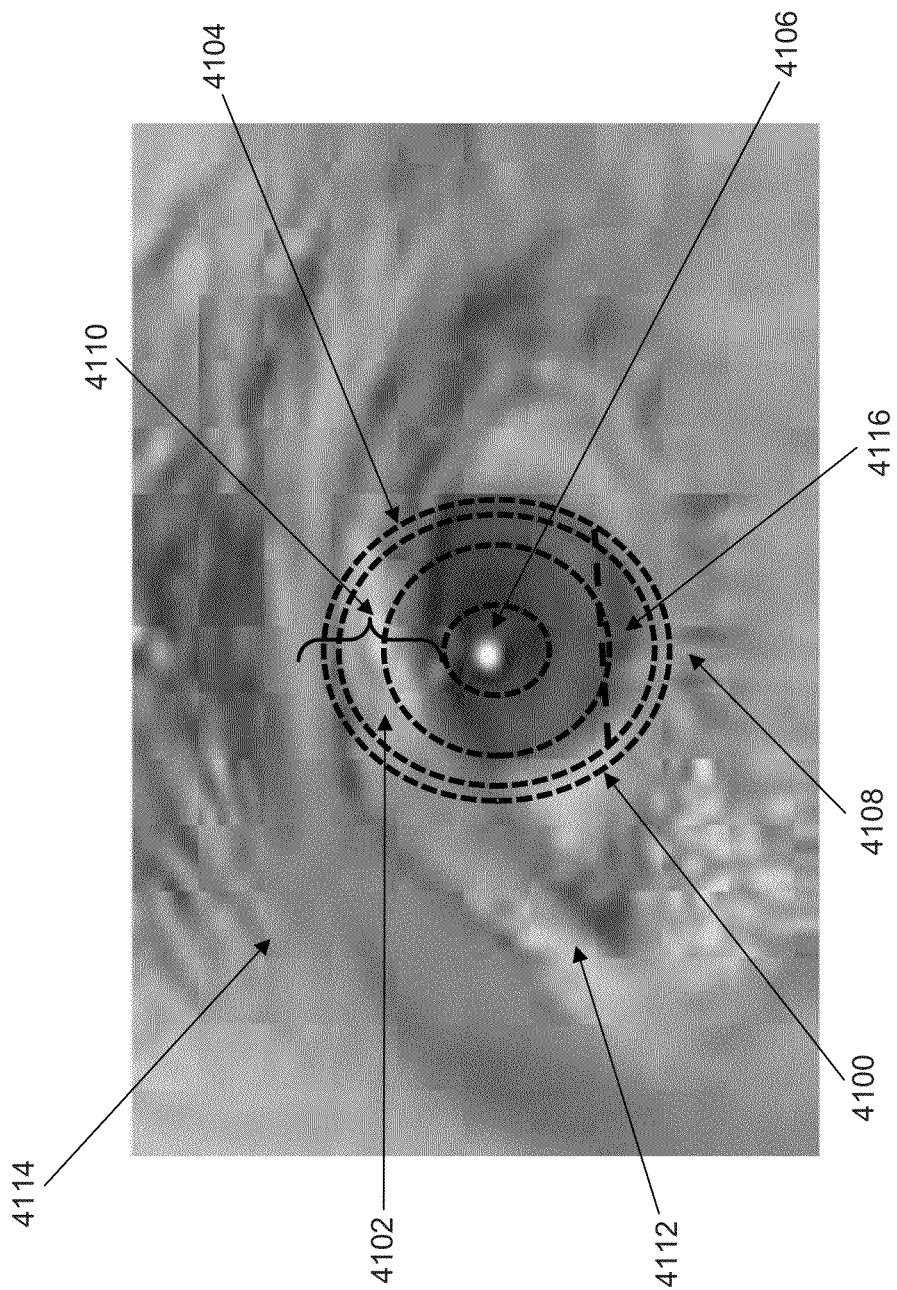
FIG. 41 shows a prosthesis according to one embodiment superimposed on an eye.

FIG. 41 shows a contact lens 4100 having an astigmatic optical power superimposed on an eye 4114. Eye 4114 has an upper lid 4112 and a lower lid 4108. Contact lens 4100 includes an incremental thickness region (aperture widening zone) 4102, a pupil zone 4106, and a peripheral edge 4104. It can be seen in FIG. 41 that contact lens 4100 has an area 4110 that fits under upper lid 4112. Included in area 4110 is part of incremental thickness region 4102. Contact lens 4100 also has a weighted/stabilization zone 4116 located on the bottom.

Figure 42:
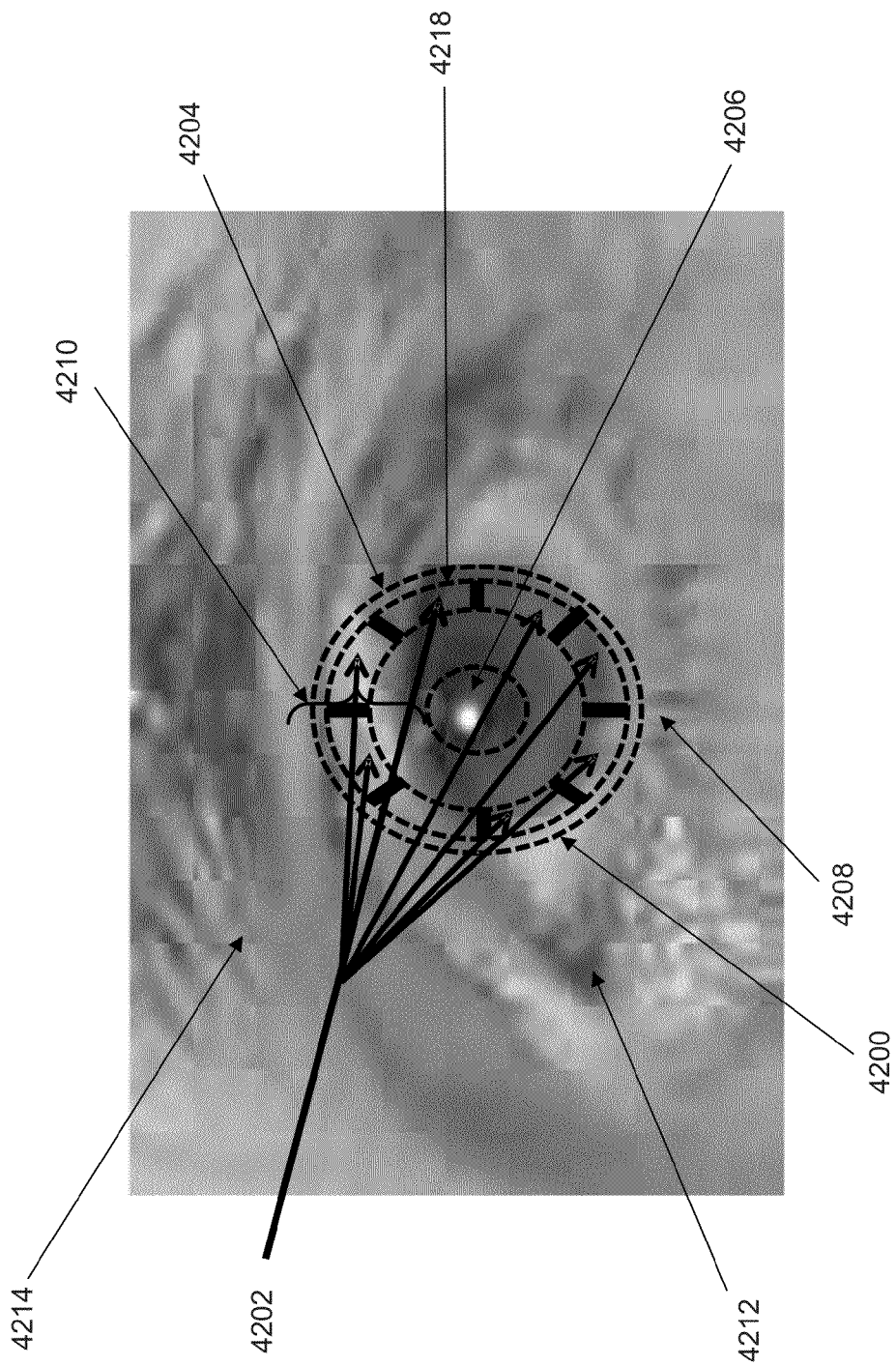
FIG. 42 shows a prosthesis according to one embodiment superimposed on an eye.

FIG. 42 shows a contact lens 4200 having a spherical optical power superimposed on an eye 4214. Eye 4214 has an upper lid 4212 and a lower lid 4208. Contact lens 4200 includes an incremental thickness region (aperture widening zone) 4218 having a plurality of partial rings 4202, a pupil zone 4206, and a peripheral edge 4204. It can be seen in FIG. 42 that contact lens 4200 has an area 4210 that fits under upper lid 4212. Included in area 4210 is a plurality of partial rings 4202 located in incremental thickness region 4218.

Figure 43:
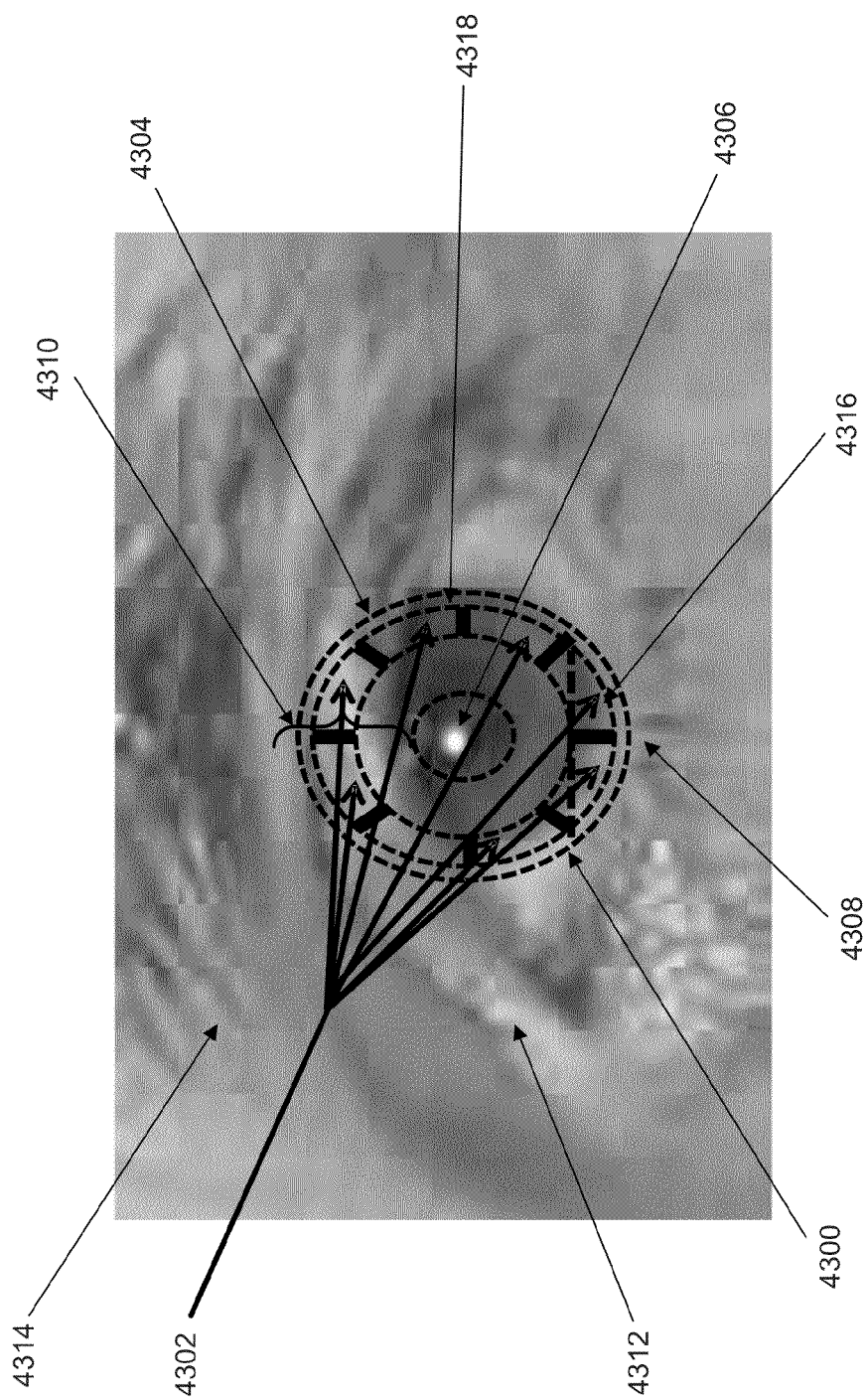
FIG. 43 shows a prosthesis according to one embodiment superimposed on an eye.

FIG. 43 shows a contact lens 4300 having a spherical optical power superimposed on an eye 4314. Eye 4314 has an upper lid 4312 and a lower lid 4308. Contact lens 4300 includes an incremental thickness region (aperture widening zone) 4318 having a plurality of partial rings 4302, a pupil zone 4306, and a peripheral edge 4304. It can be seen in FIG. 43 that contact lens 4300 has an area 4310 that fits under upper lid 4312. Included in area 4310 is a plurality of the partial rings 4302 located in incremental thickness region 4318. Contact lens 4300 also has a weighted/stabilization zone 4316 located on the bottom.

Figure 44:
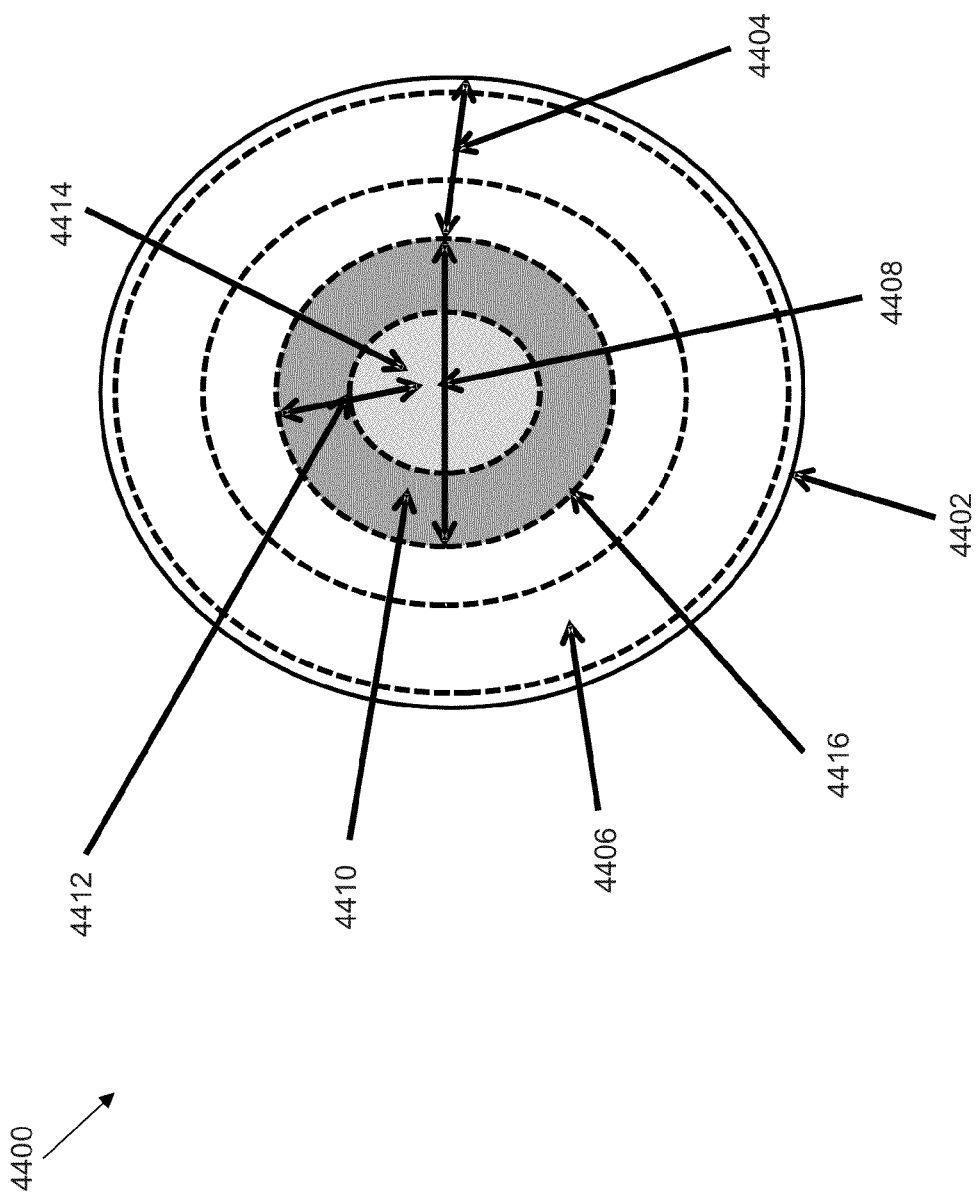
FIG. 44 shows a hybrid contact lens according to one embodiment.

FIG. 44 shows an embodiment of a hybrid multifocal contact lens 4400. Contact lens 4400 includes a peripheral edge 4402 surrounding a soft skirt 4404. Soft skit 4404 includes an incremental thickness region (aperture widening zone) 4406. A junction 4416 is located at the periphery of incremental thickness region 4406. Junction 4416 connects incremental thickness region 4406 to a gas permeable rigid zone 4408. Gas permeable rigid zone 4408 has a continuous graduation of power 4412 and includes aspheric distance zone 4410 and aspheric near zone 4414. While the embodiment of FIG. 44 shows incremental thickness region 4406 located near peripheral edge 4402 it can be located anywhere adjacent to or peripheral to gas permeable rigid zone 4408. By this it is meant that incremental thickness region 4406 can be located adjacent to or outside of 3.0 mm of a geometric center of hybrid contact lens 4400.

Figure 45:
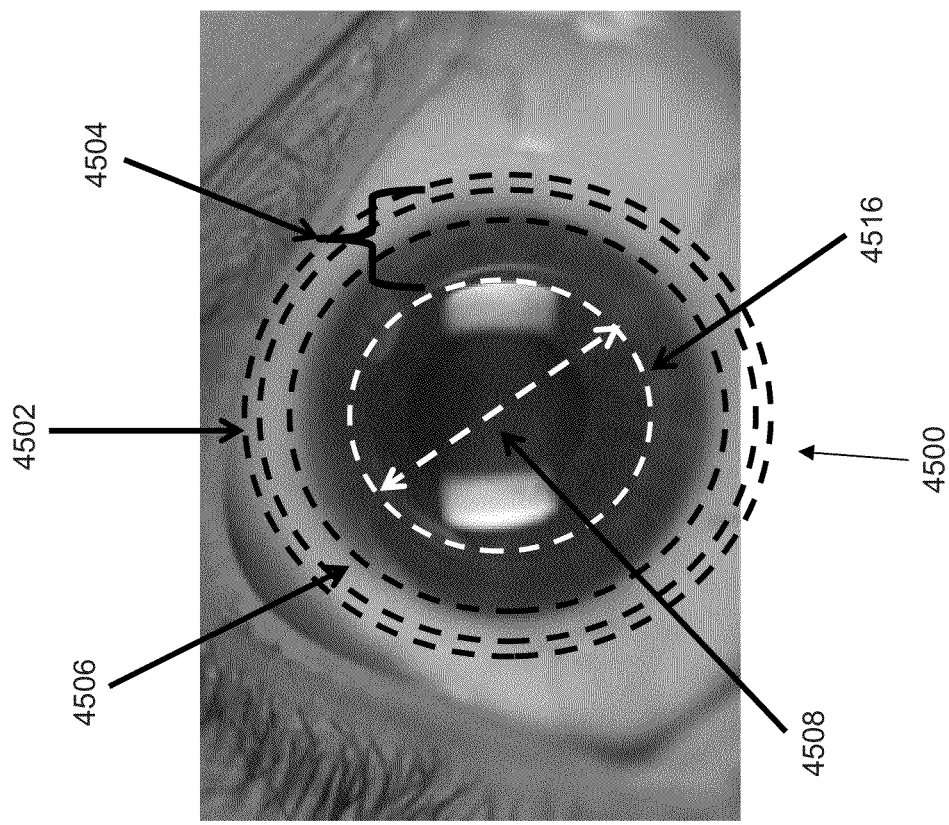
FIG. 45 shows a hybrid contact lens according to one embodiment.

FIG. 45 shows an embodiment of a hybrid contact lens 4500 superimposed on an eye. Contact lens 4500 includes a peripheral edge 4502 surrounding a soft skirt 4504. Soft skit 4504 includes an incremental thickness region 4506 (aperture widening zone) and has a junction 4516 located on its peripheral edge. Junction 4516 connects soft skit 4504 to a gas permeable rigid zone 4508. Gas permeable rigid zone 4508 can include a spherical optical power or an astigmatic optical power.

Figure 46:
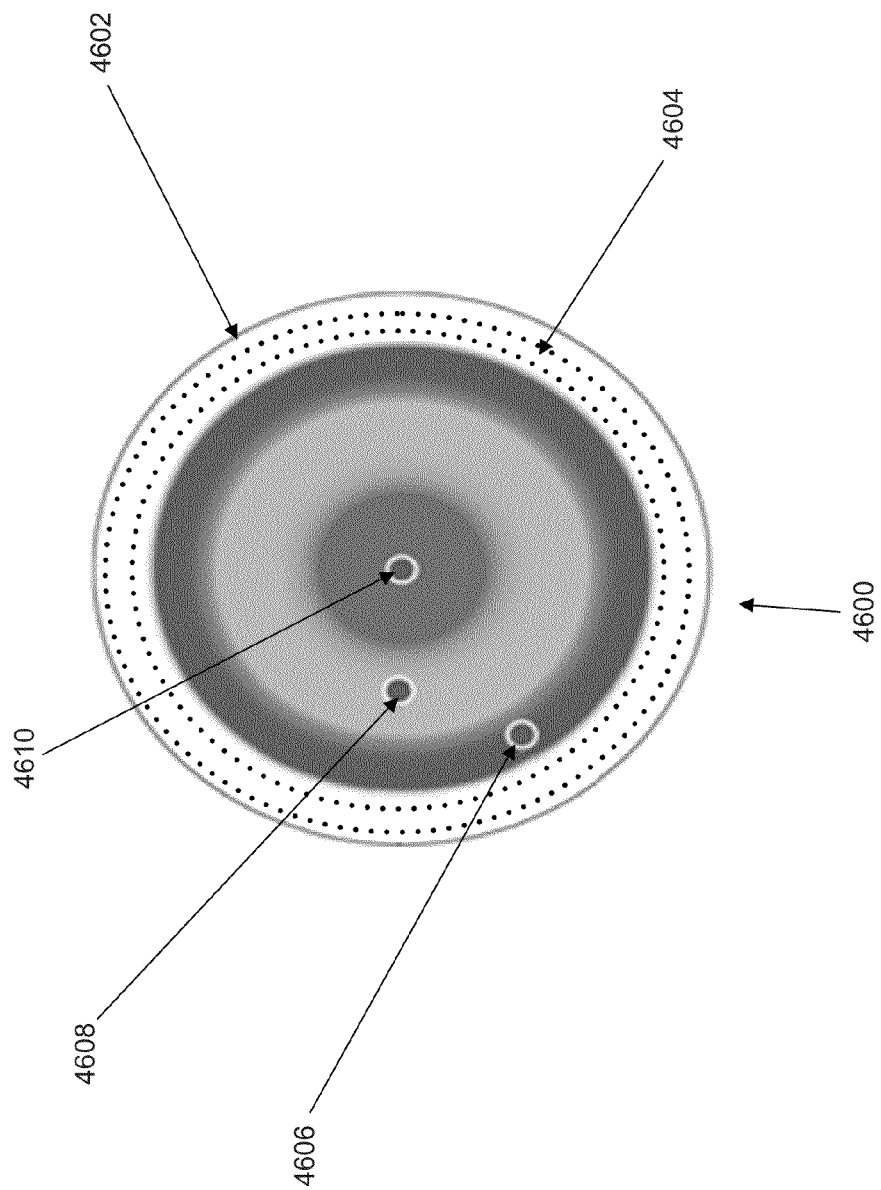
FIG. 46 shows a hybrid contact lens according to one embodiment.

FIG. 46 shows an embodiment of a soft multifocal contact lens 4600. Contact lens 4600 includes a peripheral edge 4602, an area of incremental thickness (aperture widening zone) 4604, a near distance zone 4606 (illustrated as the ring that circles the geometrical center of the contact lens), an intermediate zone 4608 (illustrated as the ring that circles the geometrical center of the contact lens), and a distance zone 4610 (illustrated as the larger central dark area which is surrounded by intermediate zone 4608).

Figure 47:
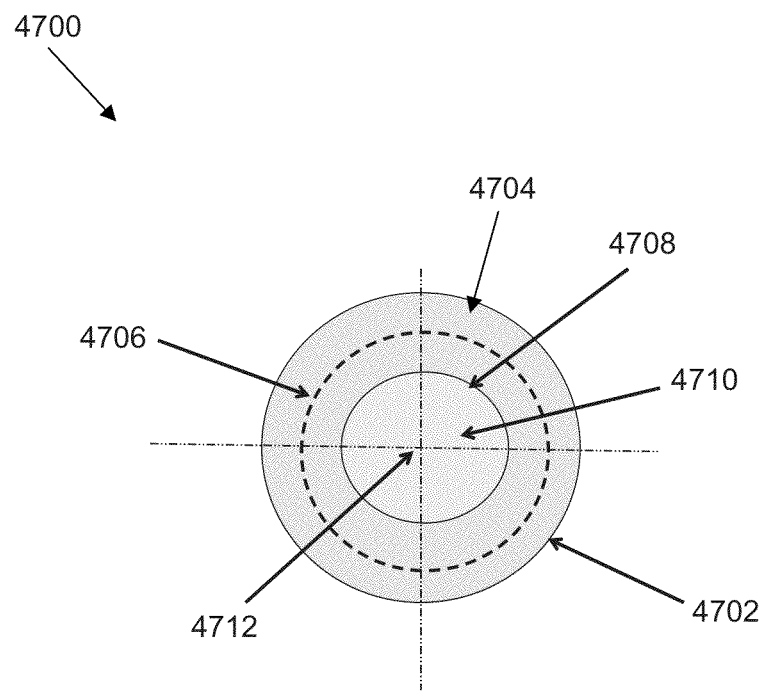
FIG. 47 shows a reverse hybrid contact lens according to one embodiment.

FIG. 47 shows an embodiment of a reverse hybrid contact lens 4700. Contact lens 4700 includes a peripheral edge 4702 and a geometric center 4712. A rigid outer skirt 4704 surrounds a soft center 4710 and includes an incremental thickness region (aperture widening zone) 4706. Junction 4708 is located between rigid outer skit 4704 and soft center 4710.

Patient Selection Process for Fitting the Prosthesis:

The prosthesis provides the significant cosmetic enhancement/widening of the palpebral fissure of the wearer's eye when fitted on an eye that has an upper lid margin within 2 mm to 3 mm or less of the upper edge of the pupil and/or a lower lid margin is within 2 mm to 3 mm or less of the lower edge of the pupil. Another way of establishing patient selection for the prosthesis is the selection of any eye where the upper or lower lid, in a resting location with the lids open, covers the upper and/or lower limbal area of the eye.

The embodiments disclosed herein also teach an instrument that projects an image of known diameters onto the skin and facial eye region of a potential wearer. The instrument allows for taking a photo of the projected image on the eye and the adjacent facial region of the potential wearer. By doing this it is possible to quickly understand the appropriate diameter contact lens or scleral ring needed to provide the best palpebral widening effect. In some embodiments infrared light is used to project light onto the eye of the wearer so to minimize any constriction of the wearer's pupil. In other embodiments low levels of visible light are projected. In still other embodiments an infra-red camera is used.

The process further contemplates a fitting set of the prosthesis whereby in the case of the contact lens prosthesis a set of rings or series of dots or lines are painted or affixed to the contact lens; each dot, line or ring by way of example only being 1 mm less diameter than the outermost adjacent dot, line or ring. This then allows an eye care professional to visually determine quickly when the prosthesis is tried on the eye of the wearer which contact lens provides the maximum aperture widening. The professional can also then simply indicate the number of lines or rings present in the open aperture of various trial lenses thus allowing selection of the one that presents the greatest number of lines or rings within the aperture of the wearer's eye.

In a first fitting method embodiment the following technique is followed in fitting the prosthesis that is taught herein:
  #1) Take a photograph of intended wearer's eye or eyes while patient/intended wearer is relaxed without smiling;
  #2) Display or print photograph;
  #3) Measure the natural palpebral fissure or fissures as shown in the displayed or printed photograph;
  #4) Choose a trial prosthesis that provides good centration and has an overall outer diameter that is within the range of 1 mm to 10 mm wider than the palpebral fissure just measured of the intended wearer being fit, however in most cases it will be 2 mm to 4 mm wider;
  #5) Choose a prosthesis to be prescribed and/or delivered to patient after viewing the appearance of wearer's eye (this can be done solely by the eye care professional and/or by feedback from the patient being fit);
  #6) Repeat the appropriate steps for fitting the second eye of the intended wearer or patient.

In a Second fitting method embodiment the following technique is followed in fitting the prosthesis that is taught herein:
  #1) Measure the natural palpebral fissure of the patient's/intended wearer's eye or eyes while patient/intended wearer is relaxed without smiling;
  #2) Choose a trial prosthesis that provides good centration and has an overall outer diameter that is within the range of 1 mm to 10 mm wider than the palpebral fissure just measured of the intended wearer being fit, however in most cases it will be 2 mm to 4 mm wider;
  #3) Choose a prosthesis to be prescribed and/or delivered to a patient after viewing the appearance of wearer's eye (this can be done solely by the eye care professional and/or by feedback from the patient being fit);
  #4) Repeat the appropriate steps for fitting the second eye of the intended wearer or patient.

In a third fitting method embodiment the following technique is followed in fitting the prosthesis that is taught herein:
  #1) Take a photograph of intended wearer's eye or eyes while patient/intended wearer is relaxed without smiling;
  #2) Display or print photograph;
  #3) Measure the natural palpebral fissure or fissures as shown in the displayed or printed photograph;
  #4) Fit a prosthesis out of inventory or order a prosthesis that provides good centration and has an overall outer diameter that is within the range of 1 mm to 10 mm wider than the palpebral fissure just measured of the intended wearer being fit, however in most cases it will be 2 mm to 4 mm wider.

In a Fourth fitting method embodiment the following technique is followed in fitting the prosthesis that is taught herein:
  #1) Measure the natural palpebral fissure of the patient's/intended wearer's eye or eyes while patient/intended wearer is relaxed without smiling;
  #2) Fit a prosthesis out of inventory or order a prosthesis that provides good centration and has an overall outer diameter that is within the range of 1 mm to 10 mm wider than the palpebral fissure just measured of the intended wearer being fit, however in most cases it will be 2 mm to 4 mm wider.

In a Fifth fitting method embodiment the following technique is followed in fitting the prosthesis that is taught herein:
  #1) Fit the prosthesis out of inventory or order a prosthesis that provides good centration and has an overall outer diameter that is within the range of 1 mm to 10 mm wider than the palpebral fissure just measured of the intended wearer being fit, however in most cases it will be 2 mm to 4 mm wider.

Figure 48:
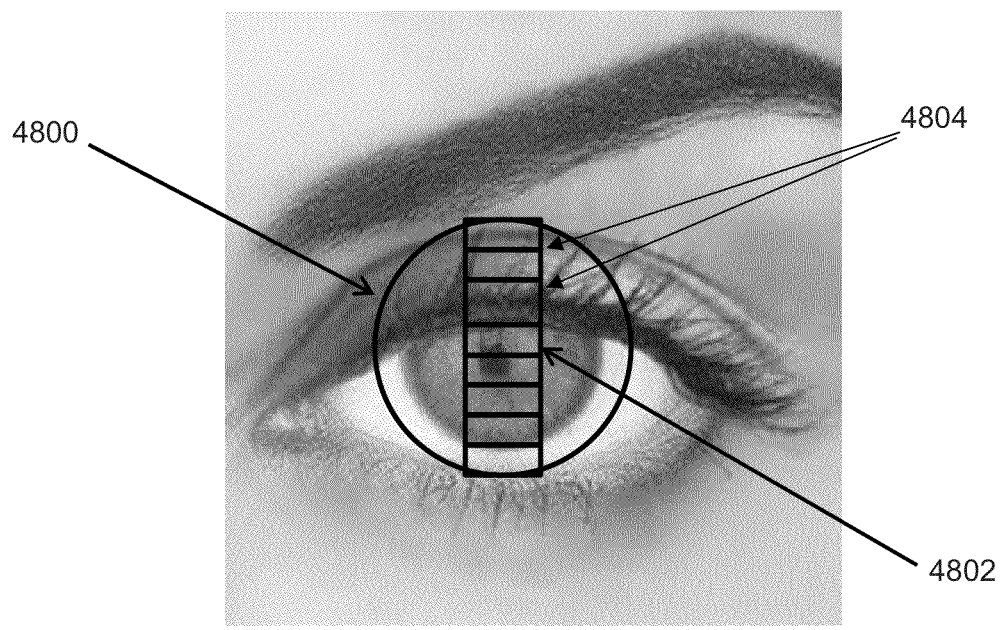
FIG. 48 shows an example of a scale used for fitting a prosthesis having an aperture widening zone.

FIG. 48 shows an example of a method for fitting a prosthesis as described herein. As seen in FIG. 48, an image 4800 is projected onto an individual's eye. Image 4800 includes a scale 4802 with a plurality of markings 4804. Marking 4804 are used to measure the individual's palpebral fissure and used to determine the diameter of a prosthesis that will raise the upper lid, or depress the lower lid, thereby widening the individual's palpebral fissure.

It should be understood that any and all known contact lens treatments, colors, custom color designs (including color designs, such as by way of example only a limbal ring, color ring, or color accent, imparted on the prosthesis to increase the appearance of the size of the outer limbus thus making the wearer's eye appear larger), coatings, materials, filtering of specific wavelength (lengths) of light, contact lens designs, shapes, optical powers including plano, static or dynamic focusing contact lenses, any known optical powers required for astigmatic, spherical, and presbyopic correction can be considered to apply to the prosthesis (contact lens or scleral ring) described herein. By way of example only when the prosthesis is in the form of a contact lens the contact lens can be; single vision with spherical only optical power, single vision with sphero-cylinder optical power, multifocal with spherical only optical power, multifocal with sphero-cylinder optical power. A prosthesis in the form of a scleral ring would not have optical power and will not be considered single vision or multifocal.

It should be understood that the embodiments as disclosed herein cover any means by which a soft contact lens or hybrid contact lens or scleral ring increases the size of the wearer's palpebral fissure by way of "one or more" of the following features of the contact lens, by way of example only; "incremental thickness region (aperture widening zone)", increased overall thickness, increased edge thickness, increased overall diameter, localized area of increased thickness, increased convex surface friction, localized area of increased convex surface friction, increased partial area of raised thickness on convex surface, regressive thickness zone, convex surface treatment (material and/or texture), truncation to superior edge of lens, truncation to the inferior edge of the lens, truncation to the superior and inferior edge of the lens, increased thickness of the edge of the lens, (partial or complete) band (bands) or ring (rings), dome (domes), segment (segments) of increased thickness on the convex surface of the contact lens external to the pupil zone, and increased base curve fit. This list is not intended to be limiting.

In some, but not all, embodiments the prosthesis has an increased thickness region superior to the pupil zone.

In some, but not all, embodiments the prosthesis has an increased thickness region inferior to the pupil zone.

In some, but not all, embodiments the prosthesis has an increased thickness region superior and inferior to the pupil zone.

In some, but not all, embodiments the prosthesis provides truncation and/or weighting to stabilize the prosthesis.

In some, but not all, embodiments the lens edge is that of a conventional prosthesis thickness and edge.

In some, but not all embodiments, the lens edge has a thicker overall thickness and edge compared to traditional contact lenses.

It is important to note that the increased thickness of the contact lens prosthesis (whether within the pupil zone or external to the pupil zone) in most, but not all embodiments, does not alter the desired prescription or optical power of the portion of the contact lens that focuses light on the retina of the wearer of the contact lens.

In some embodiments one of a soft or hybrid contact lens is of spherical optical power, however the area peripheral to the pupilary zone is configured like that of a minus aspheric toric lens having an axis of 180 (+/−20 degrees) in terms of thickness, meaning the thickness above and below the pupilary zone is thicker than normal.

In other embodiments one of a soft or hybrid contact lens is of spherical optical power, however the area peripheral to the pupilary zone is configured like that of one of a soft or hybrid contact lens in terms of thickness, with the exception of this peripheral area being of increased thickness compared to that of a conventional/traditional soft or hybrid spherical power contact lens for the same optical power, diameter and base curve.

In some embodiments one of a soft or hybrid contact lens comprises astigmatic optical power, and the area peripheral to the pupilary zone is configured like that of a minus aspheric toric lens having an axis of 180 (+/−20 degrees) in terms of thickness, meaning the thickness "above and below" the pupilary zone is thicker than normal for a typical astigmatic correcting soft or hybrid contact lens.

Some embodiments contemplate spherical lenses with no optical power axis being such that the area superior and inferior to the pupil zone of the soft contact lens or hybrid contact lens is thicker than would be expected for a soft or hybrid contact lens having such a spherical or astigmatic optical power.

Some embodiments contemplate astigmatic lenses having an optical axis being such that the area superior and inferior to the pupil zone of the soft contact lens or hybrid contact lens is thicker than would be expected for a soft or hybrid contact lens having such a spherical or astigmatic optical power.

Some embodiments contemplate an incremental thickness region (zone, area) or a regressive thickness region (zone, area) located on the convex surface of the prosthesis that is rotationally symmetrical.

Some embodiments contemplate an incremental thickness region (zone, area) or a regressive thickness region (zone, area) located on the convex surface of the prosthesis that is rotationally asymmetrical.

Some embodiments contemplate an incremental thickness region (zone, area) or a regressive thickness region (zone, area) located on the convex surface of the prosthesis that is non-rotationally symmetrical.

Some embodiments contemplate an incremental thickness region (zone, area) or a regressive thickness region (zone, area) located on the convex surface of the prosthesis that approximates the curve of the upper lid margin and/or the curve of the lower lid margin.

The incremental thickness region (aperture widening zone) of the prosthesis can have a maximum delta thickness differential (added thickness) within the range of 25 microns to 1,000 microns, with a preferred range of 100 microns to 500 microns, with a more preferred range of 75 microns to 400 microns.

The regressive thickness region (aperture widening zone) of the prosthesis can have a maximum delta thickness differential (reduced thickness) within the range of 25 microns to 1,000 microns, with a preferred range of 100 microns to 500 microns, with a more preferred range of 100 microns to 400 microns, with a more preferred range of 75 microns to 400 microns.

The convex surface region of incremental thickness (aperture widening zone) of the prosthesis can be located within the range of 3 mm to 8.5 mm from the geometrical center of the contact lens, and more preferably within 5 mm to 7.75 mm from the geometrical center of the contact lens.

The region of incremental thickness or regressive thickness (aperture widening zone) is in most cases internal to the edge of the prosthesis. However in some cases, not most, it can start at the outer edge of the prosthesis.

The delta of maximum incremental thickness in most cases is within 0.5 mm to 3.0 mm internal to the edge of the prosthesis.

The delta of maximum regressive thickness in most cases is within 0.5 mm to 3.0 mm internal to the edge of the prosthesis The incremental thickness region (zone, area) (aperture widening zone) is in most cases within 0.1 mm to 6.0 mm internal to the outer edge of the prosthesis.

The incremental thickness region (zone, area) (aperture widening zone) in some cases can start at the outer edge of the prosthesis and proceed to 6 mm internal to the outer edge of the prosthesis.

The regressive thickness region (zone, area) (aperture widening zone) is in most cases within 0.1 mm to 6.0 mm internal to the edge of the prosthesis. However in some cases, not most, it can start at the outer edge of the prosthesis.

The width of the incremental thickness region (zone, area) (aperture widening zone) or the regressive thickness region (zone, are) (aperture widening zone) can be 0.5 mm to 6 mm.

The incremental thickness diameter and the regressive thickness diameter falls within the range of 7 mm to 15 mm.

In some embodiments there are multiple rings or zones of incremental thickness and or regressive thickness; whereby one ring is located interior to another ring (or closer to the geometrical center of the lens).

In some embodiments, the region or zone of incremental thickness (aperture widening zone) has a slope and a delta of maximum thickness, whereby the outer slope on the outside of the delta of maximum incremental thickness (closer to the outer edge of the prosthesis) is steeper than the inner slope on the inside (closest to the center of the prosthesis).

In some embodiments, the region or zone of regressive thickness has an outer slope and a delta of maximum regressive thickness, whereby the inner slope on the side of the delta of maximum regressive thickness (closer to the center of the prosthesis) is the steepest.

In some embodiments, the region or zone of regressive thickness has an outer slope and a delta of maximum regressive thickness, whereby the inner slope on the side of the delta of maximum regressive thickness (closer to the center of the prosthesis) is equal to the outer slope.

In some embodiments, the prosthesis in the form of a contact lens or scleral ring can comprise finger like members that fold towards the center of the scleral ring when the eye lid closes or blinks and opens away (unfolds) from the center of the scleral ring when the eye lid is opened. The finger like members can be located on the region of the scleral ring above and below the pupil of the eye. The finger like members can elevate the upper lid and depress or lower the lower lid when the eye lid is open and not blinking or closed.

When the term contact lens is provided or used in this disclosure it is meant to be that of one of a corneo-scleral contact lens or hybrid contact lens.

When the term incremental thickness region is used it is meant to be the aperture widening zone.

When the term regressive thickness region is used it is meant to be the aperture widening zone.

When the term increased surface friction region is used it is mean to be the aperture widening zone In some embodiments of the prosthesis there may or may not be an incremental thickness zone (region, area), or a regressive thickness zone (region, area) but rather the surface of the zone or region is altered to provide increased lid friction compared to other areas of the prosthesis. This region or zone of increased surface friction can be easily over come during an eye lid blink or forced closure but upon opening the eye lid this region of increased friction elevates the upper lid and/or depresses the lower lid thus opening the aperture of the eye.

The prosthesis disclosed herein can be stabilized (by the use of a stabilization zone) to prevent rotation in the case, by example only, of a multifocal or a toric single vision lens or a toric multifocal.

The prosthesis disclosed herein can be devoid of stabilization (not stabilized/free to rotate) in the case, by example only, of a single vision spherical lens.

The prosthesis disclosed herein can be free to rotate upon natural/normal blinking of the eyes always when in the form of a scleral ring. And also in most (but not all embodiments) when in the form of a single vision contact lens comprising solely spherical optical power and devoid of a stabilization zone, feature or member.

The prosthesis in some embodiments disclosed herein is not free to rotate upon natural/normal blinking of the eyes always when in the form of a scleral ring.

In some embodiments the aperture widening zone and the stabilization zone can be one and the same by design. In other embodiments the aperture widening zone is separate from the stabilization zone, feature or member.

Figure 49:
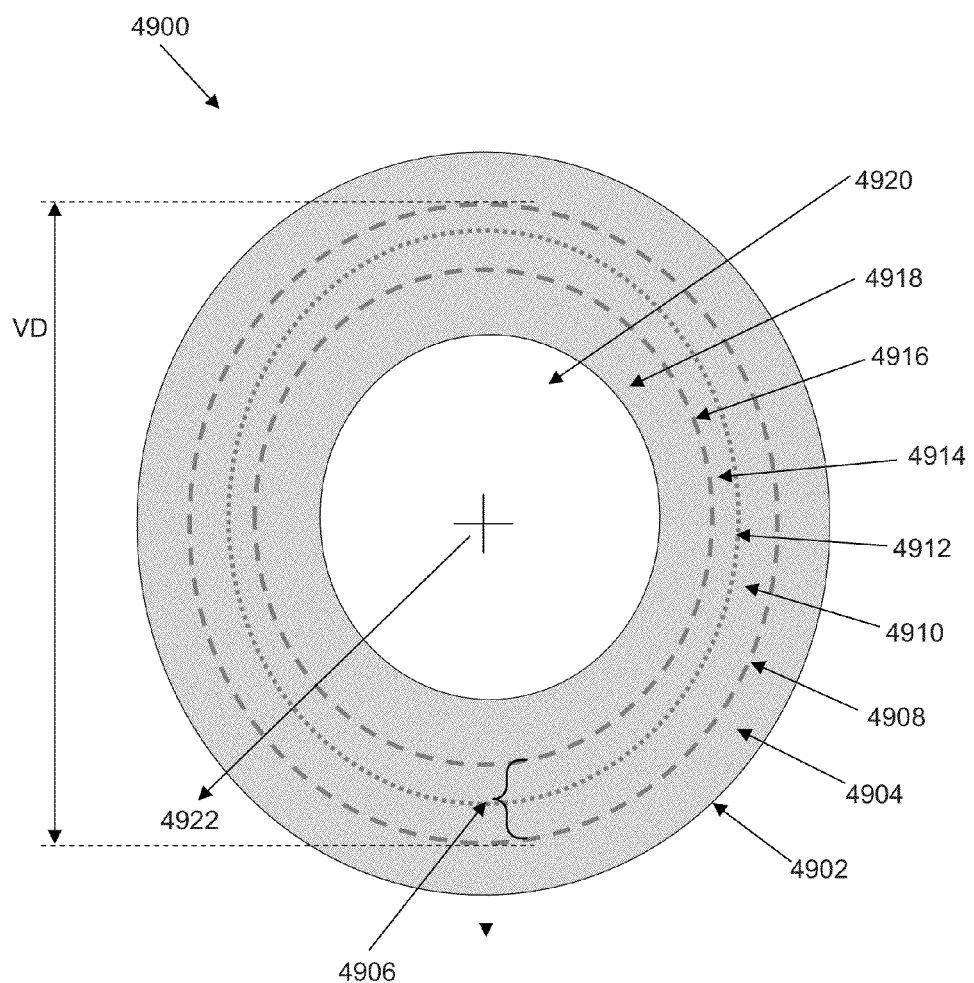
FIG. 49 shows a scleral ring with an aperture widening zone having an incremental thickness according to one embodiment.

FIGS. 49-53 illustrate exemplary embodiments of a prosthesis having an aperture widening zone. FIG. 49 shows a scleral ring 4900 having an aperture widening zone 4906 spaced apart from its peripheral edge 4902. Located between peripheral edge 4902 and aperture widening zone 4906 is a first region 4904. First region 4904 has a thickness and curvature equal to that of a conventional scleral ring. Aperture widening zone 4906 has an outer edge 4908 and an inner edge 4916. Aperture widening zone 4906 has an incremental thickness defined by an outer slope 4910 and an inner slope 4914 with a maximum incremental thickness 4912 located between outer slope 4910 and inner slope 4914. A second region 4918 is located adjacent to inner edge 4916 and extends towards an open central aperture 4920. Similar to first region 4904, second region 4918 has a thickness and curvature equal to that of a conventional scleral ring. Located in the center of open central aperture 4920 is the geometric center 4922 of scleral ring 4900. FIG. 49 also shows the vertical dimension (VD) of scleral ring 4900. The vertical dimension (VD) being measured from the upper most point of outer edge 4908 to the lower most point of outer edge 4908.

Figure 50:
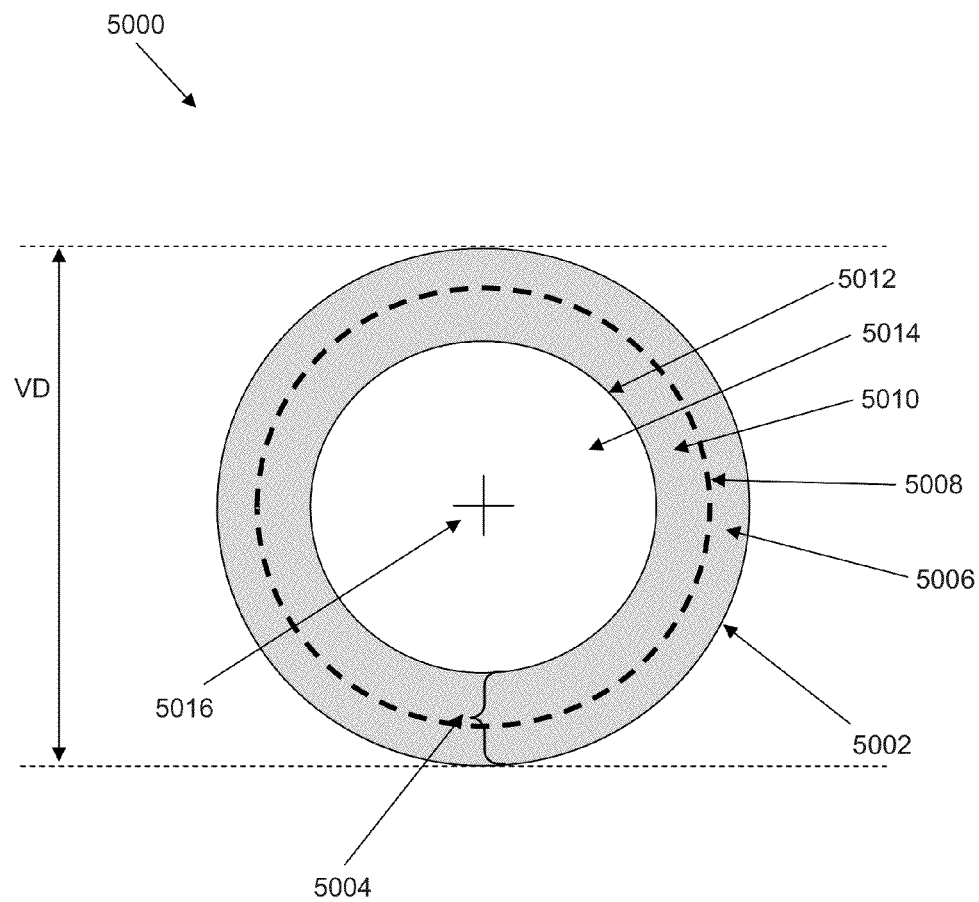
FIG. 50 shows a scleral ring with an aperture widening zone having an incremental thickness according to one embodiment.

FIG. 50 shows a scleral ring 5000 having an aperture widening zone 5004 beginning at its peripheral edge 5002. Aperture widening zone 5004 has an incremental thickness defined by an outer slope 5006 and an inner slope 5010 with a maximum incremental thickness 5008 located between outer slope 5006 and inner slope 5010. Aperture widening zone 5004 includes an inner edge 5012 adjacent to an open central aperture 5014. Located in the center of open central aperture 5014 is the geometric center 5016 of scleral ring 5000. FIG. 50 also shows the vertical dimension (VD) of scleral ring 5000. The vertical dimension (VD) being measured from the upper most part of peripheral edge 5002 to the lower most part of peripheral edge 5002.

Figure 51:
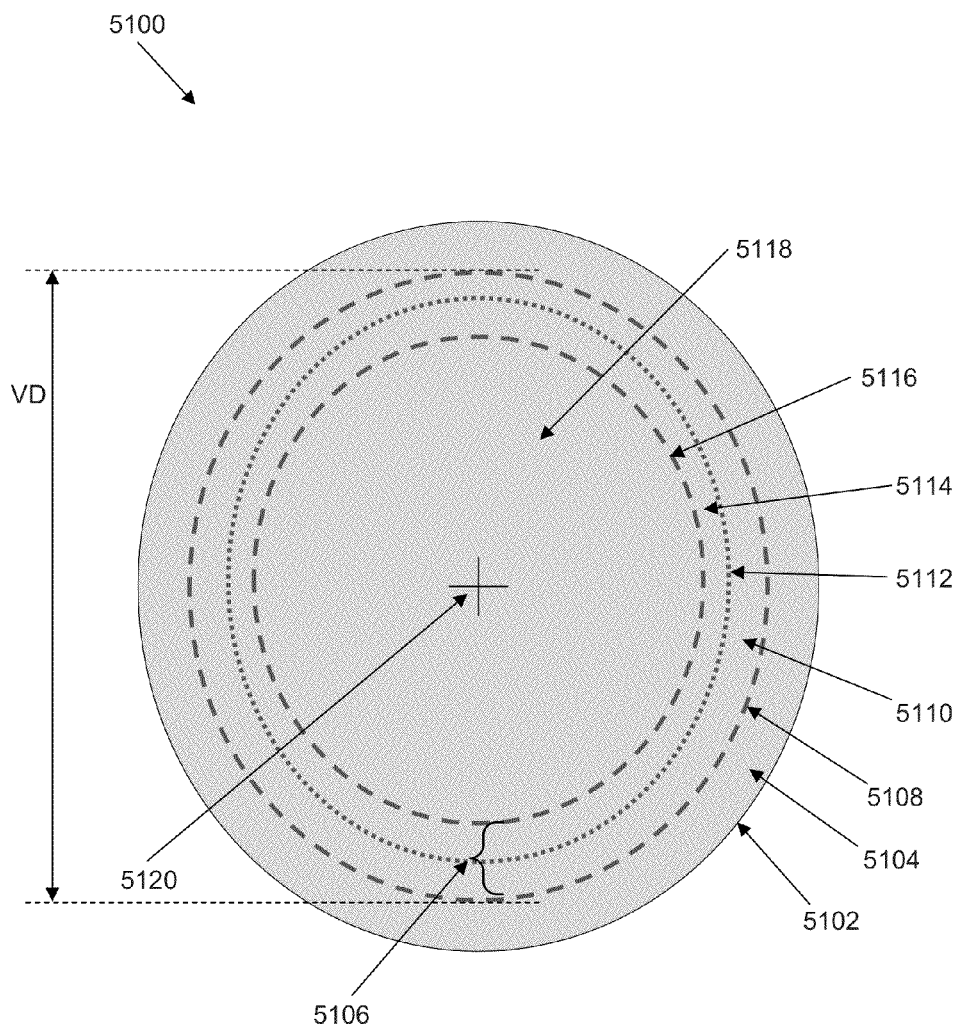
FIG. 51 shows a contact lens with an aperture widening zone having an incremental thickness according to one embodiment.

FIG. 51 shows a contact lens 5100 having an aperture widening zone 5106 spaced apart from its peripheral edge 5102. Located between peripheral edge 5102 and aperture widening zone 5106 is a first region 5104. First region 5104 has a thickness and curvature equal to that of a conventional contact lens. Aperture widening zone 5106 has an outer edge 5108 and an inner edge 5116. Aperture widening zone 5106 has an incremental thickness defined by an outer slope 5110 and an inner slope 5114 with a maximum incremental thickness 5112 located between outer slope 5110 and inner slope 5114. A second region 5118 is located adjacent to inner edge 5116 and extends towards the geometrical center 5120 of the contact lens 5100. Second region 5118 can have an optical power or can be devoid of optical power and has a thickness and curvature equal to that of a conventional contact lens having a specific optical power or lack thereof. FIG. 51 also shows the vertical dimension (VD) of contact lens 5100. The vertical dimension (VD) being measured from the upper most part of outer edge 5108 to the lower most part of outer edge 5108.

Figure 52:
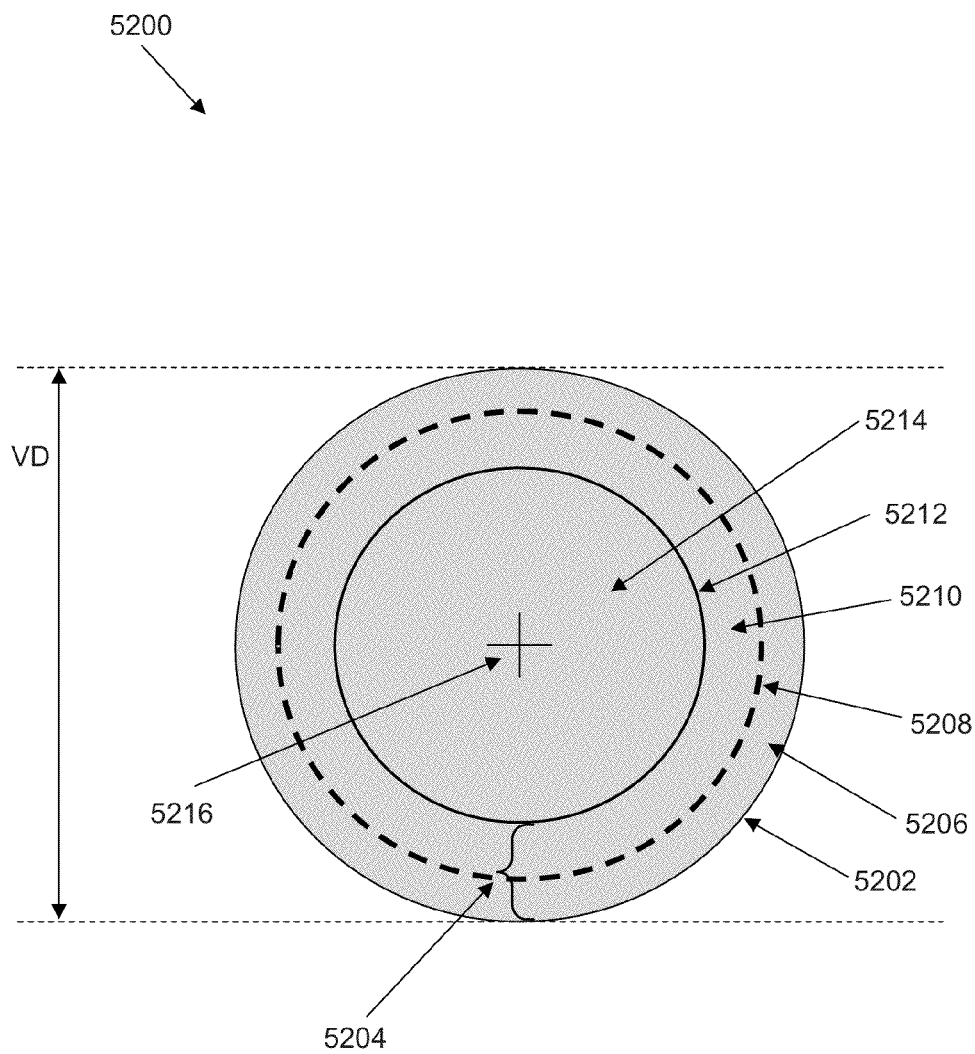
FIG. 52 shows a contact lens with an aperture widening zone having an incremental thickness according to one embodiment.
Figure 53C:
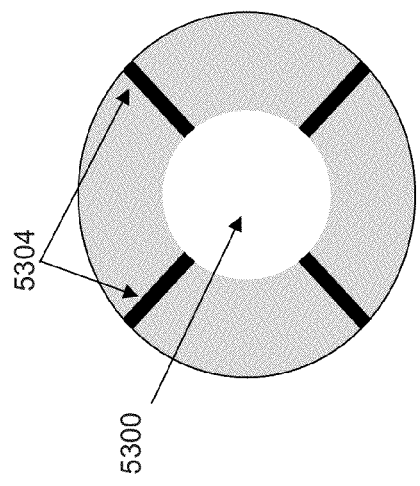
FIGS. 53A-C show various exemplary embodiments of scleral rings with aperture widening zones having a plurality of bands of incremental thickness.
Figure 53B:
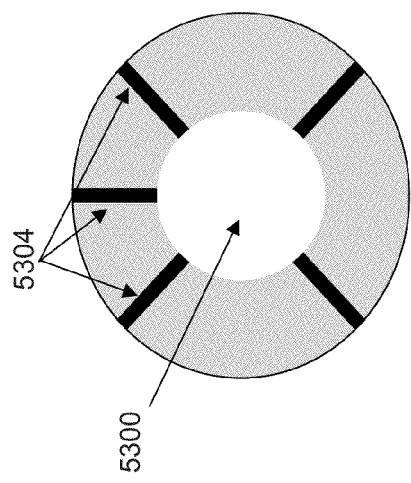
Figure 53A:
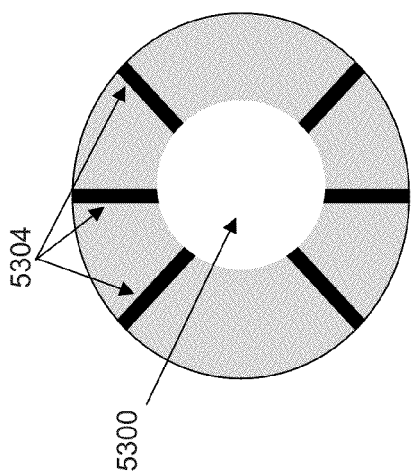
Figure 53E:
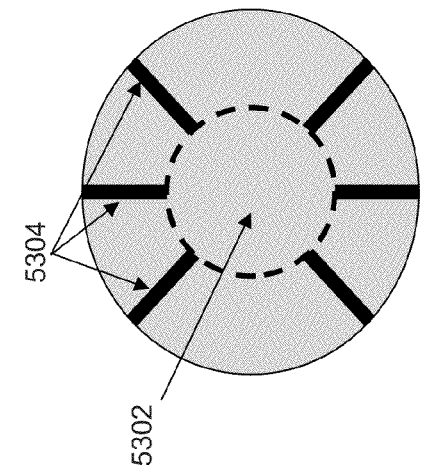
FIGS. 53D and 53E show various exemplary embodiments of contact lenses with aperture widening zones having a plurality of bands of incremental thickness
Figure 53D:
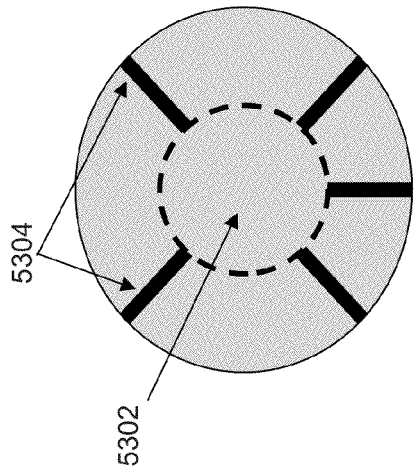

FIG. 52 shows a contact lens 5200 having an aperture widening zone 5204 beginning at its peripheral edge 5202. Aperture widening zone 5204 has an incremental thickness defined by an outer slope 5206 and an inner slope 5210 with a maximum incremental thickness 5208 located between outer slope 5206 and inner slope 5210. A second region 5214 is located adjacent to an inner edge 5212 of aperture widening zone 5204 and extends towards the geometric center 5216 of the contact lens 5200. Second region 5214 can have an optical power or can be devoid of optical power and has a thickness and curvature equal to that of a conventional contact lens having a specific optical power or lack thereof. FIG. 52 also shows the vertical dimension (VD) of contact lens 5200. The vertical dimension (VD) being measured from the upper most part of peripheral edge 5202 to the lower most part of peripheral edge 5202.

FIGS. 53A-E show various exemplary embodiments of aperture widening zones having a plurality of bands of incremental thickness 5304. The bands of incremental thickness are arranged in a spoke-like fashion around either an open central aperture 5300 or an optic zone 5302. While a plurality of different patterns are shown in FIGS. 53A-E it is appreciated that any number or orientation of bands of incremental thickness 5304 can be present in the aperture widening zone.

Figure 54:
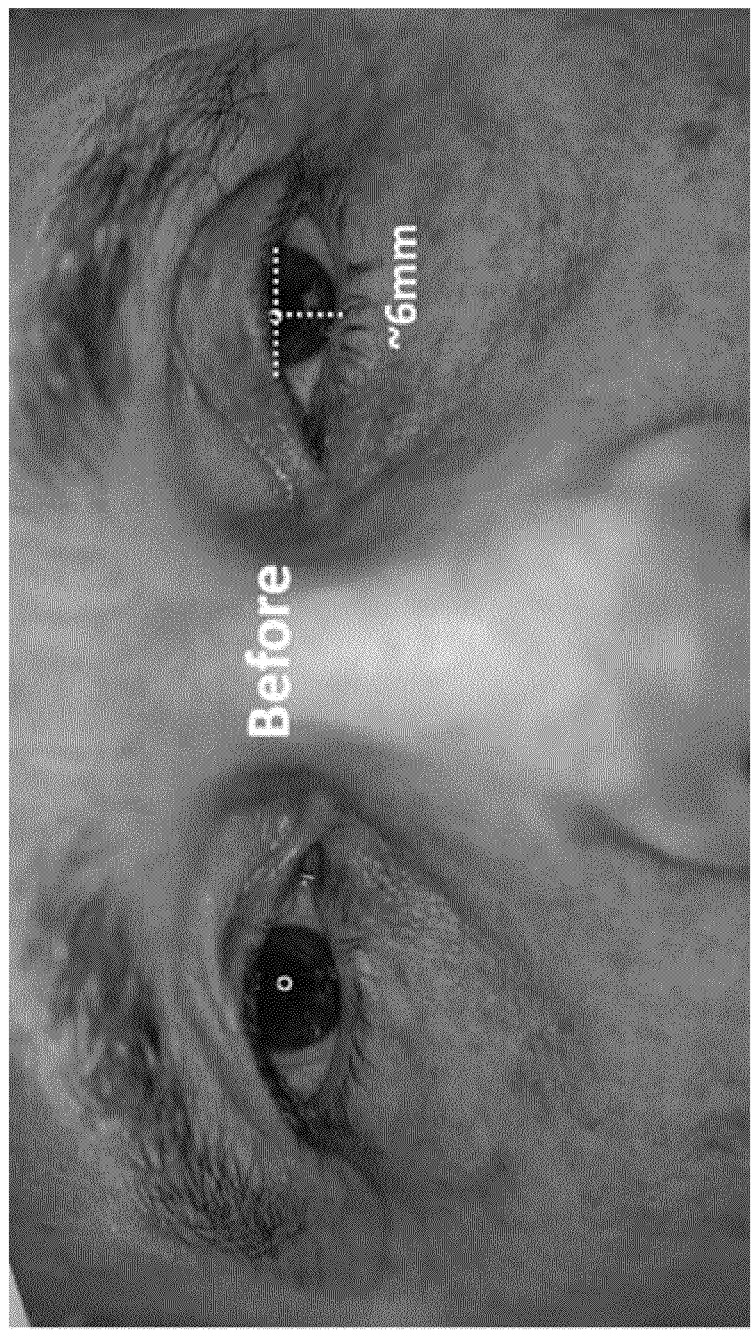
FIGS. 54-56 show a comparison of an individual's eyes with and without a prosthesis having an aperture widening zone.
Figure 55:
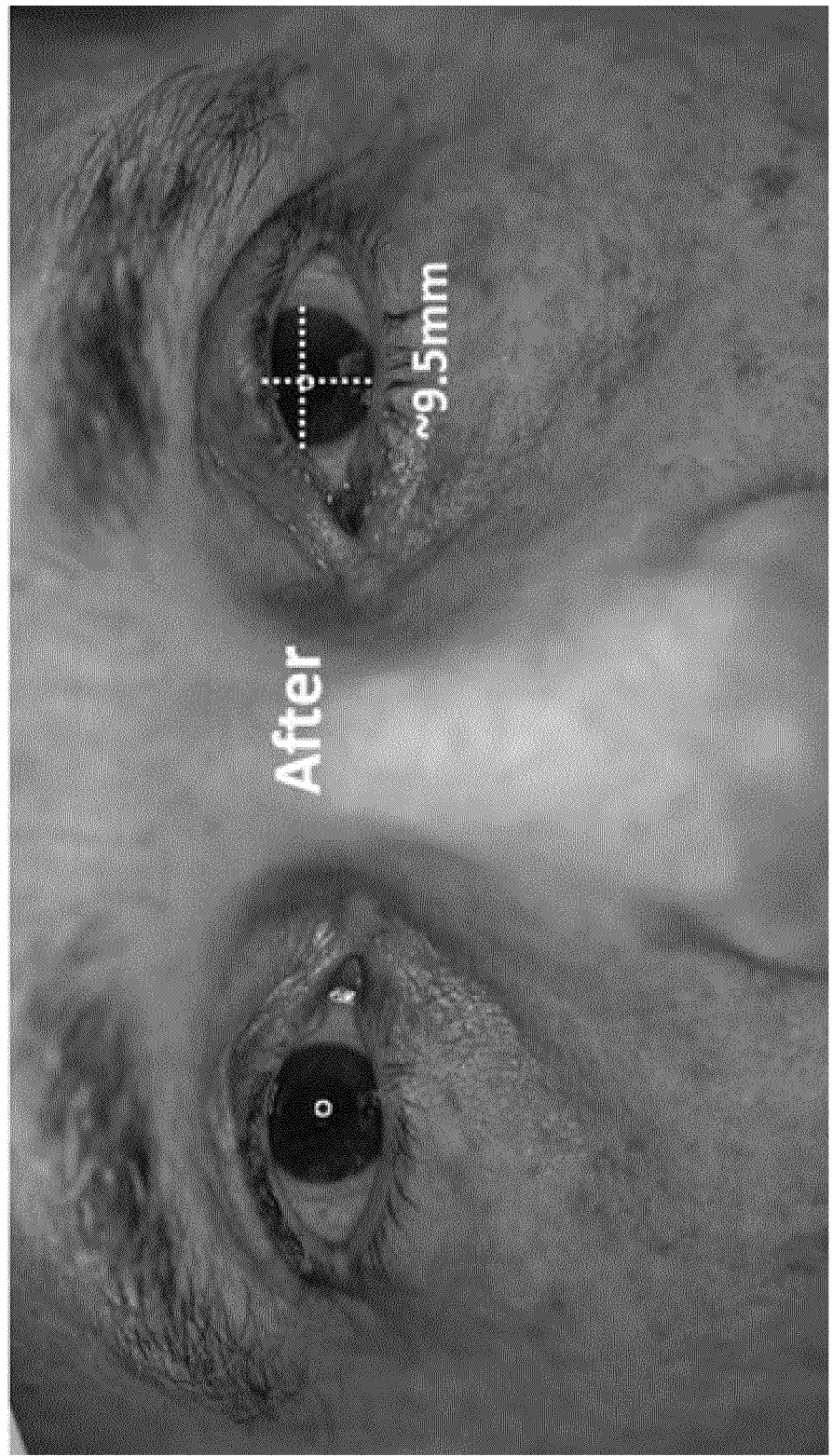
Figure 56:
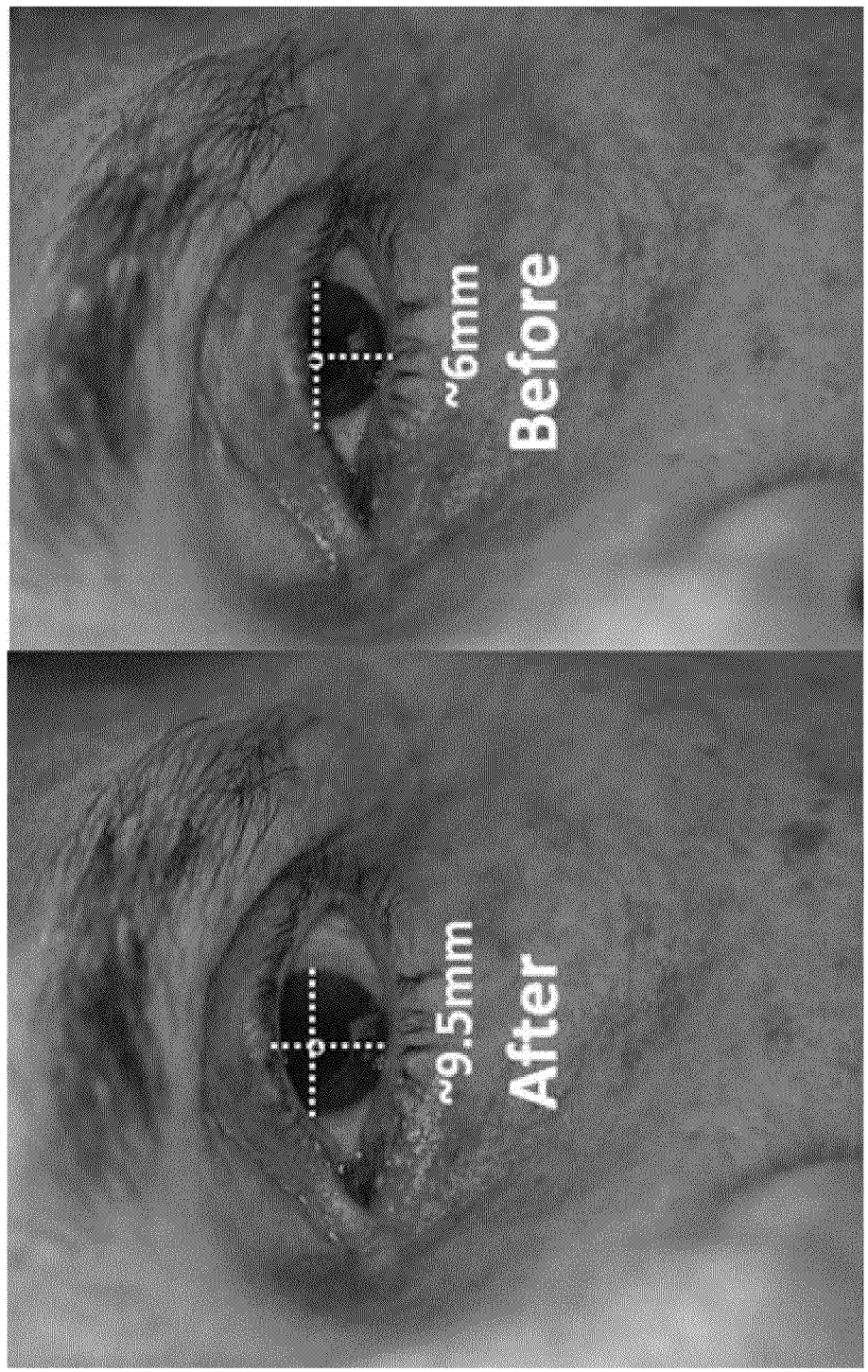
Figure 57:
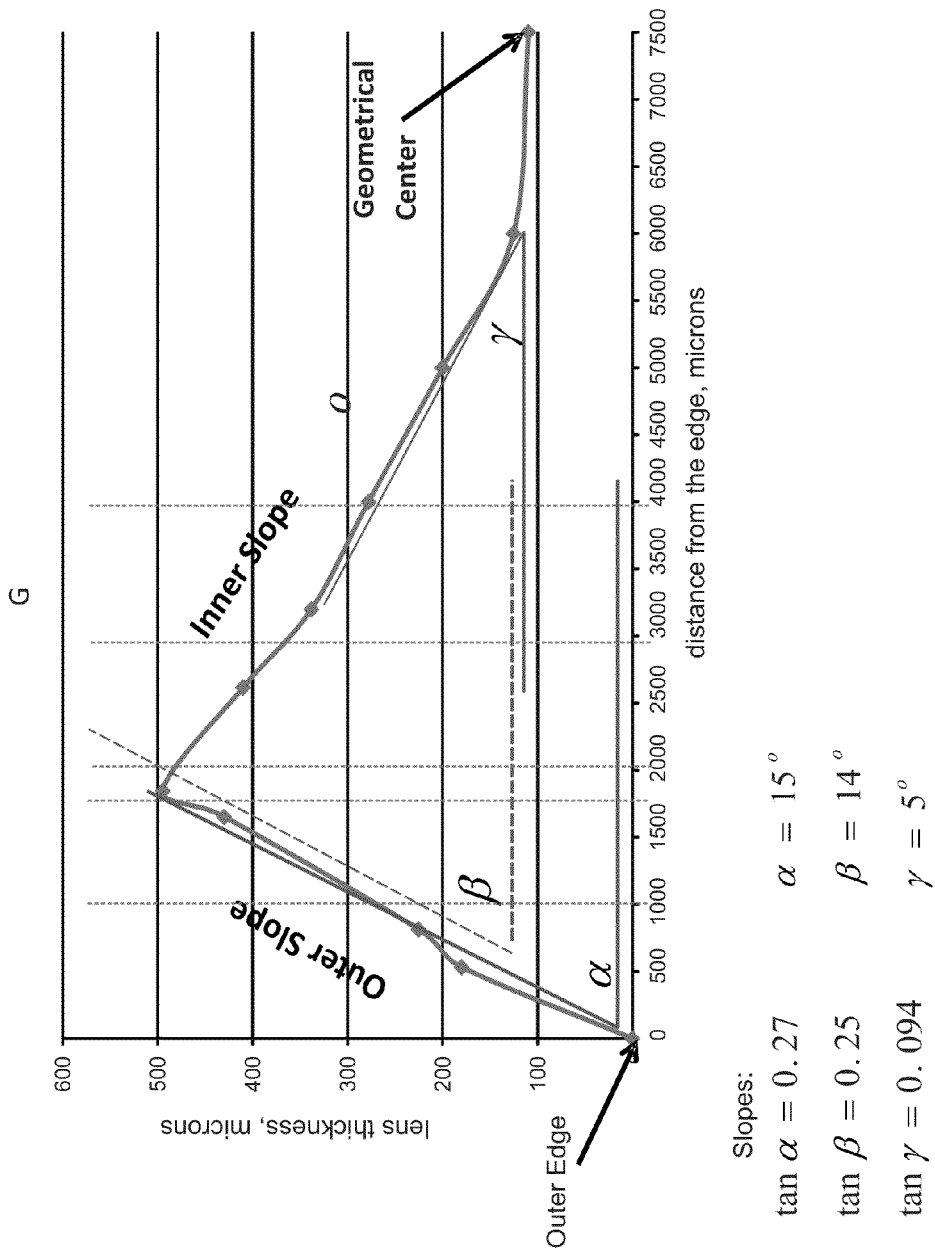
FIG. 57 is a graph illustrating the outer slope, inner slope and thickness of a prosthesis according to one embodiment.
Figure 58:
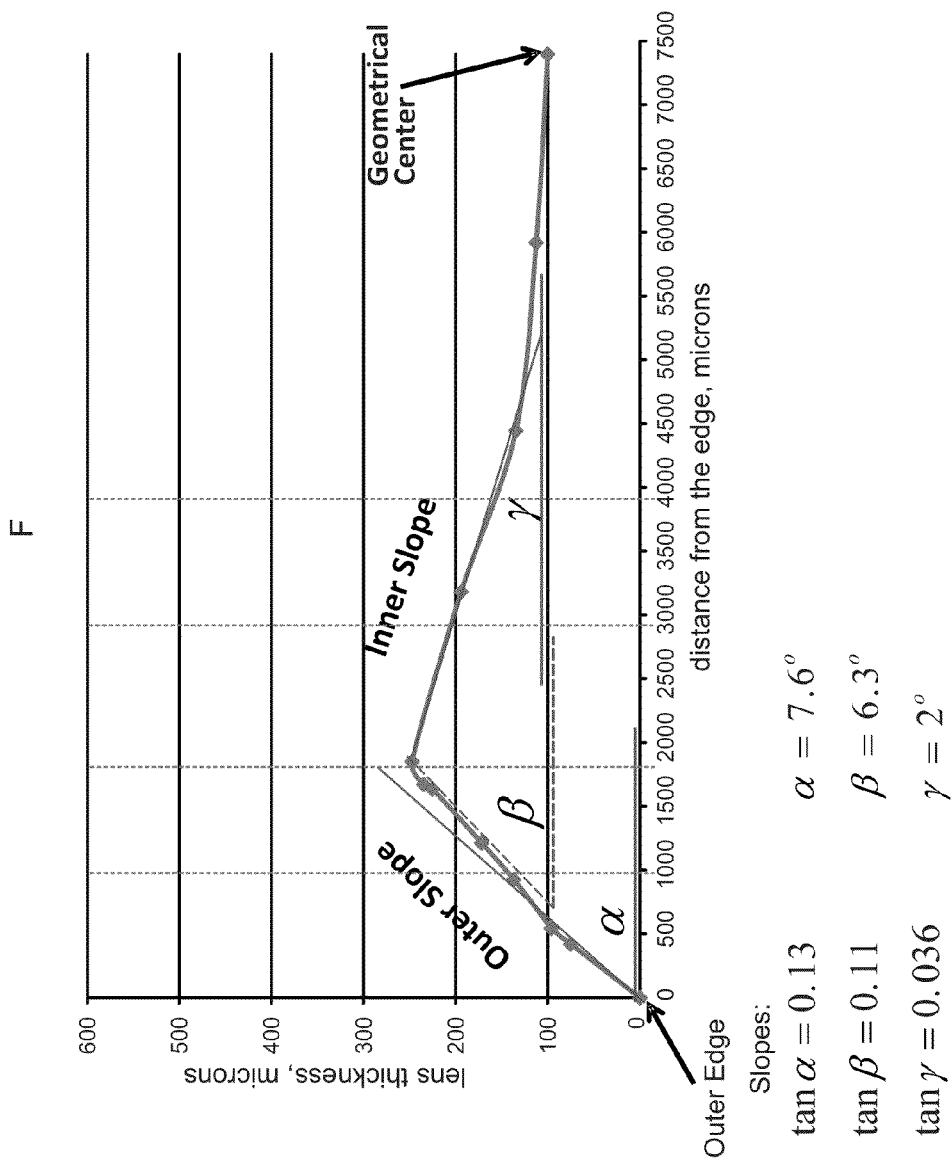
FIG. 58 is a graph illustrating the outer slope, inner slope and thickness of a prosthesis according to one embodiment.
Figure 59:
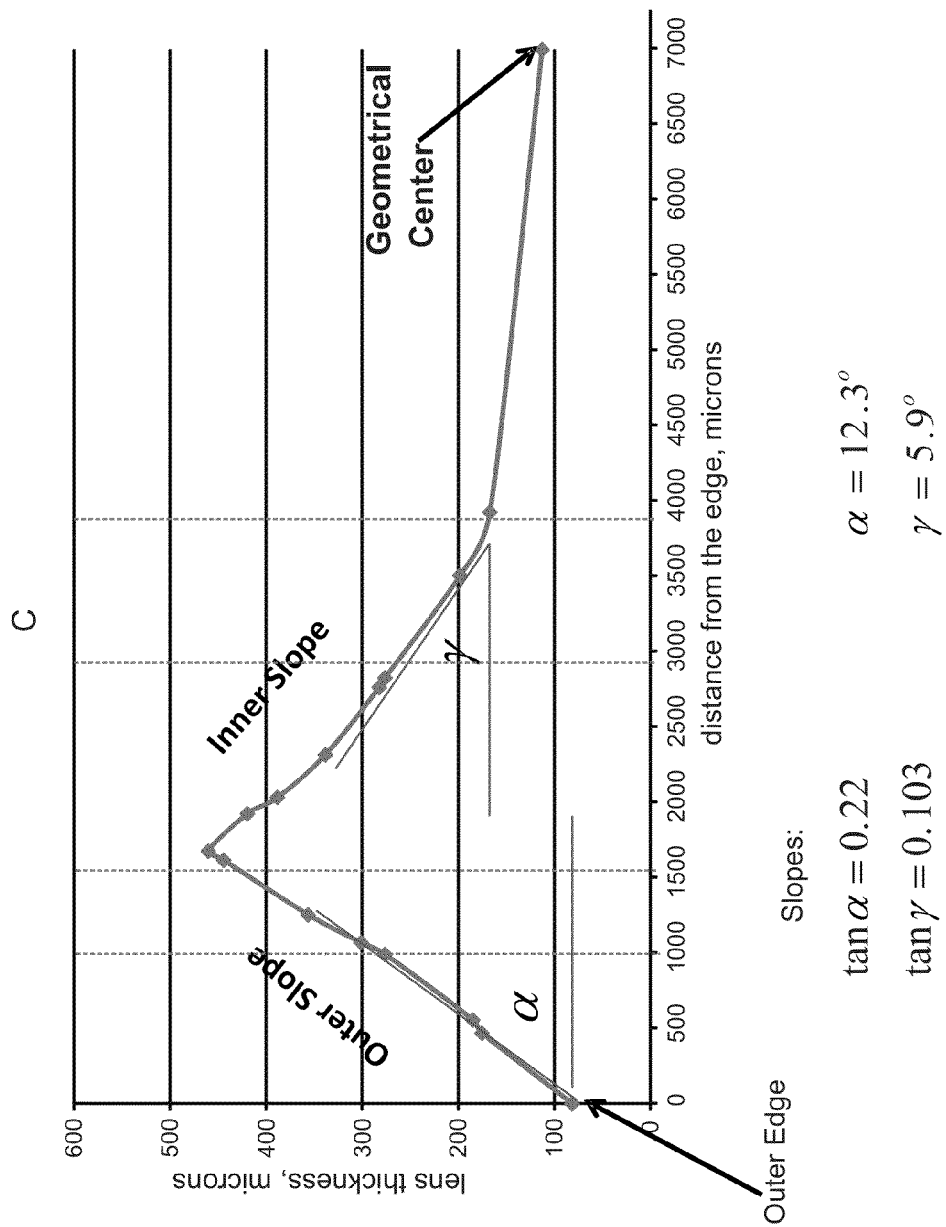
FIG. 59 is a graph illustrating the outer slope, inner slope and thickness of a prosthesis according to one embodiment.
Figure 60:
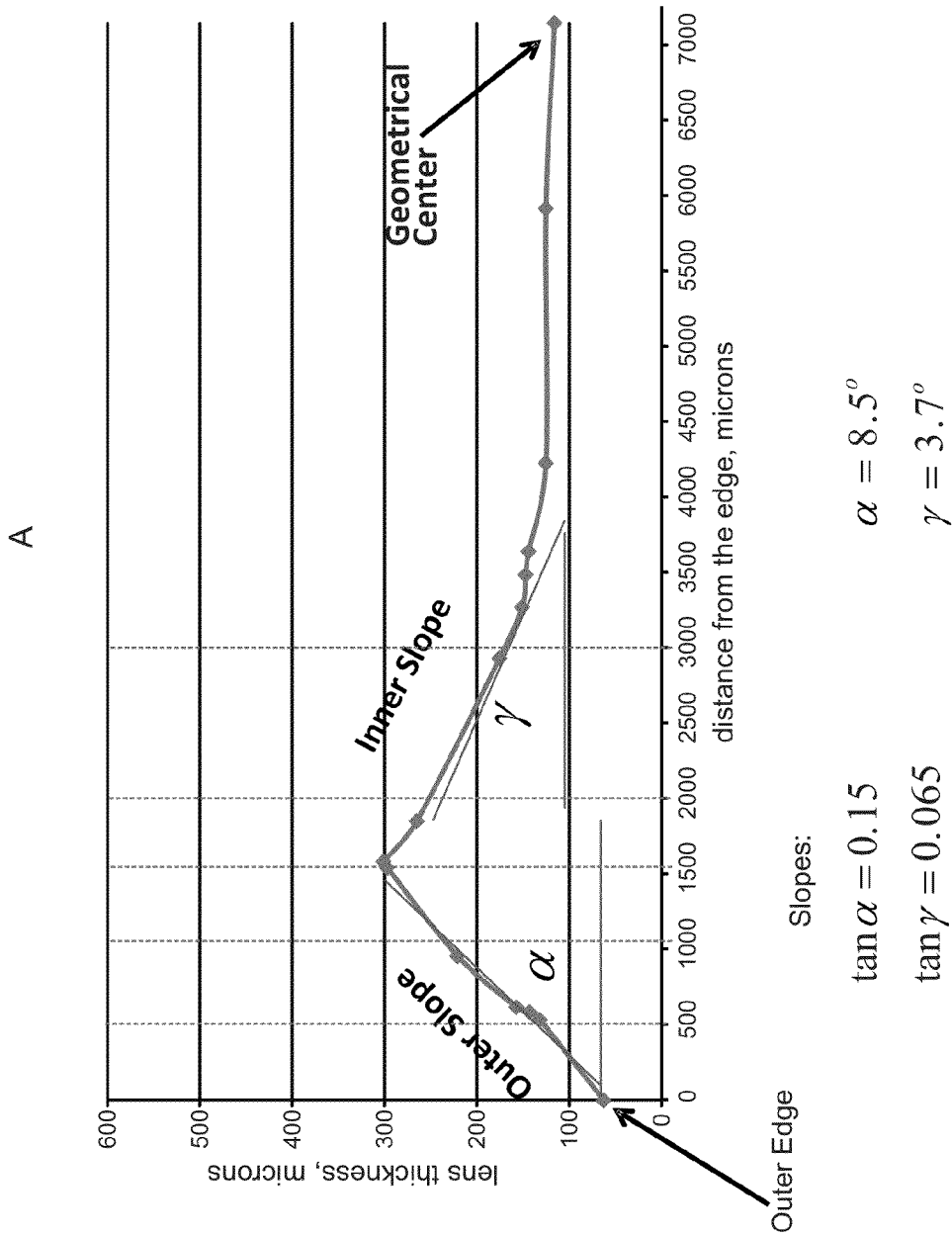
FIG. 60 is a graph illustrating the outer slope, inner slope and thickness of a prosthesis according to one embodiment.

FIGS. 54-56 illustrate the palpebral fissure widening effect of an aperture widening zone described herein. FIG. 54 shows an individual's natural palpebral fissure. As seen in FIG. 54 the maximum diameter of the individual's left natural palpebral fissure (right side of FIG. 54) is approximately 6 mm. FIG. 55 shows the same individual wearing a prosthesis having an aperture widening zone as described herein. It can be seen from FIG. 55 that the palpebral fissure of his left eye has been widened. The maximum diameter of his left eye's palpebral fissure is now approximately 9.5 mm, an increase of approximately 3.5 mm. FIG. 56 shows the left eye in FIGS. 54 and 55 side by side for comparison.

FIGS. 57-60 show various graphs exemplifying the surface profile of embodiments of the prosthesis as described herein. FIGS. 57-60 quantify the inner and outer slopes of various aperture widening zones.

Figure 61:
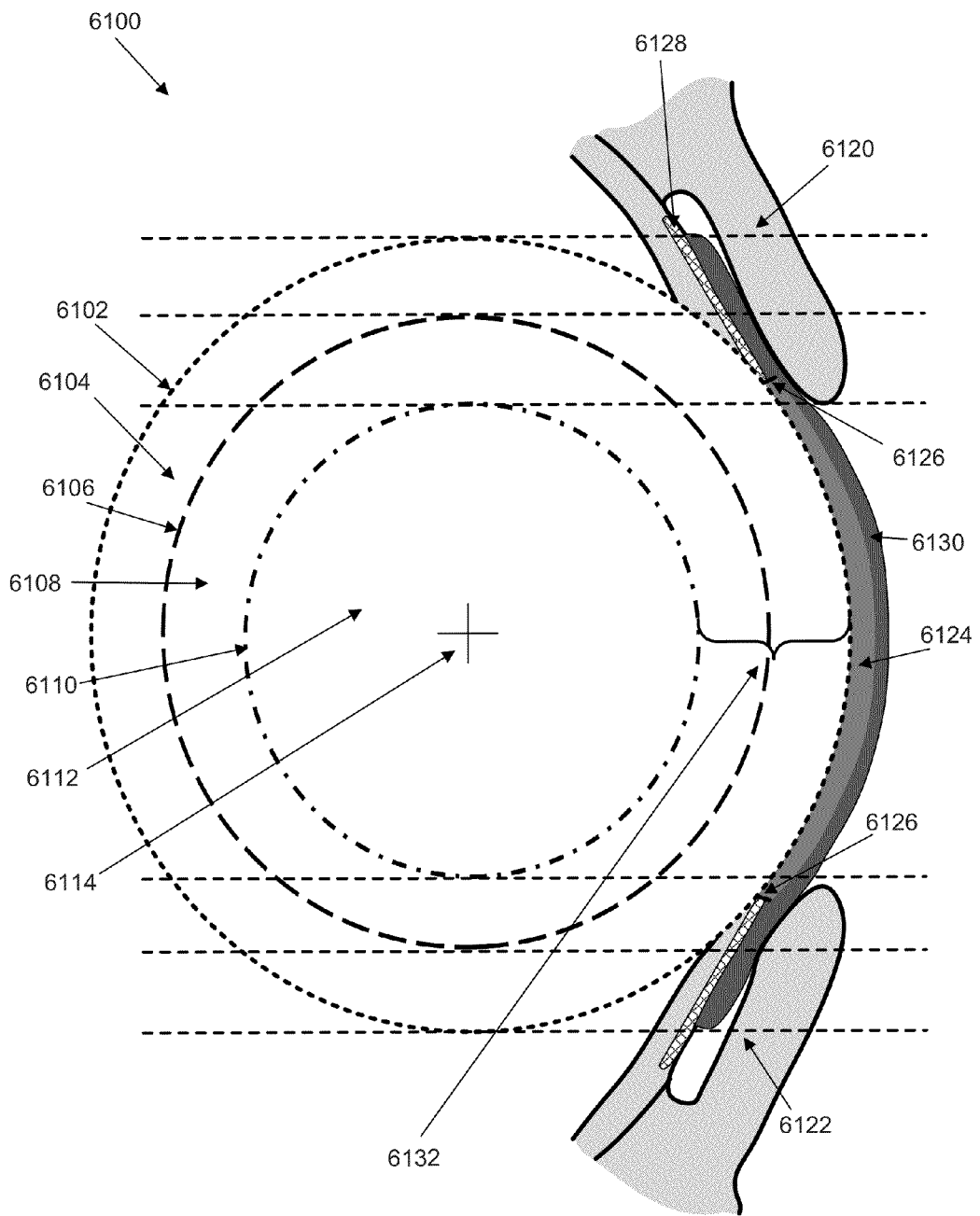
FIG. 61 illustrates the dimensions and fit to the eye of a corneo-scleral contact lens prosthesis according to one embodiment compared to the structure of an eye.

FIG. 61 illustrates the dimensions of a contact lens 6130 compared to the anatomy of a human eye. The human eye has an upper lid 6120, a lower lid 6122, a cornea 6124, and a sclera 6128. Located at the interface of cornea 6214 and sclera 6128 is a limbus 6126. Contact lens 6130 having an aperture widening zone 6132 is shown as being worn on the eye and extends across cornea 6124 and limbus 6126 to sclera 6128 on both sides of cornea 6124. A visual representation 6100 of contact lens 6130 is shown to the left of the eye (this is not the actual lens, but rather a representation showing the various dimensions of contact lens 6130). As shown by visual representation 6100, contact lens 6130 has an aperture widening zone 6132 located adjacent to a peripheral edge 6102. Aperture widening zone 6132 is defined by an outer slope 6104, a maximum incremental thickness 6106, an inner slope 6108, and an inner edge 6110. Located inside of inner edge 6110 is an optical power zone 6112 with a geometric center 6114 located therein. It can be seen from FIG. 61 that maximum incremental thickness 6106 is located outside of limbus 6126 on both sides of the eye.

Figure 62:
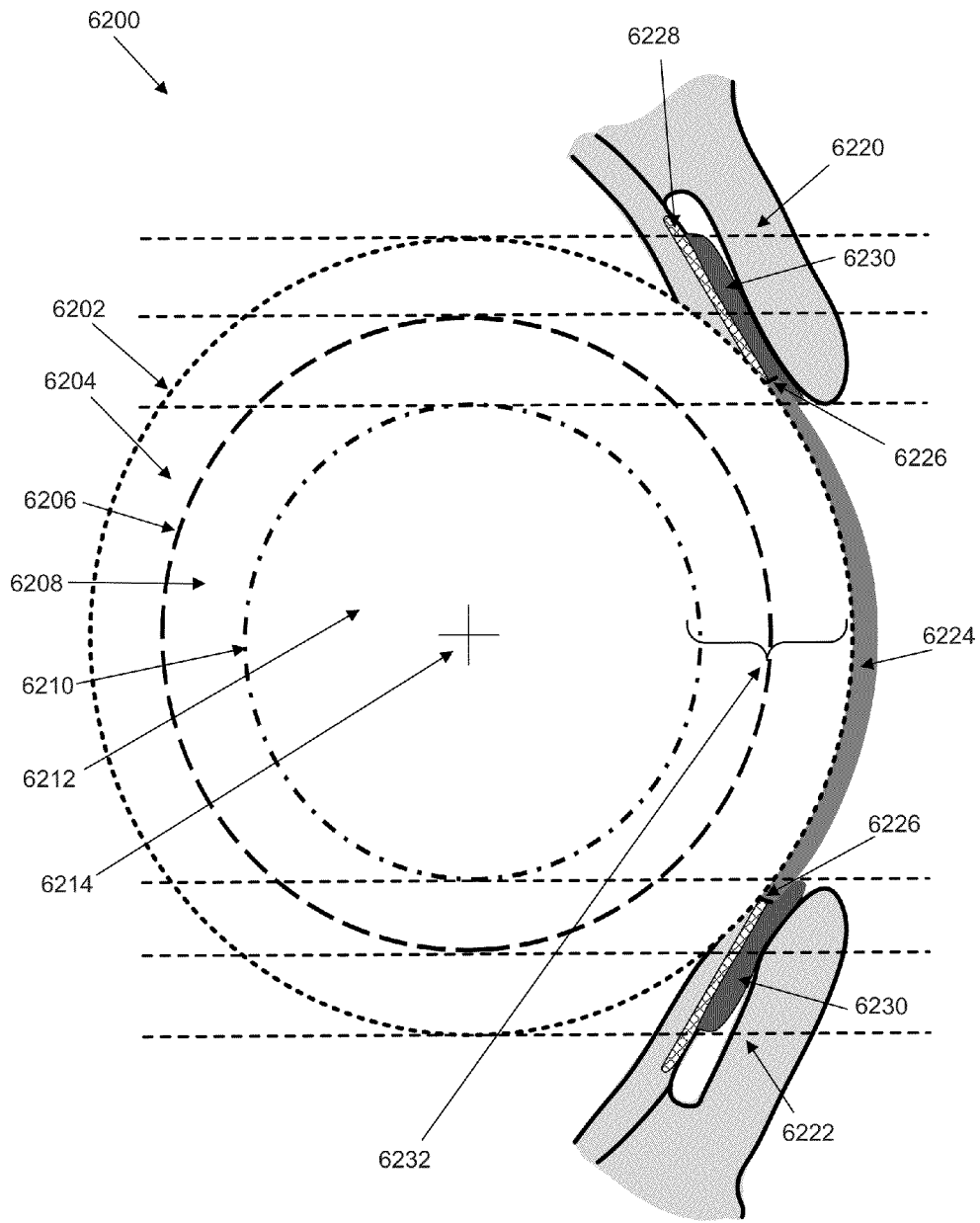
FIG. 62 illustrates the dimensions and fit to the eye of a scleral ring prosthesis according to one embodiment compared to the structure of an eye.

FIG. 62 illustrates the dimensions of a scleral ring 6230 compared to the anatomy of a human eye. The human eye has an upper lid 6220, a lower lid 6222, a cornea 6224, and a sclera 6228. Located at the interface of cornea 6214 and sclera 6228 is a limbus 6226. Scleral ring 6230 having an aperture widening zone 6232 is shown as being worn on the eye and extends across cornea 6224 and limbus 6226 to sclera 6228 on both sides of cornea 6224. A visual representation 6200 of scleral ring 6230 is shown to the left of the eye (this is not the actual lens, but rather a representation showing the various dimensions of scleral ring 6130). As shown by visual representation 6200, scleral ring 6230 has an aperture widening zone 6232 located adjacent to a peripheral edge 6202. Aperture widening zone 6232 is defined by an outer slope 6204, a maximum incremental thickness 6206, an inner slope 6208, and an inner edge 6210. Located inside of inner edge 6210 is an open central aperture 6212 with a geometric center 6214 located therein. It can be seen from FIG. 62 that maximum incremental thickness 6206 is located outside of limbus 6226 on both sides of the eye.

FIGS. 63A-66D illustrate examples of how to measure the vertical dimension and/or the minimum vertical dimension for various shapes. While these figures are simplified versions of exemplary shapes of aperture widening zones it is appreciated that any shape will have a vertical dimension and a minimum vertical dimension. For purposes of these illustrations it will be assumed that the points used to measure vertical dimensions and/or minimum vertical dimensions would be located on the upper most part of an aperture widening zone and the lower most part of an aperture widening zone.

Figure 63B:
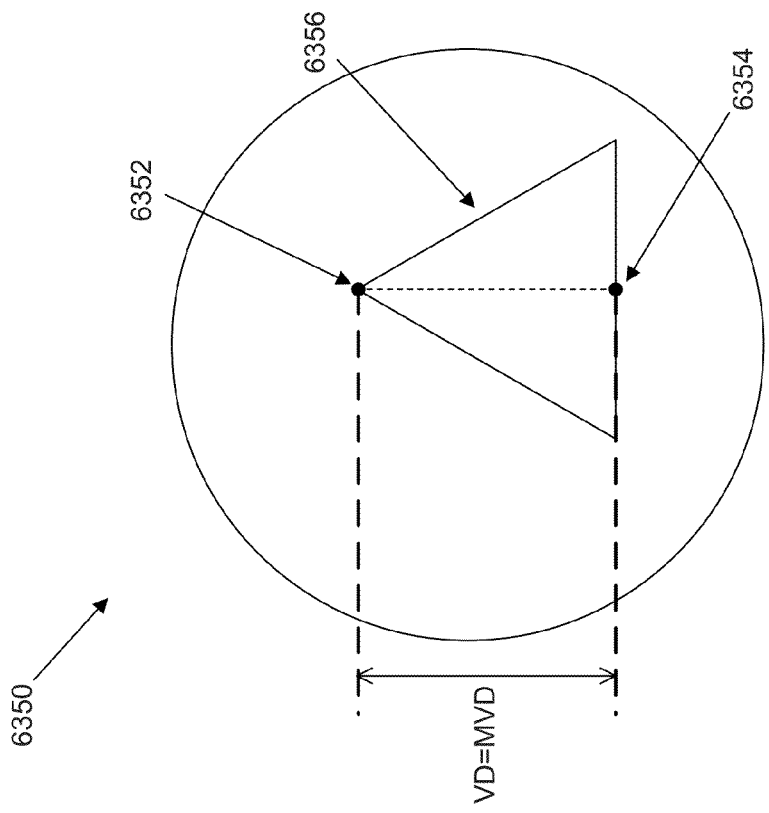
Figure 63A:
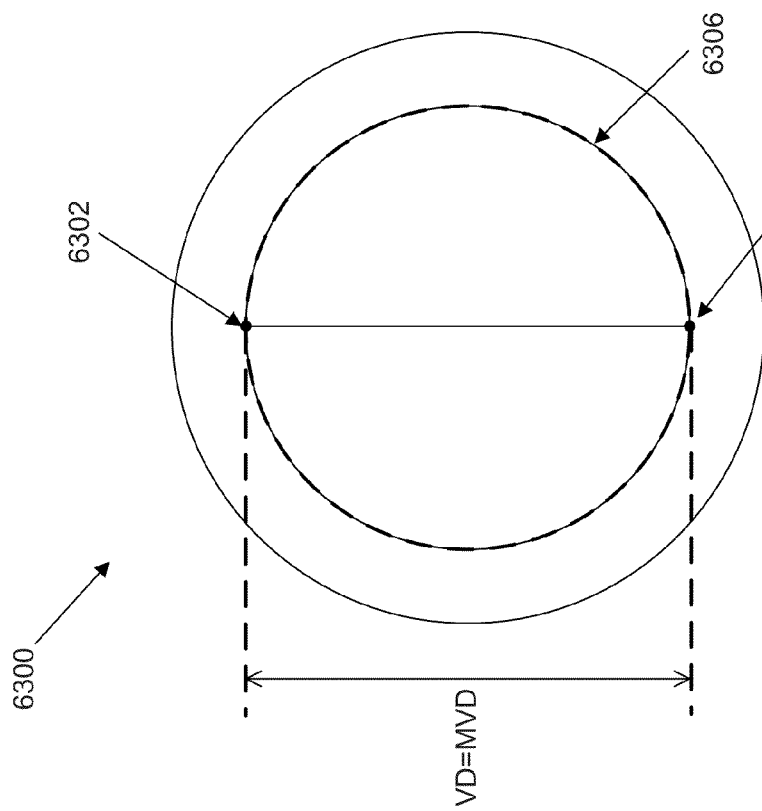
FIG. 63A illustrates how to measure the vertical dimension of an aperture widening zone on a prosthesis with an outer edge in the shape of a circle.

FIG. 63A shows a prosthesis 6300 having an aperture widening zone with an outer edge 6306 in the shape of a circle. The upper most point of outer edge 6306 is shown at point 6302 and the lower most point of outer edge 6306 is shown at point 6304. The vertical dimension (VD), measured from upper most point 6302 to lower most point 6304 and projected onto a vertical axis, is shown on the left side of FIG. 63A. Because outer edge 6306 is in the shape of a circle the vertical dimension (VD) is equal to the minimum vertical dimension (MVD). For a circle, this is true for any rotational orientation of the prosthesis.

FIG. 63B shows a prosthesis 6350 having an aperture widening zone with an outer edge 6356 in the shape of an equilateral triangle. The upper most point of outer edge 6356 is shown at point 6352 and the lower most point of outer edge 6356 is shown at point 6354. The vertical dimension (VD), measured from upper most point 6352 to lower most point 6354 and projected onto a vertical axis, is shown on the left side of FIG. 63B. In FIG. 63B this is the height of the equilateral triangle which is also the minimum vertical dimension (MVD). Because outer edge 6356 is in the shape of an equilateral triangle the vertical dimension will change based on the orientation of the lens. For example, as shown in FIG. 63C, if the triangle were turned on its side the upper most point would be point 6358 and the lower most point would be point 6360. The vertical dimension (VD), measured from point 6358 to point 6360 and projected onto a vertical axis, is shown on the left side of FIG. 63C. This rotational orientation of the triangle results in a larger vertical dimension. This larger vertical dimension results from the fact that all equilateral triangles have a height that is less than the length of their sides.

FIGS. 64A-C illustrate how to measure a vertical dimension (VD) and the minimum vertical dimension (MVD) of an aperture widening zone located on a prosthesis 6400 having an outer edge 6420 in the shape of an oval. FIG. 64A shows prosthesis 6400 in a first rotational orientation where the oval is positioned such that its minor axis is oriented in the vertical direction. The orientation in FIG. 64A shows a vertical dimension equal to minimum vertical dimension (MVD) for the oval. The minimum vertical dimension (MVD) is measured from upper most point 6402 to lower most point 6404 and projected onto a vertical axis. FIGS. 64B and C show other orientations of the oval where its vertical dimension (VD) is not its minimum vertical dimension. For example, in FIG. 64B the oval's major axis is oriented in the vertical direction. This results in a vertical dimension (VD), measured from point 6410 to point 6412, that is larger than the oval's minimum vertical dimension (MVD) shown in FIG. 64A. Similarly, the orientation of the oval in FIG. 64C shows a vertical dimension (VD), measured from point 6406 to point 6408, that is greater than the minimum vertical dimension (MVD) shown in FIG. 64A.

Figure 65B:
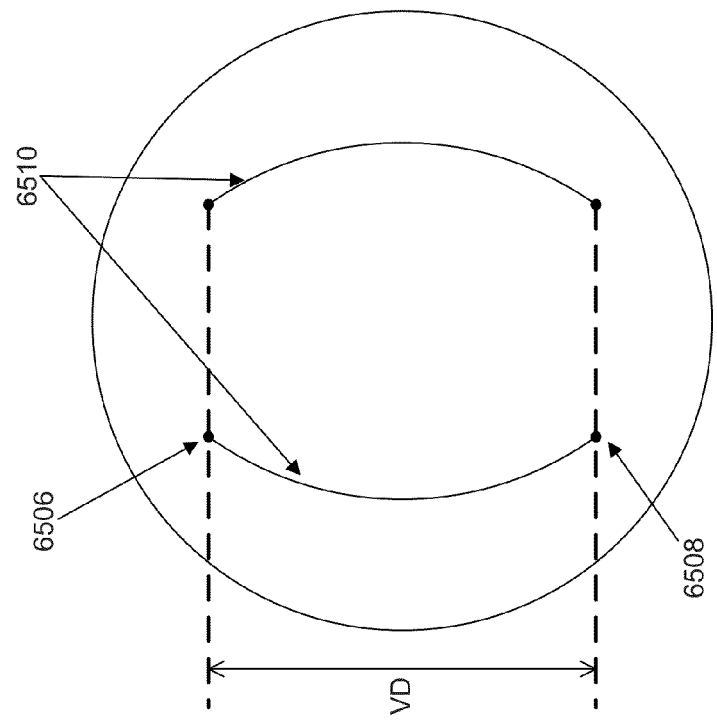
FIGS. 65A and 65B illustrate how to measure the minimum vertical dimension of an aperture widening zone on a prosthesis with outer edges in the shape two partial rings.
Figure 65A:
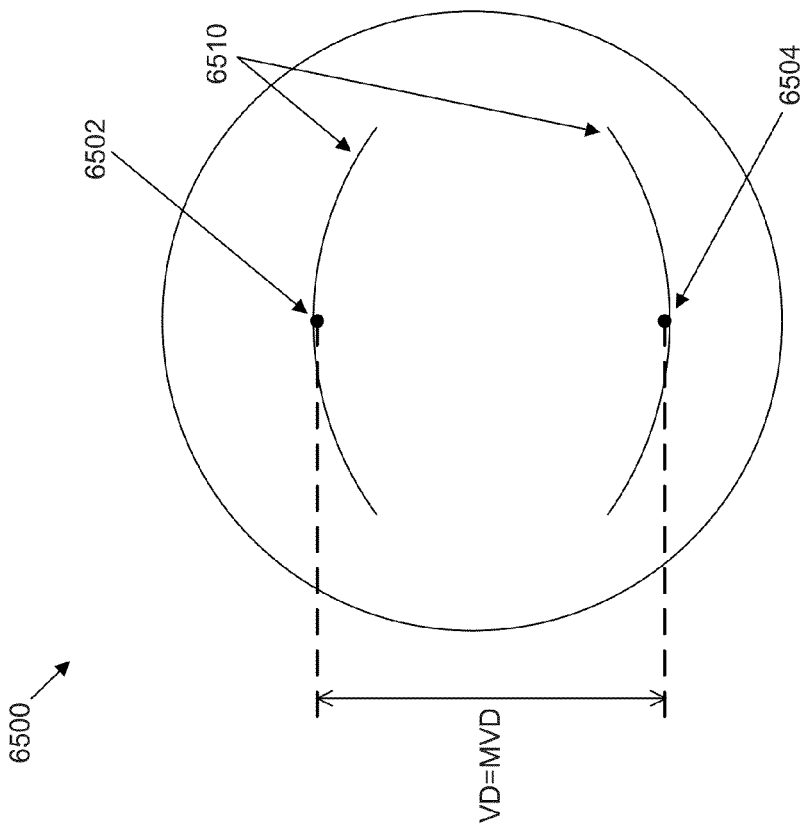

FIGS. 65A-B show another example of how to measure a vertical dimension (VD) and the minimum vertical dimension (MVD) of an aperture widening zone on a prosthesis 6500 defined by two partial rings having outer edges 6510. FIG. 65A shows an orientation of the prosthesis where the vertical dimension (VD) is equal to the minimum vertical dimension (MVD) for the aperture widening zone. The minimum vertical dimension (MVD) being measured from upper most point 6502 to lower most point 6504. FIG. 65B shows an orientation of prosthesis 6500 where the vertical dimension (VD) is not the minimum vertical dimension (MVD). The vertical dimension (VD) in FIG. 65B is measured from upper most point 6506 to lower most point 6508 and is larger than the minimum vertical dimension shown in FIG. 65A.

Figure 66B:
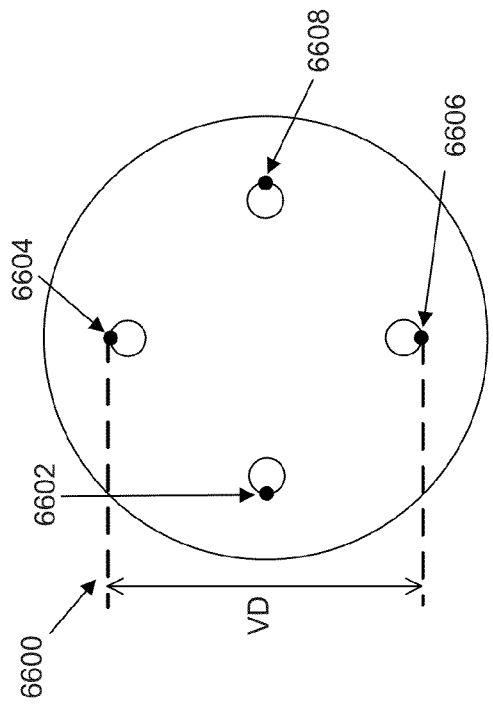
FIGS. 66A-D illustrate how to measure the minimum vertical dimension of an aperture widening zone on a prosthesis having a plurality of isolated areas.
Figure 66A:
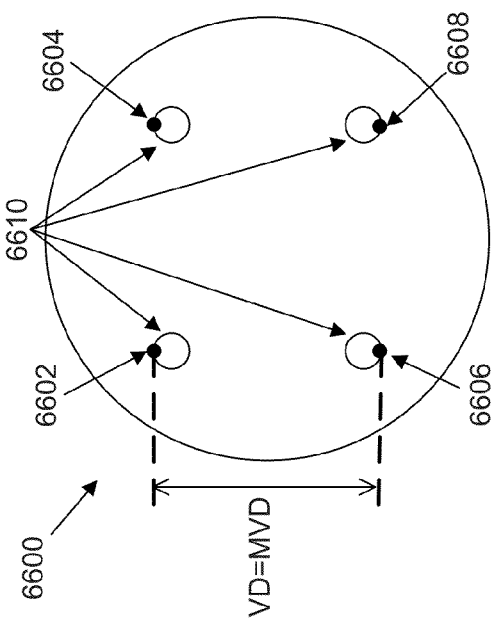

FIGS. 66A-B illustrate how to measure a vertical dimension and the minimum vertical dimension of an aperture widening zone on a prosthesis 6600 defined by a plurality of isolated areas with outer edges 6610 arranged in the shape of a square. FIG. 66A shows a first orientation of prosthesis 6600 where the vertical dimension (VD) for the aperture widening zone is equal to the minimum vertical dimension (MVD). Outer edges 6610 have points 6602, 6604, 6606, and 6608 which are located furthest from the center of prosthesis 6600. In FIG. 66A, the minimum vertical dimension (MVD) is measured from an upper most point 6602 to a lower most point 6606 and projected onto a vertical axis located on the left of FIG. 66A. FIG. 66B shows a second orientation of prosthesis 6600 illustrating a vertical dimension (VD) that is not the minimum vertical dimension (MVD). The vertical dimension (VD) in FIG. 66B is measured from upper most point 6604 to lower most point 6606 and projected onto a vertical axis shown on the left side of FIG. 66B. It can be seen that the vertical dimension (VD) in FIG. 66B is larger than the minimum vertical dimension (MVD) shown in FIG. 66A.

Figure 66D:
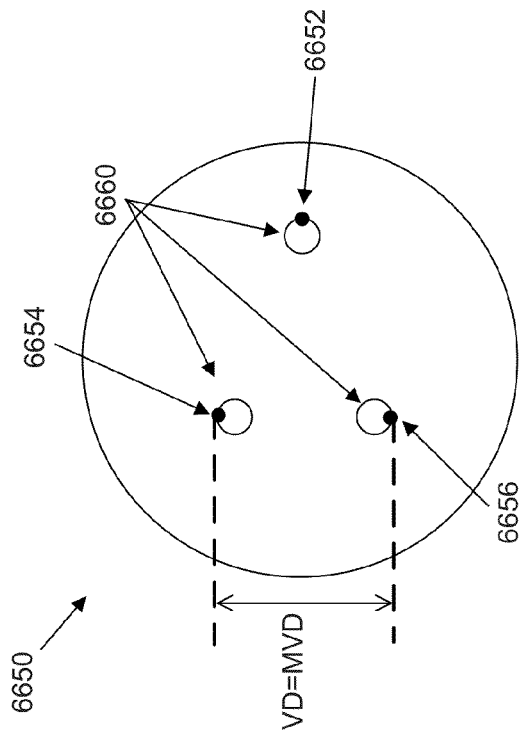
Figure 66C:
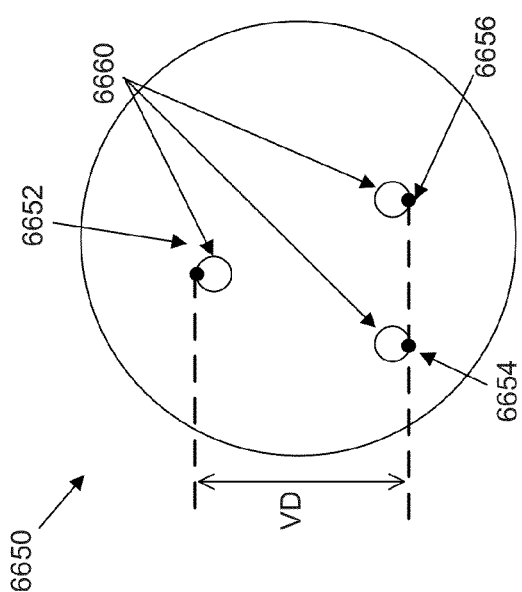

FIGS. 66C-D illustrate how to measure a vertical dimension and the minimum vertical dimension of an aperture widening zone on a prosthesis 6650 defined by a plurality of isolated areas with outer edges 6660 arranged in the shape of a triangle. FIG. 66C shows a first orientation of prosthesis 6650 wherein the vertical dimension (VD) is the distance between upper most point 6652 and lower most point 6654. FIG. 66D shows a second orientation wherein the vertical dimension is equal to the minimum vertical dimension (MVD). As shown in FIG. 66D the minimum vertical dimension (MVD), measured from upper most point 6654 to lower most point 6656, is projected onto a vertical axis to the left of FIG. 66D.

Figure 67:
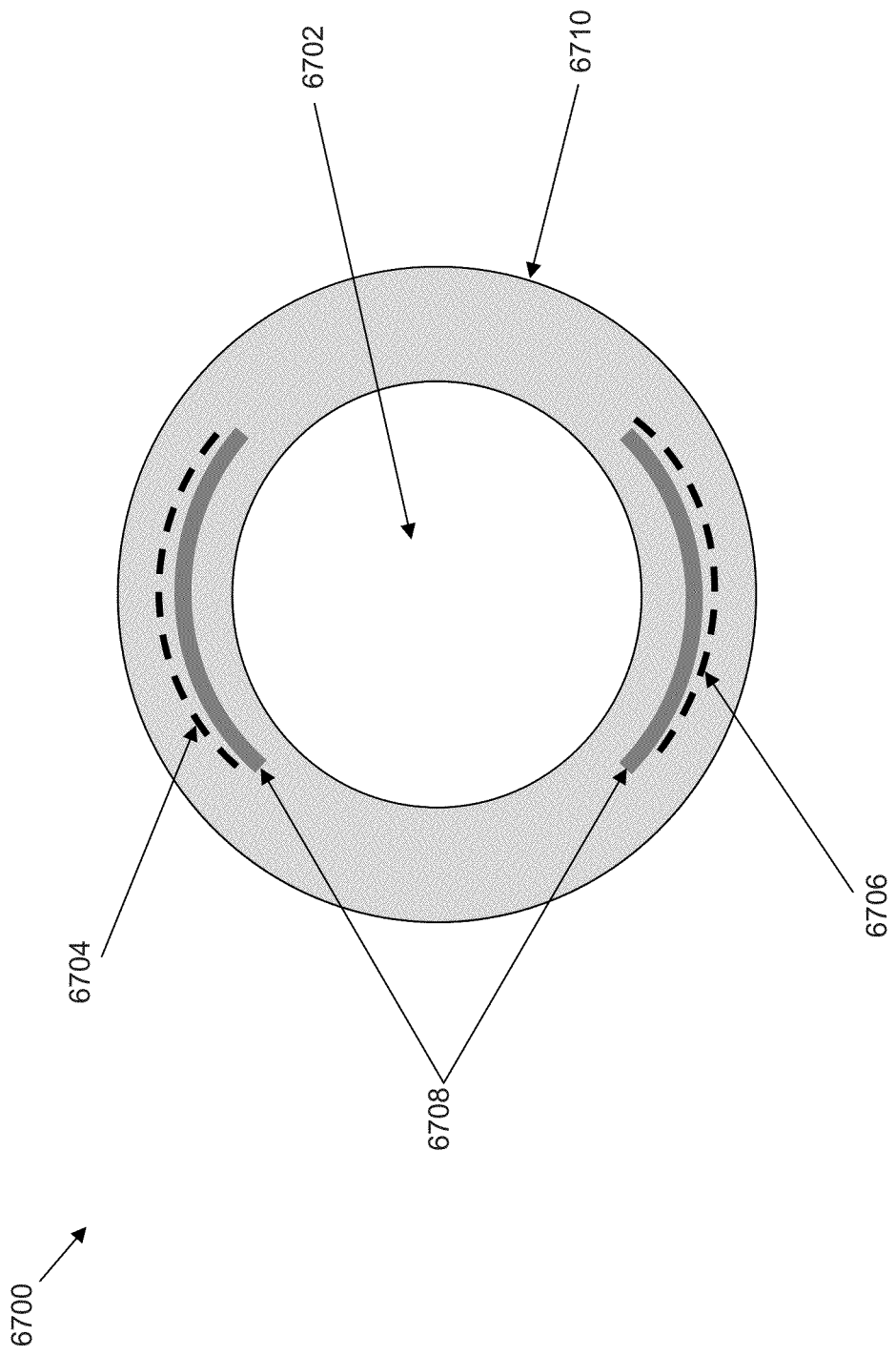
FIG. 67 shows an aerial view of a scleral ring having finger like members according to one embodiment.

FIG. 67 shows a scleral ring 6700 having a peripheral edge 6710 and an open aperture 6702. Located above open aperture 6702 is an incremental thickness region having an upper finger member 6704 and located below open aperture 6702 is an incremental thickness region having a lower finger member 6706. Scleral ring 6700 can also have trenches 6708 designed to receive finger members 6704 and 6706 when they are folded down by the eyelids of a wearer. Trenches 6708 are located adjacent to the inside of finger members 6704 and 6706. It should be noted that trenches 6808 are optional.

Figure 68:
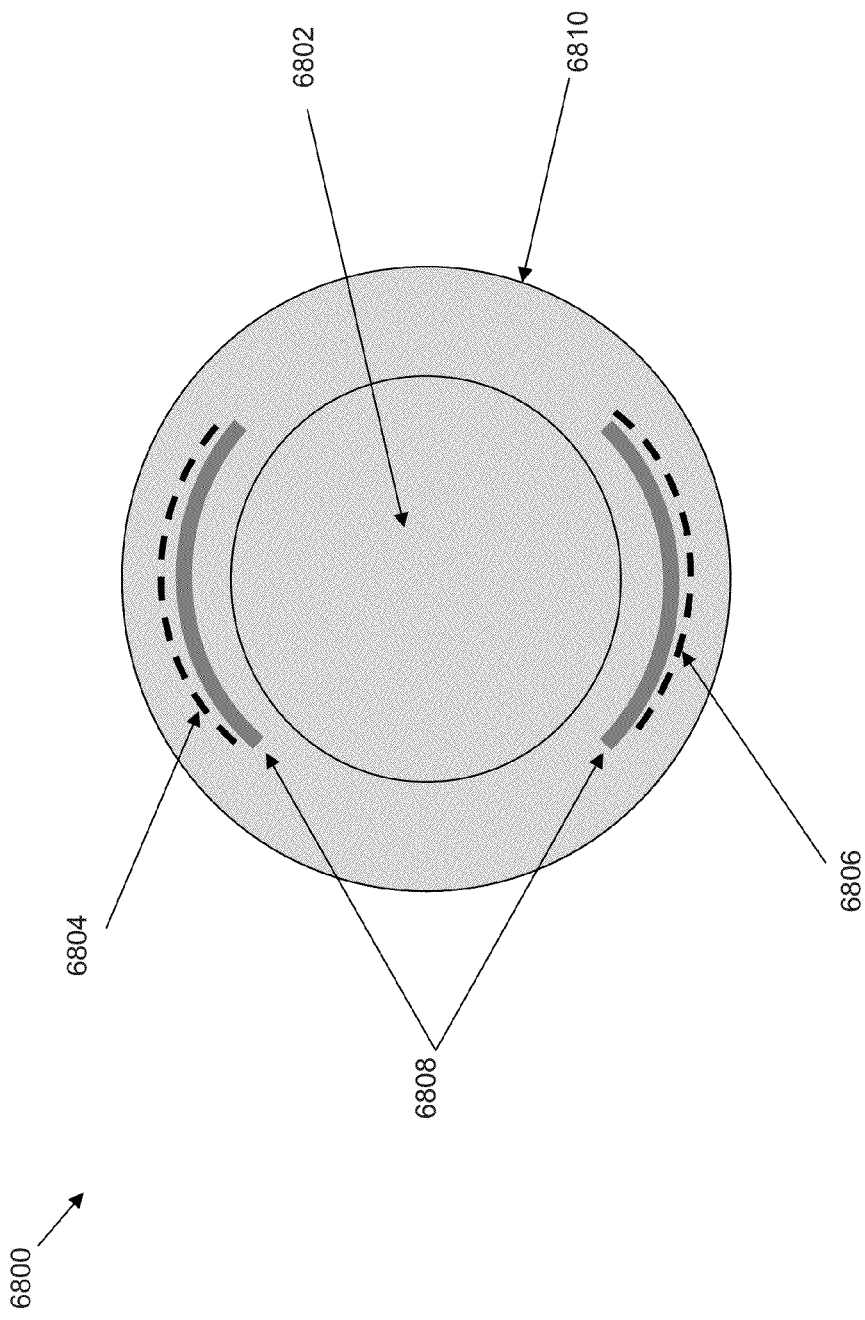
FIG. 68 shows an aerial view of a contact lens having finger like members according to one embodiment.

FIG. 68 shows a contact lens 6800 having a peripheral edge 6810 and an optic zone 6802. Located above optic zone 6802 is an incremental thickness region having an upper finger member 6804 and located below optic zone 6802 is an incremental thickness region having a lower finger member 6806. Contact lens 6800 can also have trenches 6808 designed to receive finger members 6804 and 6806 when they are folded down by the eyelids of a wearer. Trenches 6808 are located adjacent to the inside of finger members 6804 and 6806. It should be noted that trenches 6808 are optional.

Figure 69:
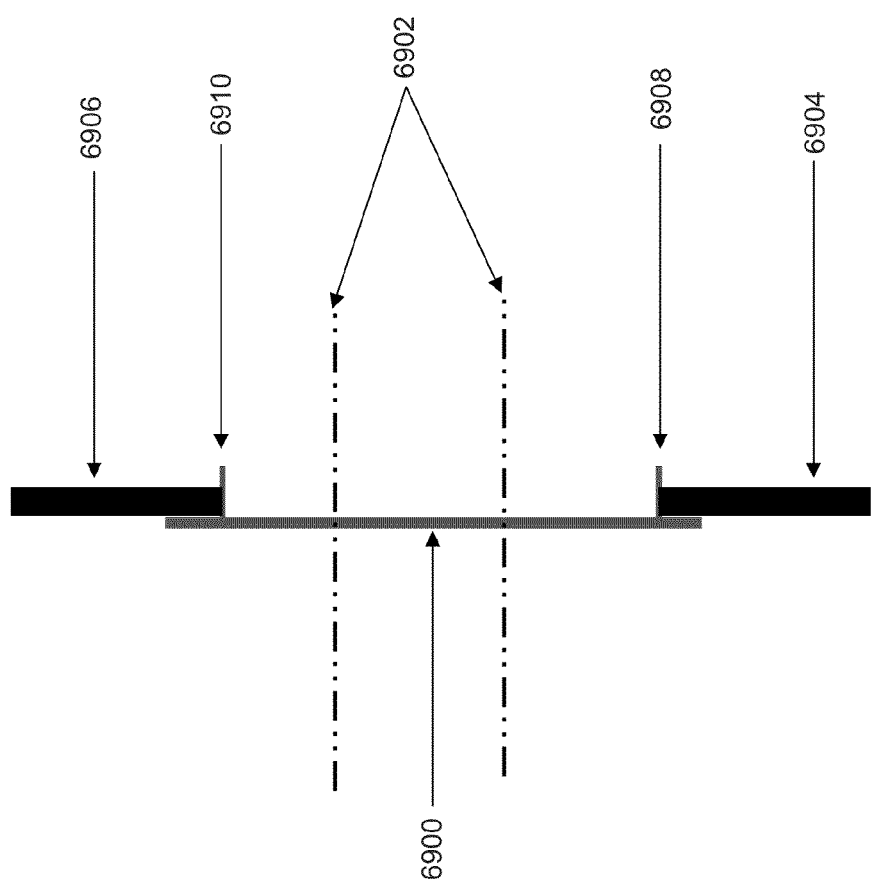
FIG. 69 shows a side view of a prosthesis having finger like members according to one embodiment.

FIG. 69 shows a side view of a contact lens 6900 having an optical zone 6902, an upper finger member 6910 and a lower finger member 6908. In FIG. 69 an upper eyelid 6906 is shown in contact with upper finger member 6910. Upper finger member 6910 lifts (elevates) upper eyelid 6906 when contact lens 6900 is worn. FIG. 69 also shows a lower eyelid 6904 in contact with lower finger member 6908. Lower finger member 6909 depresses (lowers) lower eyelid 6904 when contact lens 6900 is worn. While a contact lens is shown in FIG. 69 it will be appreciated that a scleral ring with finger members (see above description with respect to FIG. 67) would also be capable of lifting (elevating) and/or depressing (lowering) the upper and lower eyelids in the same way as described in FIG. 69.

Table 1 summarizes the effects that four different exemplarily prostheses had on different individual's eyes.

TABLE 1

Aperture Widening Results for Four different example lenses (I, J, K, and L)

| Age | Gender | Test Embodiment Contact Lenses that showed best widening of palpebral fissure | % widening for best lens(es) |
| --- | --- | --- | --- |
| 44 | Female | L | ~15% |
| 16 | Female | L, J | ~20% |
| 40 | Female | I, J, L | ~10% |
| 33 | Male | I, J, K | ~15% |
| 45 | Female | J, K, L | ~18% |
| 25 | Female | I, J, K, L | ~15% |
| 30 | Female | I, J, K, L | ~15% |
| 20 | Female | K | ~33% |
| 33 | Male | K | ~6% |
| 66 | Male | L | ~40% |

The specifications for lens I are as follows:
8.4 base curve/15.0 mm overall diameter/150 microns max thickness delta bump 1.0 mm-1.50 mm in from outer edge of the lens/aperture widening zone begins at the outer edge of the lens/general base thickness (excluding bump & outer edge) within the range of approximately 125 microns-175 microns/optical power equals −0.50 D The specifications for lens J are as follows:
8.4 base curve/15.0 mm overall diameter/300 microns max thickness delta bump 1.5 mm-2.0 mm in from outer edge of the lens/aperture widening zone begins at the outer edge of the lens/general base thickness (excluding bump & outer edge) within the range of approximately 125 microns-175 micron/optical power equals −0.50 D The specifications for lens K are as follows:
8.4 base curve/15.5 mm overall diameter/150 microns max thickness delta bump 1.0 mm-1.5 mm in from outer edge of the lens/aperture widening zone begins at the outer edge of the lens/general base thickness (excluding bump & outer edge) within the range of approximately 125 microns-175 microns/optical power equals −0.50 D The specifications for lens L are as follows
8.4 base curve/15.5 mm overall diameter/300 microns max thickness delta bump at 1.5 mm-2.0 mm in from the outer edge of the lens/aperture widening zone begins at the outer edge of the lens/general base thickness (excluding bump & outer edge) within the range of approximately 125 microns-175 microns/optical power equals −0.50 D Table 1 illustrates that specific lens work best for different individuals and that most individual's palpebral fissure can be widened by wearing a prosthesis comprising an aperture widening zone as described herein. It is appreciated that Table 1 is only an example of various lenses that can be worn and is not meant to limit the dimensions and/or widening capacities of prostheses described herein.

Some embodiments include a prosthesis capable of being worn by a wearer comprising an aperture widening zone located on its convex outer surface. The prosthesis has an overall diameter of Xmm, and the wearer's eye comprises a vertical aperture measurement of Ymm, whereby Xmm is at least 1 mm longer than Ymm. The aperture widening zone widens the palpebral fissure of the eye of a wearer.

In some embodiments the aperture widening zone depresses (lowers) the lower lid of a wearer. In some embodiments the aperture widening zone lifts (elevates) the upper lid of a wearer. In some embodiments the aperture widening zone lifts (elevates) the upper lid by at least 1 mm. In some embodiments the aperture widening zone depresses (lowers) the lower lid by at least 1 mm. In some embodiments the aperture widening zone elevates the upper lid by less than 1 mm and/or depresses the lower lid by less than 1 mm but widens the palpebral fissure of the wearer's eye by at least 1 mm.

The prosthesis comprises a material that is one of: hydrogel, silicon hydrogel, silicon, gas perm, hydrophilic, rigid and flexible.

In some embodiments the prosthesis that is corneo-scleral contact lens. In some embodiments the prosthesis is a soft contact lens. In some embodiments the prosthesis is a hybrid contact lens. In some embodiments the prosthesis is a scleral ring.

In some embodiments the aperture widening zone is located internal to the edge of the prosthesis. In some embodiments the aperture widening zone begins at the outer edge of the prosthesis.

In some embodiments the aperture widening zone is rotationally symmetric. In some embodiments the aperture widening zone is rotationally asymmetric.

In some embodiments the aperture widening zone has a maximum incremental thickness delta that is within the range of 25 microns and 1,000 microns. In some embodiments the aperture widening zone has a maximum incremental thickness delta that is within the range of 100 microns and 400 microns.

In some embodiments the aperture widening zone is located within a range of 3 mm and 8.5 mm from a geometrical center of the prosthesis. In some embodiments the aperture widening zone is located within a range of 5 mm and 7.75 mm from a geometrical center of the prosthesis.

In some embodiments the aperture widening zone is located within a range of 0.1 mm to 6.0 mm from an outer peripheral edge of the prosthesis. In some embodiments the aperture widening zone is located within a range from an outer peripheral edge of the prosthesis to 6.0 mm from the outer peripheral edge of the prosthesis.

In some embodiments the aperture widening zone has a maximum delta thickness located within a range of 0.5 mm to 3.0 mm from an outer peripheral edge of the prosthesis.

In some embodiments the aperture widening zone comprises a bump on the convex surface of the lens.

The scleral ring in some embodiments comprises an open central aperture. In some embodiments the scleral ring comprises a homogenous design. In some embodiments the scleral ring comprises a hybrid design.

In some embodiments the scleral ring comprises a flexible finger like member. In some embodiments the finger like member folds upon the blink of an eye in a direction towards the geometrical center of the scleral ring. In some embodiments the finger like member unfolds upon the opening of the eye lid in a direction away from the geometrical center of the scleral ring.

The prosthesis can be worn for a time of one of: continuously, daily, weekly and monthly.

In some embodiments the prosthesis is disposable. In some embodiments the prosthesis is reusable.

In some embodiments the prosthesis comprises an optical power. In some embodiments the prosthesis is devoid of optical power.

In some embodiments the aperture widening zone has a slope and a delta of maximum incremental thickness. In some embodiments the slope on the outside of the delta of maximum incremental thickness (closest to the outer edge of the prosthesis) is steeper than the slope on the inside (closest to the center of the prosthesis).

In some embodiments the prosthesis comprises a zone or region of increased surface friction. In some embodiments the prosthesis is devoid of a zone of incremental thickness or regressive thickness, but rather has a zone of increased surface friction located on its outer convex surface.

In some embodiments the width of the aperture widening zone is within the range of 0.5 mm to 6 mm.

In some embodiments the outer edge of the prosthesis approximates the edge of a conventional corneo-scleral contact lens.

In some embodiments the aperture widening zone that has a peak delta thickness which corresponds to a point located 0.1 mm or greater above the upper lid margin of the wearer when not wearing the prosthesis. In some embodiments the aperture widening zone that has a peak delta thickness which corresponds to a point located 0.1 mm or more below the lower lid margin of the wearer when not wearing the prosthesis. In some embodiments the peak delta thickness corresponds to a point located within the natural aperture of the wearer's eye. In some embodiments the peak delta thickness corresponds to a point located outside the natural aperture of the wearer's eye (meaning the distance of peak delta thickness to peak delta thickness measured thru the geometrical center of the prosthesis is larger than the vertical measurement between the upper lid margin and the lower lid margin (the vertical eye aperture).

In some embodiments the aperture widening zone has a diameter (not the width of the aperture widening zone) that falls within the range of 7 mm to 15 mm.

In some embodiments the prosthesis is a corneo-scleral contact lens. In some embodiments the corneo-scleral contact lens is a spherical single vision contact lens. In some embodiments the corneo-scleral contact lens is a multifocal contact lens. In some embodiments the corneo-scleral contact lens has a toric optical power. In some embodiments the corneo-scleral contact lens is a single vision sphero-cylinder contact lens.

In some embodiments the prosthesis comprises a rotationally symmetric aperture widening zone and is not stabilized. In some embodiments the prosthesis comprises a rotationally symmetric aperture widening zone and the prosthesis is devoid of a stabilization zone.

In some embodiments the prosthesis is devoid of a stabilization zone and thus free to rotate. In some embodiments the prosthesis is stabilized and thus not free to rotate.

In some embodiments the prosthesis has an aperture widening zone and a separate aperture stabilization zone.

In some embodiments the prosthesis has an aperture widening zone and the prosthesis is free to rotate during natural blinking In some embodiments the prosthesis comprises a colored area which adds to the cosmetic appearance of a larger eye when worn on the eye of a wearer. In some embodiments the colored area is one of: a limbal ring, colored ring, or accent color.

In some embodiments the aperture widening zone is located above and below the geometrical center along an imaginary vertical axis which crosses the geometrical center of the prosthesis In some embodiments the prosthesis comprises an aperture widening zone located to the right or left of the geometrical center along an imaginary vertical axis which crosses the geometrical center of the prosthesis.

Some embodiments include a prosthesis for a wearer's eye having an overall diameter of Xmm, and the wearer's eye having a vertical aperture measurement of Ymm, wherein Xmm is at least 1 mm longer than Ymm. The prosthesis has an aperture widening zone with an outer slope within the range of 3 degrees to 45 degrees.

Some embodiments include a prosthesis for a wearer's eye having an overall diameter of Xmm, and the wearer's eye having a vertical aperture measurement of Ymm, wherein Xmm is at least 1 mm longer than Ymm. The prosthesis has an aperture widening zone with an inner slope within the range of 1 degree to 15 degrees.

Some embodiments include a prosthesis having an aperture widening zone located superior and inferior to its geometrical center. The aperture widening zone has a thickness slope. The thickness slope exceeding 50 microns of added thickness per millimeter Some embodiments include a prosthesis having an aperture widening zone on its convex surface. The aperture widening zone causing a bump on the convex surface. The aperture widening zone has an outer slope thickness that is greater than 50 microns of added thickness per mm.

Some embodiments include a prosthesis having an aperture widening zone on its convex surface. The aperture widening zone causing a bump on the convex surface. The aperture widening zone has an inner slope thickness that is less than 50 microns of added thickness per mm.

In some embodiments the outer slope thickness of the aperture widening zone is greater than 100 microns of added thickness per mm. In some embodiments the outer slope thickness of the aperture widening zone is greater than 150 microns of added thickness per mm. In some embodiments the outer slope thickness of the aperture widening zone is greater than 200 microns of added thickness per mm. In some embodiments the outer slope thickness of the aperture widening zone is greater than 300 microns of added thickness per mm.

In some embodiments the inner slope thickness of the aperture widening zone is less than 100 microns of added thickness per mm. In some embodiments the inner slope thickness of the aperture widening zone is less than 150 microns of added thickness per mm. In some embodiments the inner slope thickness of the aperture widening zone is less than 200 microns of added thickness per mm. In some embodiments the inner slope thickness of the aperture widening zone is less than 300 microns of added thickness per mm.

In some embodiments the aperture widening zone has a bump on the convex surface of the prosthesis. In some embodiments the bump is located vertically above and below the geometrical center of the prosthesis.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the, hardware, methods and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A prosthesis capable of being worn on the eye of a wearer comprising:
    a convex surface;
    a concave surface; and
    an aperture widening zone comprising a surface feature that is located on the convex surface of the prosthesis and that is different from the rest of the prosthesis, the surface feature comprising an area of incremental thickness with a maximum added thickness delta located at least 5.25 mm from a geometrical center of the prosthesis;
    wherein the maximum added thickness delta is configured to be located at or exterior to the limbus of a wearer's eye when the prosthesis is worn on the eye;
    wherein the maximum added thickness delta is at least 200 microns;
    wherein the aperture widening zone has a minimum vertical dimension of greater than or equal to 10.5 mm; and
    wherein the aperture widening zone is configured to widen the natural palpebral fissure of a wearer's eye.

2. The prosthesis of claim 1, wherein the maximum added thickness delta is located at least 5.5 mm from the geometrical center of the prosthesis.

3. The prosthesis of claim 1, wherein the maximum added thickness delta is within the range of 200 microns and 1,000 microns.

4. The prosthesis of claim 1, wherein the maximum added thickness delta is located between 0.5 mm and 3 mm from a peripheral edge of the prosthesis.

5. The prosthesis of claim 1, wherein the surface feature comprises an outer slope and an inner slope with the maximum added thickness delta located between the outer slope and the inner slope, and wherein the outer slope is greater than the inner slope.

6. The prosthesis of claim 1, wherein the surface feature comprises an outer slope and an inner slope with the maximum added thickness delta located between the outer slope and the inner slope, and wherein the inner slope has a thickness slope of 350 microns per millimeter or less.

7. The prosthesis of claim 1, wherein the surface feature comprises an outer slope and an inner slope with the maximum added thickness delta located between the outer slope and the inner slope, and wherein the outer slope has a thickness slope of 50 microns per millimeter or greater.

8. The prosthesis of claim 1, wherein the maximum added thickness delta is at least 300 microns.

9. The prosthesis of claim 1, wherein the surface feature further comprises an area of increased surface friction.

10. The prosthesis of claim 1, wherein the surface feature comprises a ring having an incremental thickness diameter of at least 10.5 mm.

11. The prosthesis of claim 9, wherein the increased surface friction is provided by at least one of: a surface treatment, a coating, a material different from the material used to form the prosthesis, surface dimples, surface irregularities, or combinations thereof.

12. The prosthesis of claim 1, wherein the aperture widening zone includes a plurality of surface features.

13. The prosthesis of claim 1, further comprising a colored accent.

14. The prosthesis of claim 13, wherein the colored accent is selected from the group consisting of: a limbal ring, a colored ring, a tinted iris ring, and a combination thereof.

15. The prosthesis of claim 13, wherein at least a portion of the colored accent is located at or external to 5.5 mm from a geometric center of the prosthesis.

16. The prosthesis of claim 13, wherein the colored accent is a limbal ring, and wherein diameter of a portion of the limbal ring is equal to or larger than 11 mm.

17. The prosthesis of claim 1, wherein the minimum vertical dimension is greater than or equal to 13.5 mm.

18. The prosthesis of claim 1, wherein the minimum vertical dimension is greater than or equal to 11.5 mm.

19. The prosthesis of claim 1, wherein the prosthesis is configured to widen the natural palpebral fissure of the wearer's eye by at least 0.5 mm.

20. The prosthesis of claim 1, wherein the prosthesis is configured to be capable of rotation when worn on the eye.

21. The prosthesis of claim 1, wherein the prosthesis is a corneo-scleral lens.

22. The prosthesis of claim 1, wherein the prosthesis is a scleral ring.

23. The prosthesis of claim 1, wherein the aperture widening zone is rotationally symmetric about the geometrical center of the prosthesis.

24. The prosthesis of claim 1, wherein the maximum added thickness delta is rotationally symmetric about the geometrical center of the prosthesis.

25. A prosthesis comprising:
a peripheral edge;
a geometrical center; and
an aperture widening zone having a minimum vertical dimension of 10.5 mm or greater, the aperture widening zone comprising an outer slope, an inner slope, a first point of maximum added thickness delta, a second point of maximum added thickness delta, and an incremental thickness diameter measured from the first point of maximum added thickness delta to the second point of maximum added thickness delta thru the geometrical center of the prosthesis;
wherein the outer slope has a thickness slope of 50 microns per millimeter or greater;
wherein the first point and the second point of maximum added thickness delta of the aperture widening zone each have an added thickness of 200 microns or greater;
wherein the first point and the second point of maximum added thickness delta of the aperture widening zone are located between 1 mm and 3 mm from the peripheral edge;
wherein the incremental thickness diameter is 10.5 mm or greater; and
wherein the first point of maximum added thickness delta and the second point of maximum added thickness delta are configured to be located at or exterior to the limbus of a wearer's eye when the prosthesis is worn on the eye.

26. The prosthesis of claim 25, further comprising an overall diameter of 14.0 mm or greater measured from a first point on the peripheral edge to a second point on an opposing peripheral edge thru the geometrical center of the prosthesis and the aperture widening zone.

27. The prosthesis of claim 1, wherein the surface feature comprises a discontinuous ring having an incremental thickness diameter of at least 10.5 mm.

28. The prosthesis of claim 1, further comprising:
a peripheral edge and an overall diameter of greater than or equal to 14.0 mm measured from a first point on the peripheral edge to a second point on an opposing peripheral edge thru the geometrical center of the prosthesis; and
wherein the maximum added thickness delta is located no more than 1.75 mm from the first point on the peripheral edge of the prosthesis.

29. The prosthesis of claim 1, further comprising a peripheral edge defining an outer perimeter of the prosthesis, wherein the peripheral edge comprises a round shape.

* * * * *